US012629436B2

(12) United States Patent
Callahan et al.

(10) Patent No.: US 12,629,436 B2
(45) Date of Patent: May 19, 2026

(54) PORTABLE WAND SYSTEMS AND METHODS OF USING THE SAME TO INDICATE AND VERIFY SURFACE TREATMENT APPLICATIONS

(71) Applicant: The Boeing Company, Chicago, IL (US)

(72) Inventors: Kevin S. Callahan, Shoreline, WA (US); Michael K. Klein, Bothell, WA (US); Christopher E. Plass, Snohomish, WA (US)

(73) Assignee: The Boeing Company, Arlington, VA (US)

( * ) Notice: Subject to any disclaimer, the term of this patent is extended or adjusted under 35 U.S.C. 154(b) by 1230 days.

(21) Appl. No.: 17/515,313

(22) Filed: Oct. 29, 2021

(65) Prior Publication Data

US 2022/0152240 A1 May 19, 2022

Related U.S. Application Data

(60) Provisional application No. 63/115,010, filed on Nov. 17, 2020.

(51) Int. Cl.
| | |
|---|---|
| *G01N 21/00* | (2006.01) |
| *A61L 2/10* | (2006.01) |
| *A61N 5/00* | (2006.01) |
| *G01N 23/00* | (2006.01) |
| *H04W 4/80* | (2018.01) |

(52) U.S. Cl.
CPC ................ *A61L 2/10* (2013.01); *H04W 4/80* (2018.02)

(58) Field of Classification Search
CPC ..... A61L 2/10; A61L 2/18; A61L 2/22; A61L 2/24; A61L 2202/11; A61L 2202/14;
(Continued)

(56) References Cited

U.S. PATENT DOCUMENTS

| | | | |
|---|---|---|---|
| 9,272,058 | B1 | 3/2016 | Montgomery |
| 9,421,290 | B2 * | 8/2016 | Victor .................... G01R 33/07 |

(Continued)

FOREIGN PATENT DOCUMENTS

| | | |
|---|---|---|
| AU | 2015346482 A1 | 6/2017 |
| EP | 3915595 A2 | 12/2021 |

(Continued)

OTHER PUBLICATIONS

European Patent Office (EPO) Office Action, Oct. 12, 2023, for related EP Application No. 21180276.4, Applicant The Boeing Company, 4 pages.

(Continued)

*Primary Examiner* — Monzer R Chorbaji

(57) ABSTRACT

There is provided a portable wand system having a wand applicator, a wand controller subsystem, a selector assembly, an indicator element, and a power assembly. The wand controller subsystem includes a computer program, and a memory unit storing paths learned and recorded during a learn mode, by an operator manually moving the wand applicator. The paths include desired paths in stay-in zones to be surface treated, and include stay-out zone paths in, or near, stay-out zones to be avoided. The portable wand system is used in an operation mode to measure the operator manually moving the wand applicator in operation paths, based on the desired paths. For a selected stay-in zone, the portable wand system compares the operation path to the desired path, and indicates when the operation path deviates from the desired path, and when the wand applicator is in proximity to, and oriented towards, the stay-out zones.

20 Claims, 21 Drawing Sheets

(58) Field of Classification Search
CPC . A61L 2202/16; A61L 2202/25; B64D 11/00;
H04W 4/80
USPC .............. 422/24, 105, 119–120; 250/453.11,
250/454.11, 455.11, 492.1
See application file for complete search history.

(56) References Cited

U.S. PATENT DOCUMENTS

| | | | |
|---|---|---|---|
| 9,662,410 | B2 | 5/2017 | Mackin |
| 9,993,571 | B2 | 6/2018 | Lin et al. |
| 10,272,166 | B2 | 4/2019 | Mackin |
| 10,413,622 | B2 | 9/2019 | Mackin |
| 10,512,704 | B2 | 12/2019 | Dytioco et al. |
| 10,702,618 | B2 | 7/2020 | Callahan |
| 10,918,748 | B2 | 2/2021 | Childress et al. |
| 2010/0104471 | A1* | 4/2010 | Harmon .................... A61L 2/10 |
| | | | 422/186.3 |
| 2012/0280147 | A1* | 11/2012 | Douglas .................... A61L 2/10 |
| | | | 250/492.1 |
| 2021/0128764 | A1 | 5/2021 | Childress et al. |

FOREIGN PATENT DOCUMENTS

| | | | |
|---|---|---|---|
| EP | 3915596 | A2 | 12/2021 |
| WO | 2020195017 | A1 | 10/2020 |

OTHER PUBLICATIONS

Pending U.S. Appl. No. 16/987,493, entitled "Portable Sanitizing Systems and Methods", Inventor Jamie J. Childress, filed Aug. 7, 2020, Applicant The Boeing Company, 42 pages.
Pending U.S. Appl. No. 17/016,466, entitled "Portable Sanitizing System Having a Backpack Assembly Coupled to a Wand Assembly", Inventor Jamie J. Childress, filed Sep. 10, 2020, Applicant The Boeing Company, 43 pages.
Extended European Search Report (EESR), European Patent Office, Feb. 28, 2022, for Application No. EP21194416.0, Applicant The Boeing Company, 5 pages.
Pending U.S. Appl. No. 16/987,526, entitled "Portable Sanitizing Systems and Methods", Arthur Edward Brockschmidt, Jr., et al., filed Aug. 7, 2020, Applicant The Boeing Company, 61 pages.
Pending U.S. Appl. No. 16/990,908, entitled "Portable Wand Systems and Methods of Using the Same to Indicate and Verify Surface Treatment Applications", Inventor Kevin S. Callahan, filed Aug. 11, 2020, Applicant The Boeing Company, 65 pages.
Japanese First Office Action Notice of Refusal, Japanese Version and English Translation, Issued May 8, 2025, for a counterpart Japanese foreign patent application No. 2021-176232, Applicant The Boeing Company, 4 total pages.
Extended European Search Report (EESR), European Patent Office, Dec. 15, 2021, for related Application No. EP21180276.4, Applicant The Boeing Company, 8 pages.

* cited by examiner

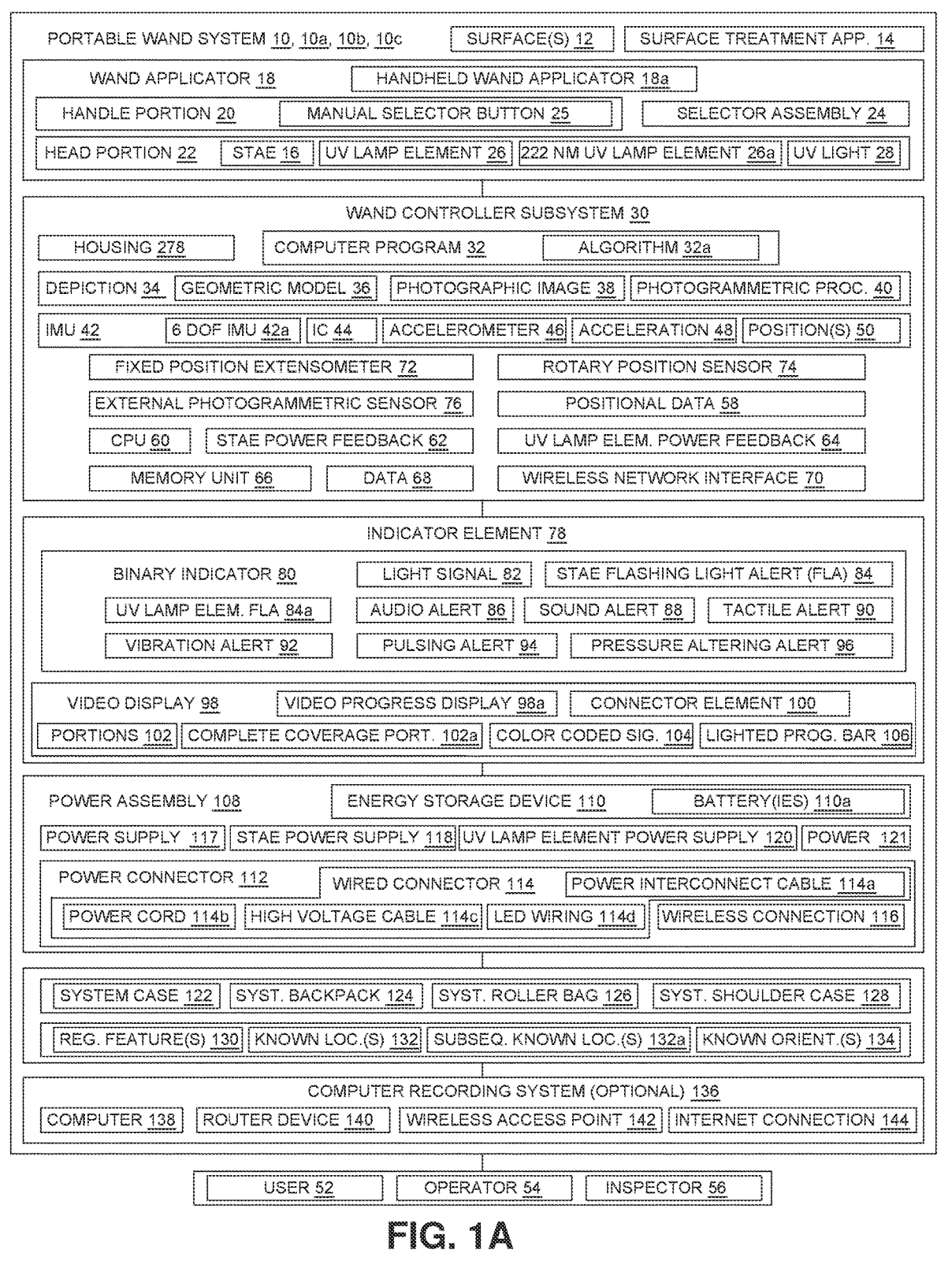

PORTABLE WAND SYSTEM 10, 10a, 10b, 10c | SURFACE(S) 12 | SURFACE TREATMENT APP. 14

WAND APPLICATOR 18 | HANDHELD WAND APPLICATOR 18a

HANDLE PORTION 20 | MANUAL SELECTOR BUTTON 25 | SELECTOR ASSEMBLY 24

HEAD PORTION 22 | STAE 16 | UV LAMP ELEMENT 26 | 222 NM UV LAMP ELEMENT 26a | UV LIGHT 28

WAND CONTROLLER SUBSYSTEM 30

HOUSING 278 | COMPUTER PROGRAM 32 | ALGORITHM 32a

DEPICTION 34 | GEOMETRIC MODEL 36 | PHOTOGRAPHIC IMAGE 38 | PHOTOGRAMMETRIC PROC. 40

IMU 42 | 6 DOF IMU 42a | IC 44 | ACCELEROMETER 46 | ACCELERATION 48 | POSITION(S) 50

FIXED POSITION EXTENSOMETER 72 | ROTARY POSITION SENSOR 74

EXTERNAL PHOTOGRAMMETRIC SENSOR 76 | POSITIONAL DATA 58

CPU 60 | STAE POWER FEEDBACK 62 | UV LAMP ELEM. POWER FEEDBACK 64

MEMORY UNIT 66 | DATA 68 | WIRELESS NETWORK INTERFACE 70

INDICATOR ELEMENT 78

BINARY INDICATOR 80 | LIGHT SIGNAL 82 | STAE FLASHING LIGHT ALERT (FLA) 84

UV LAMP ELEM. FLA 84a | AUDIO ALERT 86 | SOUND ALERT 88 | TACTILE ALERT 90

VIBRATION ALERT 92 | PULSING ALERT 94 | PRESSURE ALTERING ALERT 96

VIDEO DISPLAY 98 | VIDEO PROGRESS DISPLAY 98a | CONNECTOR ELEMENT 100

PORTIONS 102 | COMPLETE COVERAGE PORT. 102a | COLOR CODED SIG. 104 | LIGHTED PROG. BAR 106

POWER ASSEMBLY 108 | ENERGY STORAGE DEVICE 110 | BATTERY(IES) 110a

POWER SUPPLY 117 | STAE POWER SUPPLY 118 | UV LAMP ELEMENT POWER SUPPLY 120 | POWER 121

POWER CONNECTOR 112 | WIRED CONNECTOR 114 | POWER INTERCONNECT CABLE 114a

POWER CORD 114b | HIGH VOLTAGE CABLE 114c | LED WIRING 114d | WIRELESS CONNECTION 116

SYSTEM CASE 122 | SYST. BACKPACK 124 | SYST. ROLLER BAG 126 | SYST. SHOULDER CASE 128

REG. FEATURE(S) 130 | KNOWN LOC.(S) 132 | SUBSEQ. KNOWN LOC.(S) 132a | KNOWN ORIENT.(S) 134

COMPUTER RECORDING SYSTEM (OPTIONAL) 136

COMPUTER 138 | ROUTER DEVICE 140 | WIRELESS ACCESS POINT 142 | INTERNET CONNECTION 144

USER 52 | OPERATOR 54 | INSPECTOR 56

FIG. 1A

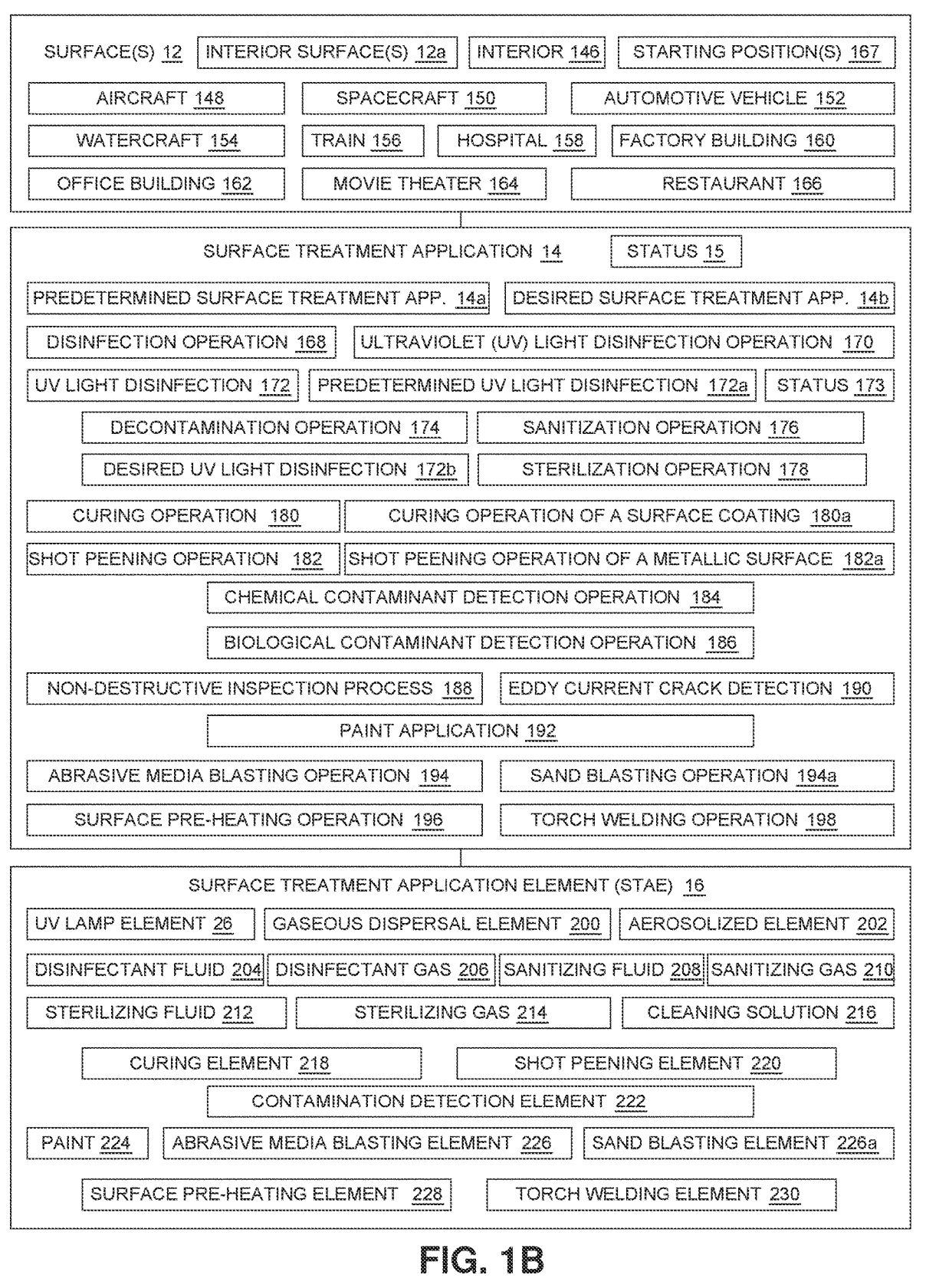

SURFACE(S) 12 | INTERIOR SURFACE(S) 12a | INTERIOR 146 | STARTING POSITION(S) 167

AIRCRAFT 148 | SPACECRAFT 150 | AUTOMOTIVE VEHICLE 152

WATERCRAFT 154 | TRAIN 156 | HOSPITAL 158 | FACTORY BUILDING 160

OFFICE BUILDING 162 | MOVIE THEATER 164 | RESTAURANT 166

SURFACE TREATMENT APPLICATION 14 | STATUS 15

PREDETERMINED SURFACE TREATMENT APP. 14a | DESIRED SURFACE TREATMENT APP. 14b

DISINFECTION OPERATION 168 | ULTRAVIOLET (UV) LIGHT DISINFECTION OPERATION 170

UV LIGHT DISINFECTION 172 | PREDETERMINED UV LIGHT DISINFECTION 172a | STATUS 173

DECONTAMINATION OPERATION 174 | SANITIZATION OPERATION 176

DESIRED UV LIGHT DISINFECTION 172b | STERILIZATION OPERATION 178

CURING OPERATION 180 | CURING OPERATION OF A SURFACE COATING 180a

SHOT PEENING OPERATION 182 | SHOT PEENING OPERATION OF A METALLIC SURFACE 182a

CHEMICAL CONTAMINANT DETECTION OPERATION 184

BIOLOGICAL CONTAMINANT DETECTION OPERATION 186

NON-DESTRUCTIVE INSPECTION PROCESS 188 | EDDY CURRENT CRACK DETECTION 190

PAINT APPLICATION 192

ABRASIVE MEDIA BLASTING OPERATION 194 | SAND BLASTING OPERATION 194a

SURFACE PRE-HEATING OPERATION 196 | TORCH WELDING OPERATION 198

SURFACE TREATMENT APPLICATION ELEMENT (STAE) 16

UV LAMP ELEMENT 26 | GASEOUS DISPERSAL ELEMENT 200 | AEROSOLIZED ELEMENT 202

DISINFECTANT FLUID 204 | DISINFECTANT GAS 206 | SANITIZING FLUID 208 | SANITIZING GAS 210

STERILIZING FLUID 212 | STERILIZING GAS 214 | CLEANING SOLUTION 216

CURING ELEMENT 218 | SHOT PEENING ELEMENT 220

CONTAMINATION DETECTION ELEMENT 222

PAINT 224 | ABRASIVE MEDIA BLASTING ELEMENT 226 | SAND BLASTING ELEMENT 226a

SURFACE PRE-HEATING ELEMENT 228 | TORCH WELDING ELEMENT 230

FIG. 1B

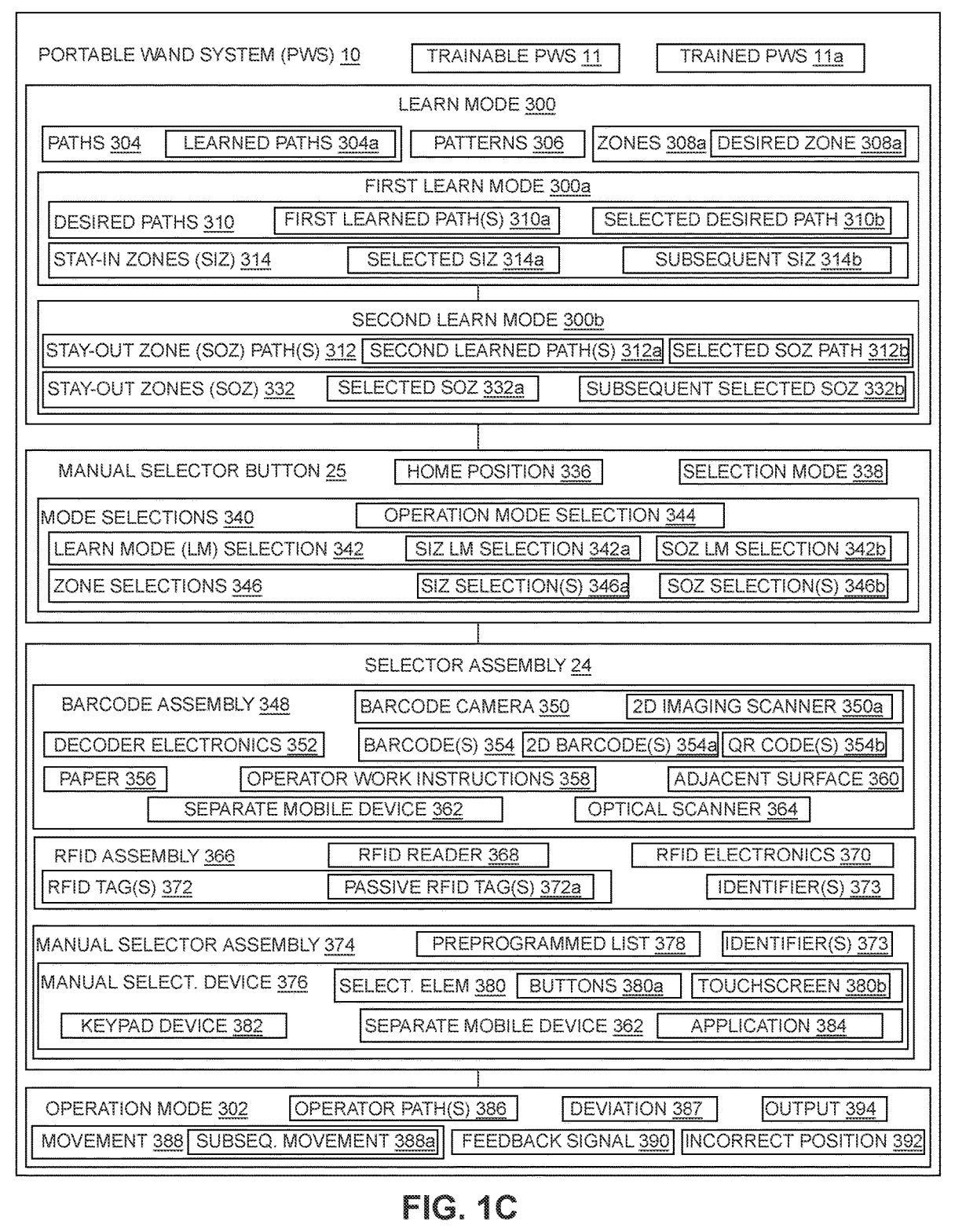

PORTABLE WAND SYSTEM (PWS) 10 | TRAINABLE PWS 11 | TRAINED PWS 11a

LEARN MODE 300

PATHS 304 | LEARNED PATHS 304a | PATTERNS 306 | ZONES 308a | DESIRED ZONE 308a

FIRST LEARN MODE 300a

DESIRED PATHS 310 | FIRST LEARNED PATH(S) 310a | SELECTED DESIRED PATH 310b

STAY-IN ZONES (SIZ) 314 | SELECTED SIZ 314a | SUBSEQUENT SIZ 314b

SECOND LEARN MODE 300b

STAY-OUT ZONE (SOZ) PATH(S) 312 | SECOND LEARNED PATH(S) 312a | SELECTED SOZ PATH 312b

STAY-OUT ZONES (SOZ) 332 | SELECTED SOZ 332a | SUBSEQUENT SELECTED SOZ 332b

MANUAL SELECTOR BUTTON 25 | HOME POSITION 336 | SELECTION MODE 338

MODE SELECTIONS 340 | OPERATION MODE SELECTION 344

LEARN MODE (LM) SELECTION 342 | SIZ LM SELECTION 342a | SOZ LM SELECTION 342b

ZONE SELECTIONS 346 | SIZ SELECTION(S) 346a | SOZ SELECTION(S) 346b

SELECTOR ASSEMBLY 24

BARCODE ASSEMBLY 348 | BARCODE CAMERA 350 | 2D IMAGING SCANNER 350a

DECODER ELECTRONICS 352 | BARCODE(S) 354 | 2D BARCODE(S) 354a | QR CODE(S) 354b

PAPER 356 | OPERATOR WORK INSTRUCTIONS 358 | ADJACENT SURFACE 360

SEPARATE MOBILE DEVICE 362 | OPTICAL SCANNER 364

RFID ASSEMBLY 366 | RFID READER 368 | RFID ELECTRONICS 370

RFID TAG(S) 372 | PASSIVE RFID TAG(S) 372a | IDENTIFIER(S) 373

MANUAL SELECTOR ASSEMBLY 374 | PREPROGRAMMED LIST 378 | IDENTIFIER(S) 373

MANUAL SELECT. DEVICE 376 | SELECT. ELEM 380 | BUTTONS 380a | TOUCHSCREEN 380b

KEYPAD DEVICE 382 | SEPARATE MOBILE DEVICE 362 | APPLICATION 384

OPERATION MODE 302 | OPERATOR PATH(S) 386 | DEVIATION 387 | OUTPUT 394

MOVEMENT 388 | SUBSEQ. MOVEMENT 388a | FEEDBACK SIGNAL 390 | INCORRECT POSITION 392

FIG. 1C

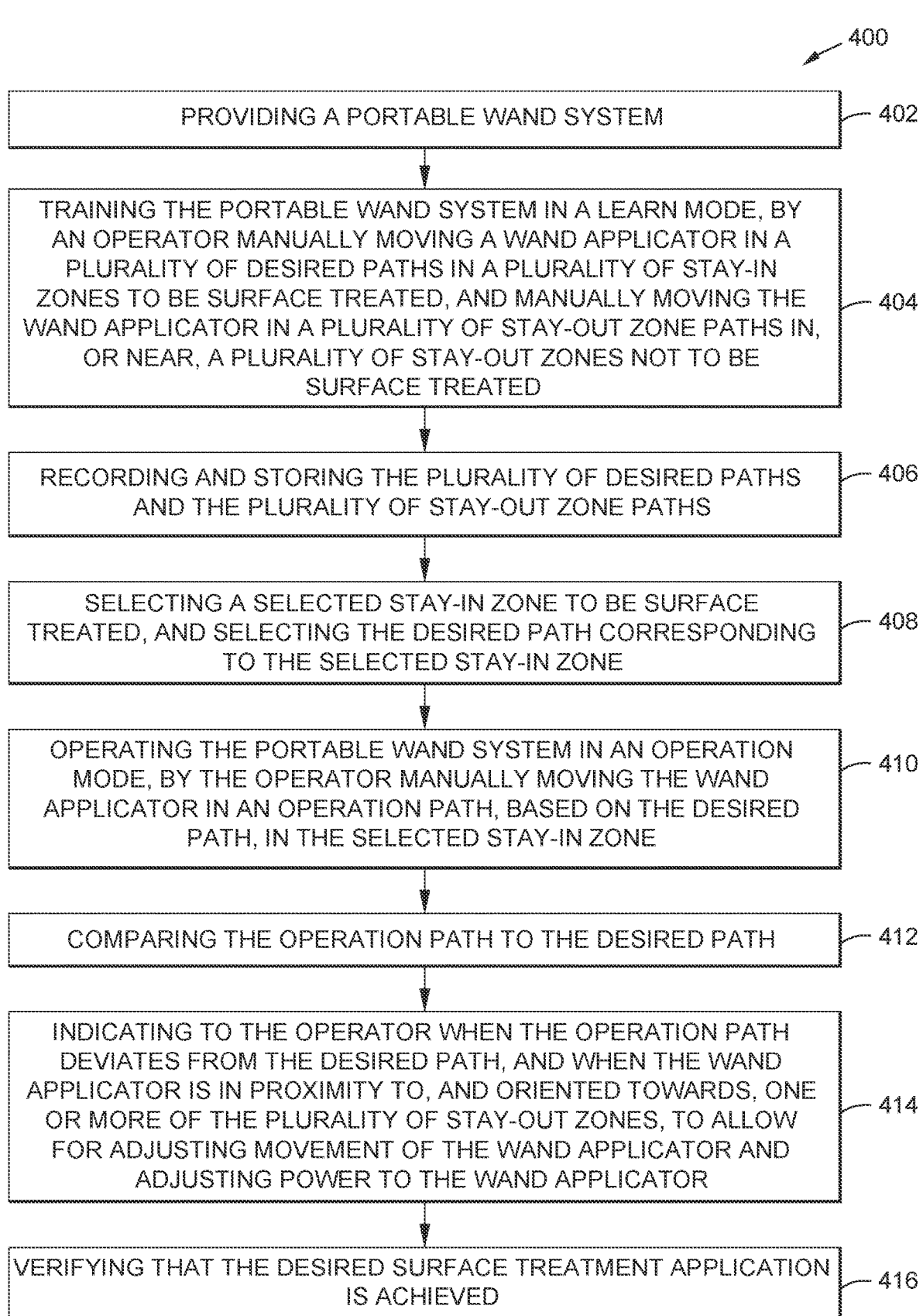

400

PROVIDING A PORTABLE WAND SYSTEM — 402

TRAINING THE PORTABLE WAND SYSTEM IN A LEARN MODE, BY AN OPERATOR MANUALLY MOVING A WAND APPLICATOR IN A PLURALITY OF DESIRED PATHS IN A PLURALITY OF STAY-IN ZONES TO BE SURFACE TREATED, AND MANUALLY MOVING THE WAND APPLICATOR IN A PLURALITY OF STAY-OUT ZONE PATHS IN, OR NEAR, A PLURALITY OF STAY-OUT ZONES NOT TO BE SURFACE TREATED — 404

RECORDING AND STORING THE PLURALITY OF DESIRED PATHS AND THE PLURALITY OF STAY-OUT ZONE PATHS — 406

SELECTING A SELECTED STAY-IN ZONE TO BE SURFACE TREATED, AND SELECTING THE DESIRED PATH CORRESPONDING TO THE SELECTED STAY-IN ZONE — 408

OPERATING THE PORTABLE WAND SYSTEM IN AN OPERATION MODE, BY THE OPERATOR MANUALLY MOVING THE WAND APPLICATOR IN AN OPERATION PATH, BASED ON THE DESIRED PATH, IN THE SELECTED STAY-IN ZONE — 410

COMPARING THE OPERATION PATH TO THE DESIRED PATH — 412

INDICATING TO THE OPERATOR WHEN THE OPERATION PATH DEVIATES FROM THE DESIRED PATH, AND WHEN THE WAND APPLICATOR IS IN PROXIMITY TO, AND ORIENTED TOWARDS, ONE OR MORE OF THE PLURALITY OF STAY-OUT ZONES, TO ALLOW FOR ADJUSTING MOVEMENT OF THE WAND APPLICATOR AND ADJUSTING POWER TO THE WAND APPLICATOR — 414

VERIFYING THAT THE DESIRED SURFACE TREATMENT APPLICATION IS ACHIEVED — 416

FIG. 7

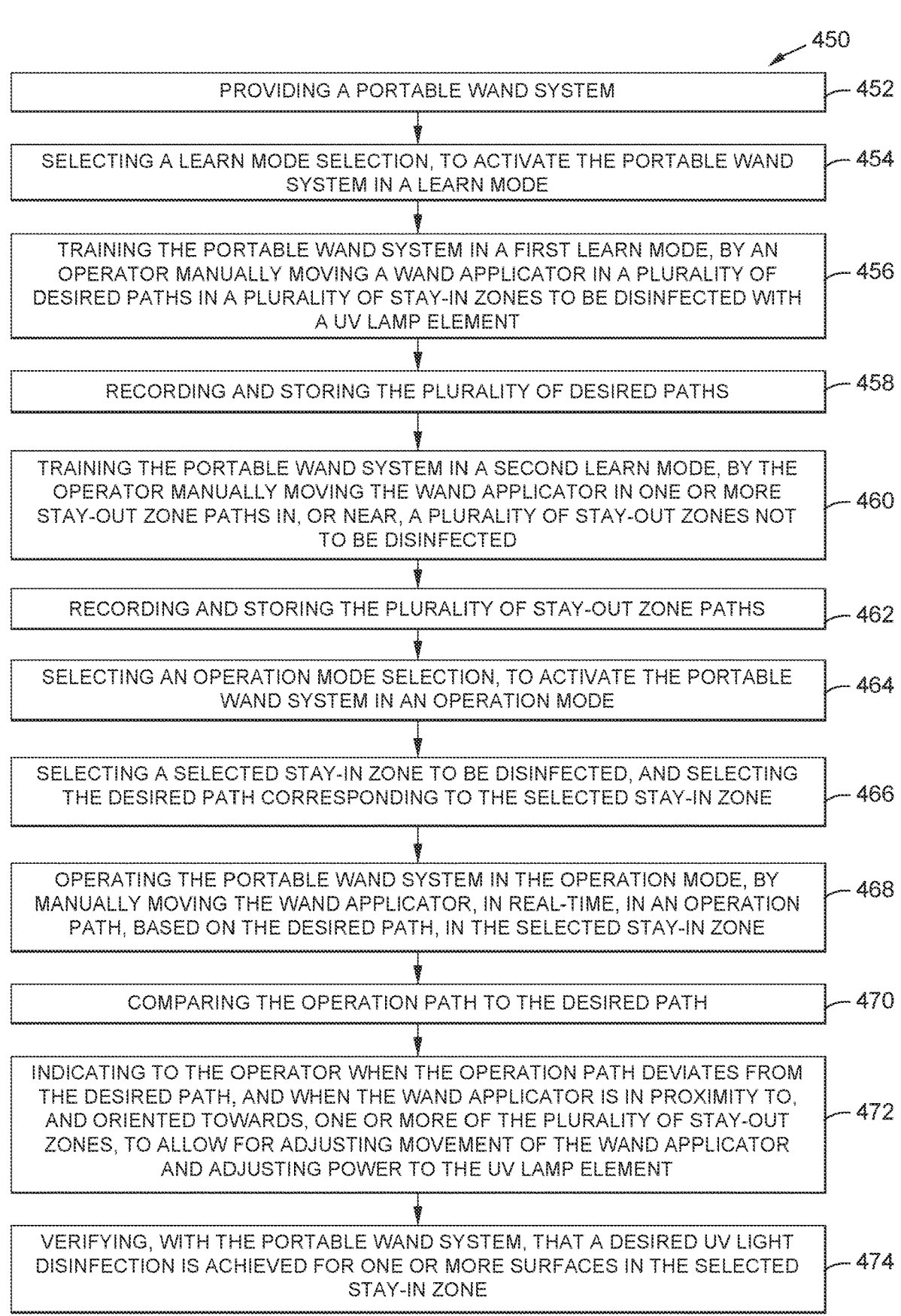

450

PROVIDING A PORTABLE WAND SYSTEM — 452

SELECTING A LEARN MODE SELECTION, TO ACTIVATE THE PORTABLE WAND SYSTEM IN A LEARN MODE — 454

TRAINING THE PORTABLE WAND SYSTEM IN A FIRST LEARN MODE, BY AN OPERATOR MANUALLY MOVING A WAND APPLICATOR IN A PLURALITY OF DESIRED PATHS IN A PLURALITY OF STAY-IN ZONES TO BE DISINFECTED WITH A UV LAMP ELEMENT — 456

RECORDING AND STORING THE PLURALITY OF DESIRED PATHS — 458

TRAINING THE PORTABLE WAND SYSTEM IN A SECOND LEARN MODE, BY THE OPERATOR MANUALLY MOVING THE WAND APPLICATOR IN ONE OR MORE STAY-OUT ZONE PATHS IN, OR NEAR, A PLURALITY OF STAY-OUT ZONES NOT TO BE DISINFECTED — 460

RECORDING AND STORING THE PLURALITY OF STAY-OUT ZONE PATHS — 462

SELECTING AN OPERATION MODE SELECTION, TO ACTIVATE THE PORTABLE WAND SYSTEM IN AN OPERATION MODE — 464

SELECTING A SELECTED STAY-IN ZONE TO BE DISINFECTED, AND SELECTING THE DESIRED PATH CORRESPONDING TO THE SELECTED STAY-IN ZONE — 466

OPERATING THE PORTABLE WAND SYSTEM IN THE OPERATION MODE, BY MANUALLY MOVING THE WAND APPLICATOR, IN REAL-TIME, IN AN OPERATION PATH, BASED ON THE DESIRED PATH, IN THE SELECTED STAY-IN ZONE — 468

COMPARING THE OPERATION PATH TO THE DESIRED PATH — 470

INDICATING TO THE OPERATOR WHEN THE OPERATION PATH DEVIATES FROM THE DESIRED PATH, AND WHEN THE WAND APPLICATOR IS IN PROXIMITY TO, AND ORIENTED TOWARDS, ONE OR MORE OF THE PLURALITY OF STAY-OUT ZONES, TO ALLOW FOR ADJUSTING MOVEMENT OF THE WAND APPLICATOR AND ADJUSTING POWER TO THE UV LAMP ELEMENT — 472

VERIFYING, WITH THE PORTABLE WAND SYSTEM, THAT A DESIRED UV LIGHT DISINFECTION IS ACHIEVED FOR ONE OR MORE SURFACES IN THE SELECTED STAY-IN ZONE — 474

SPECIFICATION
AND DESIGN — 552

MATERIAL
PROCUREMENT — 554

COMPONENT AND
SUBASSY MFG. — 556

SYSTEM
INTEGRATION — 558

CERTIFICATION
AND DELIVERY — 560

IN SERVICE — 562

MAINTENANCE
AND SERVICE — 564

566

570

AIRCRAFT

568

AIRFRAME

INTERIOR

SYSTEMS 574    576

PROPULSION    ELECTRICAL

HYDRAULIC    ENVIRON.

572    578    580

PORTABLE WAND SYSTEMS AND METHODS OF USING THE SAME TO INDICATE AND VERIFY SURFACE TREATMENT APPLICATIONS

CROSS-REFERENCE TO RELATED APPLICATION

This nonprovisional application claims priority to U.S. Provisional Application Ser. No. 63/115,010, filed Nov. 17, 2020, which is incorporated herein by reference in its entirety.

FIELD

The disclosure relates generally to systems and methods for indicating and verifying surface treatment applications, and more particularly, to systems and methods for indicating and verifying that disinfection, sanitization, and other surface treatment processes are sufficient and complete.

BACKGROUND

Manual processes for performing surface treatment applications, such as disinfecting or sanitizing surfaces, using handheld devices may have varying degrees of consistency, and repeatability may prove challenging. When a human operator performs such manual processes, it may be difficult to simultaneously maintain a high degree of quality control and efficiency. For example, manual processes using handheld ultraviolet (UV) light devices to disinfect or sanitize surfaces may require spending longer treatment times to ensure complete surface treatment to account for operator variability. Even with generous processing margin allowances, it may still not be possible to thoroughly and reliably document complete coverage manually.

In addition, it may be difficult to validate that manual processes using handheld ultraviolet (UV) light devices or applicators to disinfect or sanitize surfaces, as well as using other handheld devices or applicators, such as for UV curing, painting, shot peening, sanding, welding, and the other manual processes, have followed a prescribed or learned mode or path to perform the handheld device's or applicator's function. Known manual processes and handheld devices or applicators used with such manual processes may rely on an operator's subjective judgment as to the completeness of an operation. This may not allow for rigorous validation that the operation has been thoroughly completed.

Moreover, known manual processes and handheld devices or applicators used with such manual processes may rely on an operator's subjective judgment as to what paths or regions are to be avoided as "stay-out zones" for surface treatment application, for example, surfaces that may be affected adversely by UV light or other surface treatment applications. If the operator inadvertently aims known handheld UV light devices or applicators, or other known handheld devices or applicators, for surface treatment applications, in such "stay-out zones", such known handheld UV light devices or applicators, or other known handheld devices or applicators, do not provide an alert or indication to the operator that he or she is aimed toward the "stay-out zones", and do not provide automatic reduction or extinguishment of power of such known handheld devices or applicators.

In addition, automated methods for performing surface treatment applications, such as disinfecting or sanitizing surfaces, may require highly complex equipment that is not generally as dexterous as a human operator, when a complex surface is to be surface treated.

Accordingly, there is a need for a portable, or handheld, system and method for performing surface treatment applications, such as disinfection, sanitization, and other surface treatment processes, that indicate and verify to a user when a surface has been sufficiently treated with a manual surface treatment process using learned paths and modes, that indicate to an operator that a "stay-out zone" has been entered, that maintain a high degree of quality control and efficiency, and that provide advantages over known systems and methods.

SUMMARY

Example implementations of the present disclosure provide portable wand systems and methods of using the same to indicate and verify surface treatment applications. As discussed in the below detailed description, versions of the systems and methods may provide significant advantages over known systems and methods.

In a version of the disclosure, there is provided a portable wand system. The portable wand system comprises a wand applicator containing a surface treatment application element. The portable wand system further comprises a wand controller subsystem coupled to the wand applicator.

The wand controller subsystem comprises a computer program. The wand controller subsystem further comprises a memory unit storing a plurality of paths learned and recorded during a learn mode, by an operator manually moving the wand applicator. The plurality of paths comprises a plurality of desired paths in a plurality of stay-in zones having one or more surfaces to be surface treated with a surface treatment application of the surface treatment application element. The plurality of paths further comprises a plurality of stay-out zone paths in, or near, a plurality of stay-out zones to be avoided with the surface treatment application.

The portable wand system further comprises a selector assembly operatively coupled to a manual selector button. The portable wand system further comprises an indicator element. The portable wand system further comprises a power assembly coupled to the wand applicator.

The portable wand system is used in an operation mode after the learn mode, to measure, in real-time, the operator manually moving the wand applicator in one or more operation paths, based on one or more of the plurality of desired paths, in one or more of the plurality of stay-in zones, with the surface treatment application element activated. For a selected stay-in zone, the portable wand system compares the operation path to the desired path, and indicates to the operator when the operation path deviates from the desired path, and when the wand applicator is in proximity to, and oriented towards, one or more of the plurality of stay-out zones. The portable wand system verifies that a desired surface treatment application is achieved.

In another version of the disclosure, there is provided a method to indicate and verify that a desired surface treatment application is achieved for one or more surfaces. The method comprises the step of providing a portable wand system. The portable wand system comprises a wand applicator containing a surface treatment application element. The portable wand system further comprises a wand controller subsystem coupled to the wand applicator. The wand controller subsystem comprises a computer program, a memory unit, and a central processing unit (CPU) coupled to the memory unit. The portable wand system further comprises a selector assembly operatively coupled to a manual selector button. The portable wand system further comprises an indicator element. The portable wand system further comprises a power assembly coupled to the wand applicator.

The method further comprises the step of training the portable wand system in a learn mode, by an operator manually moving the wand applicator in a plurality of desired paths in a plurality of stay-in zones to be surface treated, and manually moving the wand applicator in a plurality of stay-out zone paths in, or near, a plurality of stay-out zones not to be surface treated. The method further comprises the step of recording and storing, with the portable wand system, the plurality of desired paths corresponding to the plurality of stay-in zones, and the plurality of stay-out zone paths corresponding to the plurality of stay-out zones.

The method further comprises the step of selecting, with the portable wand system, a selected stay-in zone having the one or more surfaces to be surface treated, and selecting the desired path corresponding to the selected stay-in zone. The method further comprises the step of operating the portable wand system in an operation mode, by the operator manually moving the wand applicator in an operation path, based on the desired path, in the selected stay-in zone, with the surface treatment application element activated The method further comprises the step of comparing, with the portable wand system, the operation path to the desired path. The method further comprises the step of indicating to the operator, with the portable wand system, when the operation path deviates from the desired path, and when the wand applicator is in proximity to, and oriented towards, one or more of the plurality of stay-out zones, to allow for adjusting movement of the wand applicator and adjusting power to the wand applicator. The method further comprises the step of verifying, with the portable wand system, that the desired surface treatment application is achieved for the one or more surfaces in the selected stay-in zone.

In another version of the disclosure, there is provided a method to indicate and verify that a desired ultraviolet (UV) light disinfection is achieved for one or more surfaces in an interior of an aircraft. The method comprises the step of providing a portable wand system. The portable wand system comprises a wand applicator containing an ultraviolet (UV) lamp element. The portable wand system further comprises a wand controller subsystem coupled to the wand applicator. The wand controller subsystem comprises a computer program, a memory unit, and a central processing unit (CPU) coupled to the memory unit. The portable wand system further comprises a selector assembly operatively coupled to a manual selector button. The portable wand system further comprises an indicator element. The portable wand system further comprises a power assembly coupled to the wand applicator.

The method further comprises the step of selecting, with the manual selector button, a learn mode selection, to activate the portable wand system in a learn mode. The method further comprises the step of training the portable wand system in a first learn mode of the learn mode, by an operator manually moving the wand applicator in a plurality of desired paths in a plurality of stay-in zones having the one or more surfaces to be disinfected with the UV lamp element. The method further comprises the step of recording and storing, with the portable wand system, the plurality of desired paths corresponding to the plurality of stay-in zones.

The method further comprises the step of training the portable wand system in a second learn mode of the learn mode, by the operator manually moving the wand applicator in one or more stay-out zone paths in, or near, a plurality of stay-out zones not to be disinfected. The method further comprises the step of recording and storing, with the portable wand system, the plurality of stay-out zone paths corresponding to the plurality of stay-out zones.

The method further comprises the step of selecting, with the manual selector button, an operation mode selection, to activate the portable wand system in an operation mode. The method further comprises the steps of selecting, with the selector assembly, a selected stay-in zone having the one or more surfaces to be disinfected, and selecting the desired path, recorded and stored in the first learn mode, and corresponding to the selected stay-in zone. The method further comprises the step of operating the portable wand system in the operation mode, by the operator manually moving the wand applicator, in real-time, in an operation path, based on the desired path, in the selected stay-in zone, with the UV lamp element activated.

The method further comprises the step of comparing, with the portable wand system, the operation path to the desired path. The method further comprises the step of indicating to the operator, with the portable wand system, when the operation path deviates from the desired path, and when the wand applicator is in proximity to, and oriented towards, one or more of the plurality of stay-out zones, to allow for adjusting movement of the wand applicator and adjusting power to the UV lamp element. The method further comprises the step of verifying, with the portable wand system, that the desired UV light disinfection is achieved for the one or more surfaces in the selected stay-in zone.

The features, functions, and advantages that have been discussed can be achieved independently in various versions of the disclosure or may be combined in yet other versions further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary versions, but which are not necessarily drawn to scale. The drawings are examples and not meant as limitations on the description or claims.

FIG. 1A is an illustration of a functional block diagram showing exemplary versions of a portable wand system of the disclosure;

FIG. 1B is an illustration of a functional block diagram showing exemplary versions of surfaces, surface treatment applications, and surface treatment application elements used with exemplary versions of a portable wand system of the disclosure;

FIG. 1C is an illustration of a functional block diagram showing exemplary versions of a portable wand system of the disclosure for use in a learn mode and an operation mode;

FIG. 7 is an illustration of a flow diagram of a version of a method of the disclosure;

FIG. 8 is an illustration of a flow diagram of a version of another method of the disclosure;

Figure 2A:
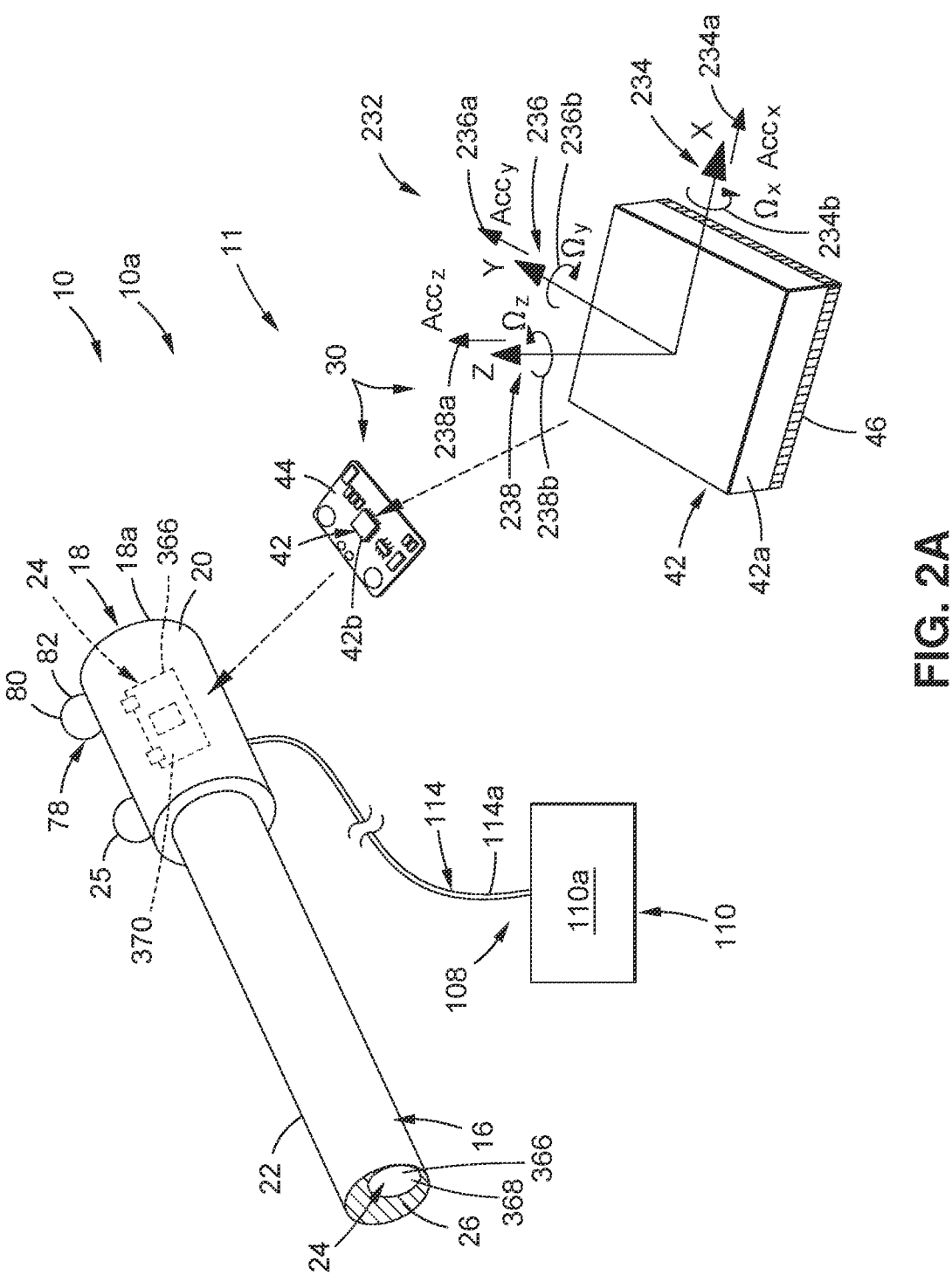
FIG. 2A is an illustration of a perspective view of a version of a portable wand system of the disclosure with a binary indicator and an RFID reader and RFID electronics.

The figures shown in this disclosure represent various aspects of the versions presented, and only differences will be discussed in detail.

DETAILED DESCRIPTION

Disclosed versions or embodiments will now be described more fully hereinafter with reference to the accompanying drawings, in which some, but not all of the disclosed versions are shown. Indeed, several different versions may be provided and should not be construed as limited to the versions set forth herein. Rather, these versions are provided so that this disclosure will be thorough and fully convey the scope of the disclosure to those skilled in the art.

This specification includes references to "one version" or "a version". The instances of the phrases "in one version" or "in a version" do not necessarily refer to the same version. Particular features, structures, or characteristics may be combined in any suitable manner consistent with this disclosure.

As used herein, "comprising" is an open-ended term, and as used in the claims, this term does not foreclose additional structures or steps.

As used herein, "designed to" or "configured to" means various parts or components may be described or claimed as "designed to" or "configured to" perform a task or tasks. In such contexts, "designed to" or "configured to" is used to connote structure by indicating that the parts or components include structure that performs those task or tasks during operation. As such, the parts or components can be said to be configured to perform the task even when the specified part or component is not currently operational (e.g., is not on).

As used herein, the terms "first", "second", etc., are used as labels for nouns that they precede, and do not imply any type of ordering (e.g., spatial, temporal, logical, etc.).

As used herein, an element or step recited in the singular and preceded by the word "a" or "an" should be understood as not necessarily excluding the plural of the elements or steps.

Now referring to the Figures, FIG. 1A is an illustration of a functional block diagram showing exemplary versions of a portable wand system 10 of the disclosure. FIG. 1B is an illustration of a functional block diagram showing exemplary versions of surfaces 12, surface treatment applications 14, and surface treatment application elements (STAE) 16 used with exemplary versions of the portable wand system 10 of the disclosure. FIG. 1C is an illustration of a functional block diagram showing exemplary versions of the portable wand system 10 of the disclosure, including a trainable portable wand system 11 trained and used in a learn mode 300, and that once trained with the learn mode 300, becomes a trained portable wand system Ila that is used in an operation mode 302.

The blocks in FIGS. 1A-1C represent elements, and lines connecting the various blocks do not imply any particular dependency of the elements. Furthermore, the connecting lines shown in the various Figures contained herein are intended to represent example functional relationships and/or physical couplings between the various elements, but it is noted that other alternative or additional functional relationships or physical connections may be present in versions disclosed herein.

The portable wand system 10 is a mobile applicator system used to manually surface treat one or more surfaces 12 with a surface treatment application 14. The portable wand system 10 indicates, verifies, and validates that the correct, complete, and thorough application of the surface treatment application 14, such as an ultraviolet (UV) light disinfection operation 170 (see FIG. 1B), onto one or more surfaces 12 of an area or object, has been achieved. The portable wand system 10 also allows a user 52 (see FIG. 1A), for example, an operator 54 (see FIG. 1A), to self-verify that the surface treatment application 14 has been sufficiently performed and completed. The one or more surfaces 12 designed to be are surface treated, and that are surface treated, are preferably in an interior 146, as shown in FIG. 1B, of one of, an aircraft 148, a spacecraft 150, an automotive vehicle 152, a watercraft 154, a train 156, a hospital 158, a factory building 160, an office building 162, a movie theater 164, a restaurant 166, or another suitable vehicle or structure.

In a version of the disclosure, there is provided the portable wand system 10 (see FIGS. 1A, 1C), including the trainable portable wand system 11 (see FIG. 1C), and the trained portable wand system 11a (see FIG. 1C). As shown in FIG. 1A, the portable wand system 10 comprises a wand applicator 18. Preferably, the wand applicator 18 is a hand-held wand applicator 18a (see FIG. 1A) that is manually used by the user 52 (see FIG. 1A), the operator 54 (see FIG. 1A), or an inspector 56 (see FIG. 1A). The wand applicator 18 has a handle portion 20 (see FIG. 1A) and a head portion 22 (see FIG. 1A). The portable wand system 10 further comprises a selector assembly 24 (see FIGS. 1A, 1C), discussed in further detail below, and a manual selector button 25 (see FIG. 1A), or user input button. The selector assembly 24 is operatively coupled to, or activated by, the manual selector button 25 (see FIG. 1A), or user input button. In one version, the manual selector button 25 is coupled to the wand applicator 18, for example, the manual selector button 25 is coupled to, or integrated in, the handle portion 20 of the wand applicator 18. In other versions, the manual selector button 25 is coupled to an energy storage device 110 (see FIGS. 1A, 2A) of a power assembly 108 (see FIGS. 1A, 2A), or is coupled to a system case 122 (see FIGS. 1, 5A) that houses or holds the portable wand system 10.

The wand applicator 18, and in particular, the head portion 22 of the wand applicator 18, contains a surface treatment application element (STAE) 16 (see FIG. 1A). In a preferred version, the surface treatment application element (STAE) 16 comprises an ultraviolet (UV) lamp element 26 (see FIG. 1A). The UV lamp element 26 is operable, or configured, to emit an ultraviolet (UV) light 28 (see FIG. 1A) having a wavelength in a range between 200 nm (nanometers) to 280 nm (nanometers), to sufficiently disinfect the one or more surfaces 12. More preferably, the UV lamp element 26 comprises a 222 nm (nanometer) UV lamp element 26a (see FIG. 1A), where the UV lamp element 26 is operable, or configured, to emit the UV light 28 having a wavelength of 222 nanometers. Other versions of the surface treatment application element (STAE) 16 are discussed below with respect to FIG. 1B.

The UV light 28 used is preferably ultraviolet C (UVC) light that is short-wave and germicidal, and can emit sanitizing UV light 28. It has been found that sanitizing UV light having a wavelength of 222 nm (nanometers) kills or deactivates pathogens, such as viruses and bacteria, and is safe for human exposure. Further, the sanitizing UV light 28 having a wavelength of 222 nm may be emitted at full power within one millisecond, or less, of the UV lamp element 26 being activated.

As shown in FIG. 1A, the portable wand system 10 further comprises a wand controller subsystem 30 coupled to the wand applicator 18, either wired or wirelessly. As shown in FIG. 1A, the wand controller subsystem 30 comprises a computer program 32, such as an algorithm 32a.

As shown in FIG. 1A, the wand controller subsystem 30 further comprises a central processing unit (CPU) 60 and a memory unit 66. The memory unit 66 is coupled to the CPU 60. The memory unit 66 stores data 68 (see FIG. 1A) measured by the portable wand system 10, including positional data 58 measured by an inertial measurement unit (IMU) 42 (see FIG. 1A).

As shown in FIG. 1C, the memory unit 66 is designed to store, and stores, data 68, including a plurality of paths 304, or patterns 306, learned and recorded during a learn mode

300, by the user 52, or operator 54, such as a designated trainer, manually moving the portable wand system 10, for example, the trainable portable wand system 11, in, over, or near a plurality of zones 308 to be surface treated, or not to be surface treated. The plurality of paths 304 may also be referred to as learned paths 304a (see FIG. 1C), or preprogrammed paths, or tool paths. As shown in FIG. 1C, the plurality of paths 304 comprise a plurality of desired paths 310, such as first learned paths 310a. As further shown in FIG. 1C, the plurality of paths 304, such as the learned paths 304a, further comprise a plurality of stay-out zone paths 312, such as second learned paths 312a.

The plurality of zones 308 comprise a plurality of stay-in zones 314 (see FIG. 1C) having one or more surfaces 12 (see FIG. 1A) to be surface treated with a surface treatment application 14 (see FIG. 1A) of the surface treatment application element 16 (see FIG. 1A). Examples of stay-in zones 314 in an aircraft 148 (see FIG. 1B) or aircraft 500a (see FIG. 9) to be surface treated with the surface treatment application 14, such as UV light disinfection 172 (see FIG. 1B), using the portable wand system 10 may include stay-in zones 314 in a flight deck 315 (see FIG. 4B), or a flight deck 506 (see FIG. 9), such as flight deck control areas 316 (see FIG. 4B), flight deck seats 318 (see FIG. 4B), flight deck panel areas 320 (see FIG. 4B), a flight deck floor 322 (see FIG. 4B), a flight deck ceiling 324 (see FIG. 4B), or other suitable flight deck areas. Examples of stay-in zones 314 in an aircraft 148 (see FIG. 1B), or an aircraft 500a (see FIG. 9), to be surface treated with the surface treatment application 14, such as UV light disinfection 172 (see FIG. 1B), using the portable wand system 10 may further include stay-in zones 314 in a cabin 246 (see FIGS. 4A, 4C), such as cabin seats 248 (see FIGS. 4A, 4C), a cabin floor 326 (see FIG. 4C), a cabin ceiling 327 (see FIG. 4C), passenger service units 328 (see FIG. 4C), monitors 329 (see FIG. 4C), overhead stowage bins 330 (see FIG. 4C), cabin panel areas 331 (see FIG. 4C), or other suitable cabin areas. Other areas or regions in the aircraft 148 to be surface treated with the portable wand system 10 may also be designated as stay-in zones 314. As used herein, "stay-in zone" means a zone, area, or region of a vehicle, such as an aircraft or other vehicle, or a structure, that has one or more surfaces designed to be surface treated, and are surface treated, with a surface treatment application 14 (see FIG. 1B) applied using the portable wand system 10 (see FIGS. 1A, 1C) disclosed herein.

The plurality of zones 308 further comprise a plurality of stay-out zones 332 (see FIG. 1C) to be avoided with the surface treatment application 14, and not to be surface treated with the surface treatment application 14, for example, surfaces that may be adversely affected by UV light 28 or other surface treatment applications. Examples of stay-out zones 332 in an aircraft 148 (see FIG. 1B), or aircraft 500a (see FIG. 9), not to be surface treated, and to be avoided with the surface treatment application 14 of the portable wand system 10, may include flight deck windows 334 (see FIG. 4B) in the flight deck 315, or in the flight deck 506 (see FIG. 9), cabin windows 335 (see FIGS. 4A, 4C) in the cabin 246 (see FIGS. 4A, 4C), or other areas or regions in the aircraft 148 (see FIG. 1B) or aircraft 500a (see FIG. 9) not to be surface treated with the portable wand system 10 and designated as stay-out zones 332. As used herein, "stay-out zone" means a zone, area, or region of a vehicle, such as an aircraft or other vehicle, or a structure, that has one or more surfaces designed not to be surface treated, and are not surface treated, and are to be avoided, with a surface treatment application 14 (see FIG. 1B) applied using the portable wand system 10 (see FIGS. 1A, 1C) disclosed herein, to avoid adversely affecting one or more surfaces in such zone, area, or region.

As shown in FIG. 1C, the portable wand system 10, for example, the trainable portable wand system 11, is designed to be trained, learned, or preprogrammed, by the user 52, or operator 54, for example, the designated trainer, in the learn mode 300. FIG. 1C shows the learn mode 300, or preprogramming mode, comprising a first learn mode 300a, or first preprogramming mode, and a second learn mode 300b, or second preprogramming mode. Prior to training the portable wand system 10, for example, the trainable portable wand system 11, in the learn mode 300, the portable wand system 10, for example, the trainable portable wand system 11, may be activated to enter the learn mode 300.

The manual selector button 25 functions by being pressed by the user 52, or operator 54, in a single click, or a sequence of clicks or patterns, depending on what function is desired. For example, the manual selector button 25 may be pressed with a single click to "zero out" the position of the wand applicator 18 to a home position 336 (see FIG. 1C). Further, the manual selector button 25 may be pressed with a double click, or another suitable pattern or sequence of clicks, to enter a selection mode 338 (see FIG. 1C).

The selection mode 338 allows for selection, with the manual selector button 25, of a plurality of mode selections 340 (see FIG. 1C) that may be selected depending on what function the portable wand system 10 will be performing. As shown in FIG. 1C, the plurality of mode selections 340 include a learn mode selection 342 and an operation mode selection 344. The plurality of mode selections 340 may also include other suitable mode selections. The learn mode selection 342 may further include the selection of a stay-in zone learn mode selection 342a (see FIG. 1C), for activating or entering training of the portable wand system 10 in the first learn mode 300a in the stay-in zones 314. The learn mode selection 342 may further include the selection of a stay-out zone learn mode selection 342b (see FIG. 1C), for training the portable wand system 10 in the second learn mode 300b in the stay-out zones 332. The mode selections 340 may have LED (light-emitting diode) color indicators to assist the user 52 to know which mode has been selected.

Thus, the user 52, or operator 54, for example, the designated trainer, may enter the selection mode 338 by selecting, or pressing, the manual selector button 25 with a double click, or other suitable sequence of clicks or patterns, and then select, with the manual selector button 25, the learn mode selection 342, to activate the portable wand system 10, for example, the trainable portable wand system 11, to enter the learn mode 300. The user 52, or operator 54, for example, the designated trainer, may then select, with the manual selector button 25, the stay-in zone learn mode selection 342a, or the stay-out zone learn mode selection 342b.

After the learn mode 300 is complete, the user 52, or operator 54, may press the manual selector button 25 with a single click to "zero out" the position of the wand applicator 18 to the home position 336 (see FIG. 1C). Subsequently, the user 52, or operator 54, may enter the selection mode 338 by selecting, or pressing, the manual selector button 25 with a double click, or other suitable sequence of clicks or pattern, and then select, with the manual selector button 25, the operation mode selection 344 to activate the portable wand system 10, for example, the trainable portable wand system 11, to enter the operation mode 302.

The manual selector button 25 may also allow for selection of a plurality of zone selections 346 (see FIG. 1C), including one or more stay-in zone selections 346a (see FIG. 1C) and one or more stay-out zone selections 346b (see FIG. 1C). Once the portable wand system 10, for example, the trainable portable wand system 11, is activated to the learn mode 300, a desired zone 308a (see FIG. 1C) may be selected with the manual selector button 25, and the selector assembly 24, in one of the versions, discussed below, may be used. A selected stay-in zone 314a may be selected or chosen by selecting or pressing the stay-in zone selection 346a with the manual selector button 25. Alternatively, a selected stay-in zone 314a may be initially selected or chosen before the learn mode selection 342 is chosen or selected. In addition, a selected stay-out zone 332a may be selected or chosen by selecting or pressing the stay-out zone selection 346b with the manual selector button 25. Alternatively, a selected stay-out zone 332a may be initially selected or chosen before the learn mode selection 342 is chosen or selected.

The portable wand system 10, for example, the trainable portable wand system 11, is trained in the learn mode 300, such as the first learn mode 300a, by the operator 54, or user 52, for example, the designated trainer, manually moving the wand applicator 18 in the plurality of desired paths 310 in the plurality of stay-in zones 314 having the one or more surfaces 12 to be surface treated with the surface treatment application element 16. For example, a selected stay-in zone 314a may be selected in the learn mode 300, and the operator 54, or user 52, for example, the designated trainer, manually moves, or manipulates, the wand applicator 18 of the portable wand system 10, such as the trainable portable wand system 11, in a desired path 310 within the selected stay-in zone 314a. A desired path 310 corresponds to a selected stay-in zone 314a. Each desired path 310 of the plurality of desired paths 310 corresponding to the selected stay-in zone 314a of the plurality of stay-in zones 314, is recorded, in real-time, with the CPU 60 of the wand controller subsystem 30 of the portable wand system 10, and stored, in real-time, in the memory unit 66 of the wand controller subsystem 30 of the portable wand system 10. Prior to manually moving the wand applicator 18 in the first learn mode 300a, in the plurality of desired paths 310 in the plurality of stay-in zones 314, the stay-in zone learn mode selection 342a may be selected with the manual selector button 25. The portable wand system 10 is preferably trained by manually moving the wand applicator 18 in the plurality of desired paths 310 in the plurality of stay-in zones 314 with the surface treatment application element 16, such as the ultraviolet (UV) lamp element 26, turned off. However, the portable wand system 10 may also be trained with the surface treatment application element 16, such as the ultraviolet (UV) lamp element 26, turned on.

The desired path 310, or desired paths 310, may be learned or trained during the learn mode 300, such as the first learn mode 300a, by manually moving the wand applicator 18, such as positioning, orienting, and manipulating the wand applicator 18 in, or over, the interior of a stay-in zone 314, such as a selected stay-in zone 314a, or in another suitable manual movement of the wand applicator 18 with respect to the stay-in zone 314.

The portable wand system 10, for example, the trainable portable wand system 11, is trained in the learn mode 300, such as the second learn mode 300b, by the operator 54, or user 52, for example, the designated trainer, manually moving the wand applicator 18 in one or more stay-out zone paths 312 in, over, or near the plurality of stay-out zones 332 to be avoided and not to be surface treated. For example, a selected stay-out zone 332a may be selected in the learn mode 300, such as the second learn mode 300b, and the user 52, or operator 54, for example, the designated trainer, manually moves, or manipulates, the wand applicator 18 of the portable wand system 10, such as the trainable portable wand system 11, in a stay-out zone path 312 in, over, or near a stay-out zone 332. A stay-out zone path 312 corresponds to one or more selected stay-out zones 332a. Each stay-out zone path 312 of the plurality of stay-out zone paths 312 corresponding to the one or more selected stay-out zones 332a of the plurality of stay-out zones 332, is recorded, in real-time, with the CPU 60 of the wand controller subsystem 30 of the portable wand system 10, and stored, in real-time, in the memory unit 66 of the wand controller subsystem 30 of the portable wand system 10. Prior to manually moving the wand applicator 18 in the second learn mode 300b, in the plurality of stay-out zone paths 312 in, over, or near, the plurality of stay-out zones 332, the stay-out zone learn mode selection 342b may be selected with the manual selector button 25.

The stay-out zone paths 312 may be learned or trained during the learn mode 300, such as the second learn mode 300b, by manually moving the wand applicator 18, such as positioning, orienting, and manipulating the wand applicator 18 in, or over, the interior of a stay-out zone 332, near the interior or exterior of the stay-out zone 332, around the perimeter of one or more stay-out zones 332, for example, stay-out zones 332 that are adjacent to each other, tapping the corners of one or more stay-out zones 332, or another suitable manual movement of the wand applicator 18 with respect to the one or more stay-out zones 332. Further, the stay-out zone 332 may also be created directly via a selection on a menu, e.g. create stay-out zone, or indirectly, by a selection that allows the wand applicator 18 to scan in those zone 308 that have been set up as stay-in zones 314. The portable wand system 10 is trained by manually moving the wand applicator 18 in the plurality of stay-out zone paths 312 in, over, or near the plurality of stay-out zones 332 with the surface treatment application element 16, such as the ultraviolet (UV) lamp element 26, turned off.

The plurality of desired paths 310 corresponding, respectively, to the plurality of stay-in zones 314, that are recorded by the CPU 60 and stored in the memory unit 66, as well as the plurality of stay-out zone paths 312 corresponding, respectively, to the plurality of stay-out zones 332, that are recorded by the CPU 60 and stored in the memory unit 66, may be developed or made into a depiction 34 (see FIG. 1A), such as a geometric model 36 (see FIG. 1A). The geometric model 36 may comprise a CAD (computer-aided design) model, or another type of computer model, or a map, of the recorded and stored desired paths 310 corresponding, respectively, to the plurality of stay-in zones 314, and of the recorded and stored stay-out zone paths 312 corresponding, respectively, to the plurality of stay-out zones 332. The zones 308, such as the stay-in zones 314 with the desired paths 310, and the stay-out zones 332 with the stay-out zone paths 312, may be identified in the geometric model 36.

In another version, the depiction 34 may comprise a photographic image 38 (see FIG. 1A) obtained with a photogrammetric process 40 (see FIG. 1A), that records and stores the plurality of desired paths 310 corresponding, respectively, to the plurality of stay-in zones 314, and the plurality of stay-out zone paths 312 corresponding, respectively, to the plurality of stay-out zones 332.

As shown in FIG. 1A, the wand controller subsystem 30 may further comprise the inertial measurement unit (IMU) 42. Preferably, the IMU 42 comprises a 6 degrees of freedom inertial measurement unit (IMU) 42a (see FIG. 1A). As used herein, "6 degrees of freedom" means a freedom of movement in a three-dimensional space, where an object is free to change position as forward/backward, up/down, left/right translation in three perpendicular axes, combined with changes in orientation through rotation about three perpendicular axes, for example, yaw (normal axis), pitch (transverse axis), and roll (longitudinal axis).

The IMU 42 comprises an integrated circuit (IC) 42b (see FIGS. 1A, 2A-2B) or chip, mounted on a circuit board 44 (see FIGS. 2A-2B), and comprises an accelerometer 46 (see FIG. 1A) to measure an acceleration 48 (see FIG. 1A) of the wand applicator 18. The IMU 42 further measures one or more positions 50 (see FIG. 1A) of the wand applicator 18, as it is moved by a user 52 (see FIG. 1A), or an operator 54 (see FIG. 1A), for example, a designated trainer, or an inspector 56 (see FIG. 1A), over the one or more surfaces 12 to be surface treated. The IMU 42 sends positional data 58 of movement 388 (see FIG. 1C) of the wand applicator 18 to the CPU 60 coupled to the IMU 42.

The wand controller subsystem 30 may further comprise a surface treatment application element (STAE) power feedback 62 (see FIG. 1A) to the CPU 60. In a preferred version, where the portable wand system 10 includes the UV lamp element 26, the wand controller subsystem 30 further comprises an ultraviolet (UV) lamp element power feedback 64 (see FIG. 1A) to the CPU 60. As shown in FIG. 1A, the wand controller subsystem 30 may further optionally comprise a wireless network interface 70 coupled to the CPU 60.

As an alternative to using the IMU 42 in the wand controller subsystem 30, the wand controller subsystem 30 may comprise separately, or in combination, one or more of, a fixed position extensometer 72 (see FIG. 1A), a rotary position sensor 74 (see FIG. 1A), and/or an external photogrammetric sensor 76 (see FIG. 1A). The fixed position extensometer 72 measures the elongation of a material under stress, and may also be used to determine yield strength, tensile strength, yield point elongation, strain-hardening exponent, and strain ratio. The rotary position sensor 74 measures rotational angles from output voltages and translates angular mechanical position to an electrical signal. The external photogrammetric sensor 76 records, measures, and interprets photographic images and patterns of electromagnetic radiant imagery and generates two-dimensional and three-dimensional digital models of the surface, area, or object as an end product.

As shown in FIG. 1A, the portable wand system 10 further comprises an indicator element 78. In one version, the indicator element 78 comprises a binary indicator 80 (see FIG. 1A), or on/off indicator. As shown in FIG. 1A, the binary indicator 80 comprises one of, a light signal 82 coupled to the wand applicator 18, a surface treatment application element (STAE) flashing light alert 84, such as an ultraviolet (UV) flashing light alert 84a, an audio alert 86, a sound alert 88, a tactile alert 90, a vibration alert 92, a pulsing alert 94, a pressure altering alert 96, or another suitable binary indicator, to indicate that the surface treatment application 14 of one or more of the one or more surfaces 12 is complete, and also indicates when the wand applicator 18 is in an incorrect position 392 (see FIG. 1C), and/or is in proximity to, and oriented towards, one or more of the plurality of stay-out zones 332. The audio alert 86, or the sound alert 88, may comprise an audible bell, chime, beep, voice, or other sound or noise. The binary indicator 80 indicates that the surface treatment application 14, such as the predetermined surface treatment application 14a, of a sub-area, or one or more of the surfaces 12, is complete, and it is acceptable to continue to the next sub-area or surface 12, and also indicates when the wand applicator 18 is in the incorrect position 392 (see FIG. 1C), and/or is in proximity to, and oriented towards, one or more of the plurality of stay-out zones 332.

As an alternative to the binary indicator 80, or in addition to the binary indicator 80, the portable wand system 10 may comprise a video display 98, such as a video progress display 98a, coupled to the wand applicator 18. In one version, the video display 98 may be coupled to the wand applicator 18, via a connector element 100 (see FIG. 1A), such as a wired interconnect cable, or a wireless connection. In another version, the video display 98 may be incorporated on the wand applicator 18. The video display 98 may comprise a handheld tablet computer coupled to the wand applicator 18, via the connector element 100, or may comprise a screen display incorporated on the wand applicator 18, or may comprise another suitable video display device. The video display 98 is visible to the user 52, or operator 54, and shows one or more of, portions 102 (see FIG. 1A) of the one or more surfaces 12 to be surface treated, and a color coded signal 104 (see FIG. 1A), comprising a lighted progress bar 106 (see FIG. 1A), or map, to indicate which portions 102 have complete coverage, such as complete coverage portions 102a (see FIG. 1A).

As shown in FIG. 1A, the portable wand system 10 further comprises a power assembly 108 coupled to the wand controller subsystem 30. As shown in FIG. 1A, the power assembly 108 comprises an energy storage device 110 coupled to a power connector 112. As shown in FIG. 1A, the energy storage device 110 may comprise one or more batteries 110a, or another suitable energy storage device. The power connector 112 may comprise a wired connector 114 (see FIG. 1A), such as a power interconnect cable 114a (see FIG. 1A), a power cord 114b (see FIG. 1A), a high voltage cable 114c (see FIG. 1A), LED (light-emitting diode) wiring 114d (see FIG. 1A), or another suitable wired connector. The power connector 112 may further comprise a wireless connector 116 (see FIG. 1A).

As shown in FIG. 1A, the power assembly 108 may further comprise a power supply 117, such as a surface treatment application element (STAE) power supply 118, for example, a UV lamp element power supply 120, or another suitable power supply for a surface treatment application element 16. The power supply 117 provides power 121 (see FIG. 1A) to the surface treatment application element 16, such as a UV lamp element 26, of the wand applicator 18 or the portable wand system 10.

As shown in FIG. 1C, the selector assembly 24 of the portable wand system 10, for example, the trainable portable wand system 11, and the trained portable wand system 11a, may comprise one of a number of various versions. Versions of the selector assembly 24 are preferably operatively coupled to, and activated by, the manual selector button 25. As discussed above, the manual selector button 25, activates the selector assembly 24 by being pressed by the user 52, or operator 54, in a single click, or a sequence of clicks or patterns, depending on what function is desired. The manual selector button 25 is designed to select the home position 336, and is designed to select the selection mode 338. The selection mode 338 allows for selection of mode selections 340 (see FIG. 1C), such as the learn mode selection 342, or the operation mode selection 344, depending on what function the portable wand system 10 will be performing. The manual selector button 25 allows the user 52, or operator 54, to also select from the plurality of zone selections 346, including the stay-in zone selections 346a and the stay-out zone selections 346b.

In one version, as shown in FIG. 1C, the selector assembly 24 comprises a barcode assembly 348 operatively coupled to, and activated by, the manual selector button 25 coupled to the wand applicator 18. As shown in FIG. 1C, the barcode assembly 348 comprises a barcode camera 350, or barcode reader, coupled to the wand applicator 18, such as coupled to the head portion 22 of the wand applicator 18. The manual selector button 25 may activate the barcode camera 350 with a sequence of clicks or a pattern, for example, with a double click or another suitable sequence of clicks or patterns, for example, by the user 52, or operator 54, double clicking the manual selector button 25, or double clicking the manual selector button 25 in the form of a trigger handle 284 (see FIG. 6A).

As shown in FIG. 1C, the barcode assembly 348 further comprises decoder electronics 352. The decoder electronics 352 may be coupled to the wand applicator 18, such as coupled to the handle portion 20 of the wand applicator 18, or coupled to the barcode camera 350 itself. The barcode camera 350 is designed to read one or more barcodes 354 (see FIG. 1C) located in one or more of the plurality of stay-in zones 314 and located in one or more of the plurality of stay-out zones 332. The barcode assembly 348 selects the one or more selected stay-in zones 314a and the one or more selected stay-out zones 332a during the learn mode 300, and selects the selected stay-in zone 314a and a selected desired path 310b (see FIG. 1C) corresponding to the selected stay-in zone 314a during the operation mode 302.

The barcode camera 350, or barcode reader, may comprise, in one version, a two-dimensional imaging scanner 350a (see FIG. 1C) that uses a camera and decoder electronics 352 to decode the barcode 354. The barcode camera 350 is designed to read, and reads, a barcode 354, such as a two-dimensional barcode 354a (see FIG. 1C), for example, a QR (Quick Response) code 354b (see FIG. 1C), or another suitable barcode. The QR code 354b may consist of black squares arranged in a square grid on a white background, which can be read by an imaging device, such as the barcode camera 350, and then processed until the image is appropriately interpreted and defined. The required data is then extracted from patterns that are present in both horizontal and vertical components of the image.

In one version, the barcode camera 350 is designed to read, and reads, the barcode 354, such as the two-dimensional barcode 354a, printed on a paper 356 (see FIG. 1C) comprising operator work instructions 358 (see FIG. 1C) for the surface treatment application 14 desired to be used in each zone 308. In another version, the barcode camera 350 is designed to read, and reads, a barcode 354, such as a two-dimensional barcode 354a, printed on an adjacent surface 360 (see FIG. 1C) adjacent to the one or more surfaces 12 to be surface treated with the surface treatment application 14. The two-dimensional barcode 354a may be printed or applied directly, or indirectly, to the adjacent surface 360, for example, on a label, a decal, or a sticker applied to the adjacent surface 360. The barcode 354 is a machine-readable optical image or label that contains information about the item to which it is attached, such as the selected stay-in zone 314a and the corresponding desired path 310, and such as the selected stay-out zone 332a and the corresponding stay-out zone path 312.

The barcode camera 350 is designed to read, and reads, the barcode 354, and the decoder electronics 352 are designed to decode the data contained in the barcode 354, and send the data to a computing device, such as the CPU 60. The decoder electronics 352 comprise decoder circuitry that can analyze the barcode's image data provided by the barcode camera 350, or barcode reader, or a sensor, that sends the barcode's content to the computing device, such as the CPU 60. Multiple desired paths 310 and stay-out zone paths 312 may be stored, and selected from the memory unit 66 coupled to the CPU 60 of the wand controller subsystem 30, using the barcodes 354, such as QR codes 354*b*, located in the corresponding stay-in zones 314 and the corresponding stay-out zones 332, or printed on operator work instructions 358 that the operator 54, or user 52, may scan with the barcode camera 350, or barcode reader, on the wand applicator 18, or that the operator 54, or user 52, may scan on a separate mobile device 362 (see FIG. 1C) that communicates with the portable wand system 10 to recall the desired path 310, or preferred path, for that zone 308, such as the selected stay-in zone 314*a* or the selected stay-out zone 332*a*. The barcode assembly 348, including the barcode camera 350 and the decoder electronics 352, is operatively coupled to the CPU 60 to select the zone 308, such as the stay-in zone 314, to be surface treated, such as disinfected, and to select the zone 308, such as the stay-out zone 332, not to be surface treated.

The barcode camera 350, or barcode reader, may comprise, in another version, an optical scanner 364 (see FIG. 1C) having a light source, a lens, and a light sensor that translates optical impulses into electrical signals. The optical scanner 364 is designed to read, and reads, a barcode 354 located in one or more of the plurality of stay-in zones 314, located in one or more of the plurality of stay-out zones 332, printed on the paper 356 comprising operator work instructions 358, or printed on the adjacent surface 360 adjacent to the one or more surfaces 12 to be surface treated with the surface treatment application 14. The optical scanner 364 decodes, with the decoder electronics 352, the data contained in the barcode 354, and sends the data to the computing device, such as the CPU 60.

In another version, as shown in FIG. 1C, the selector assembly 24 comprises a radio frequency identification (RFID) assembly 366 operatively coupled to, and activated by, the manual selector button 25 coupled to the wand applicator 18. As shown in FIG. 1C, the RFID assembly 366 comprises a radio frequency identification (RFID) reader 368 coupled to the wand applicator 18, such as coupled to the head portion 22 of the wand applicator 18. The manual selector button 25 may activate the RFID reader 368 with a sequence of clicks or a pattern, for example, with a double click or another suitable sequence of clicks or patterns, for example, by the user 52, or the operator 54, double clicking the manual selector button 25, or double clicking the manual selector button 25 in the form of a trigger handle 284 (see FIG. 6A).

As shown in FIG. 1C, the RFID assembly 366 further comprises radio frequency identification (RFID) electronics 370 and radio frequency identification (RFID) tags 372. The RFID electronics 370 may be coupled to the wand applicator 18, such as coupled to the handle portion 20 of the wand applicator 18. The RFID reader 368 is designed to read, and reads, one or more of the RFID tags 372 located in one or more of the plurality of stay-in zones 314 and located in one or more of the plurality of stay-out zones 332. The RFID reader 368 and the RFID electronics 370 are operatively coupled to the CPU 60 of the wand controller subsystem 30, and are used with the RFID tags 372, to identify and select one or more zones 308, such as one or more stay-in zones 314, to be surface treated, such as disinfected, and to identify and select one or more zones 308, such as one or more stay-out zones 332, not to be surface treated.

In the learn mode 300, the RFID reader 368 reads the RFID tags 372 located on or at the various zones 308, such as the stay-in zones 314 and the stay-out zones 332, and the RFID reader 368 finds each zone 308 by the RFID tag 372 in that zone 308. The RFID tags 372 may be used to help the inertial measurement unit (IMU) 42 (see FIG. 1A) know where the position 50 (see FIG. 1A) of the wand applicator 18 is located, and may help to prevent drift of the position 50 of the wand applicator 18. In the operation mode 302, with the RFID reader 368, the stay-out zones 332 may already be mapped, recorded, and stored in the memory unit 66, and it may not be necessary to scan the stay-out zones 332 to have the wand applicator 18 remember to turn off the power 121 (see FIG. 1A), or reduce the power 121, of the wand applicator 18, and in particular, of the surface treatment application element 16, or UV lamp element 26, if the wand applicator 18 inadvertently enters or nears the stay-out zone 332, or points in the direction of the stay-out zone 332.

The RFID reader 368 and RFID electronics 370 use electromagnetic fields and low power radio waves to automatically identify and track the RFID tags 372 attached to, or embedded within, the zones 308, such as the stay-in zones 314 and the stay-out zones 332, for example, attached to, or embedded within, objects or surfaces within the zones 308. When triggered by an electromagnetic interrogation pulse or radio wave from the RFID reader 368, the RFID tag 372 transmits digital data, for example, an identifier 373 (see FIG. 1C), such as an identifying number, back to the RFID reader 368. The identifier 373, such as the identifying number, may be used to identify and select a desired zone 308*a*, such as a selected stay-in zone 314*a*, or a selected stay-out zone 332*a*. The RFID tags 372 may comprise electronic tags, labels, stickers, or the like, that transfer data to the RFID reader 368 via radio waves. The RFID tags 372 contain antennas to enable them to receive and respond to radio frequency requests from the RFID reader 368, or transceiver. The RFID tags 372 may be uniquely identified by a WiFi-based wireless infrastructure. The RFID tag 372 preferably comprises a passive RFID tag 372*a* (see FIG. 1C) powered by energy from interrogating radio waves of the RFID reader 368 and activated by the RFID reader 368 being nearby, rather than an active RFID tag that requires an internal power supply, typically a small battery.

In another version, as shown in FIG. 1C, the selector assembly 24 comprises a manual selector assembly 374 comprising a manual selection device 376 coupled to the wand applicator 18, and a preprogrammed list 378, or reference list, of identifiers 373, such as identifying numbers, corresponding to the plurality of stay-in zones 314 and corresponding to the plurality of stay-out zones 332. The manual selector button 25 may activate, or facilitate activating, or using, the manual selection device 376.

In one version, the manual selection device 376 comprises a selection element 380 (see FIG. 1C), such as a series of buttons 380*a* (see FIG. 1C) on the wand applicator 18 that are manually pressed by the operator 54, or user 52, or a touchscreen 380*b* on the wand applicator 18 that is touched by the operator 54, or user 52, to input identifiers 373 (see FIG. 1C), or another suitable selection element 380 on the wand applicator 18, such as on the handle portion 20 of the wand applicator 18. The series of buttons 380*a* or the touchscreen 380*b* may include up/down arrow buttons, or a scroll bar, or another suitable selection mechanism to select the identifiers 373 from the preprogrammed list 378. The identifiers 373 may include numeric inputs, such as identifying numbers or serial numbers, alphanumeric characters or inputs, letter inputs such as names, code names, or descriptors, or other suitable identifiers for the zones 308, such as the plurality of stay-in zones 314 and the plurality of stay-out zones 332, and/or for the desired paths 310 and the stay-out zone paths 312. The selection element 380 is preferably used by the user 52, or operator 54, to identify and select an identifier 373 from the preprogrammed list 378, that is associated with, or corresponds to, a desired zone 308a, for example, a selected stay-in zone 314a, or a selected stay-out zone 332a, and to recall from the memory unit 66 the selected desired path 310b (see FIG. 1C) associated with the selected stay-in zone 314a and/or the selected stay-out zone path 312b (see FIG. 1C) associated with the one or more selected stay-out zones 332a.

In another version, the manual selection device 376 comprises a keypad device 382 (see FIG. 1C). The keypad device 382 may be coupled to the wand applicator 18, via a wired connection or a wireless connection. The user 52, or operator 54, may type or input one or more identifiers 373, or other information, from the preprogrammed list 378, into the keypad device 382 to identify and select an identifier 373 associated with, or corresponding to, a desired zone 308a, for example, a selected stay-in zone 314a, or a selected stay-out zone 332a, and to recall from the memory unit 66 the selected desired path 310b (see FIG. 1C) associated with the selected stay-in zone 314a and/or the selected stay-out zone path 312b (see FIG. 1C) associated with the one or more selected stay-out zones 332a.

In yet another version, the manual selection device 376 comprises a separate mobile device 362, such as a smartphone, a tablet computer, or another suitable separate mobile device, having an application 384 (see FIG. 1C) that is designed to communicate with, and communicates with, the portable wand system 10, for example, over Wi-Fi, blue tooth, or another suitable wireless connection, or a wired connection. The user 52, or operator 54, may type or input one or more identifiers 373, or other information, from the preprogrammed list 378, into the separate mobile device 362 to identify and select an identifier 373 associated with, or corresponding to, a desired zone 308a, for example, a selected stay-in zone 314a, or a selected stay-out zone 332a, and to recall from the memory unit 66 the selected desired path 310b (see FIG. 1C) associated with the selected stay-in zone 314a and/or the selected stay-out zone path 312b (see FIG. 1C) associated with the one or more selected stay-out zones 332a.

As shown in FIG. 1C, after the portable wand system 10, such as the trainable portable wand system 11, is trained in the learn mode 300, the portable wand system 10, such as the trained portable wand system 11a, is used in the operation mode 302. Prior to entering the operation mode 302, the operator 54, or user 52, preferably uses the manual selector button 25 to select an operation mode selection 344 (see FIG. 1C), to activate the portable wand system 10, such as the trained portable wand system 11a, in the operation mode 302. Further, prior to entering the operation mode 302, or after entering the operation mode 302, but prior to operating the wand applicator 18 in the operation mode 302, the user 52, or operator 54, preferably uses the selector assembly 24, such as the barcode assembly 348, the RFID assembly 366, or the manual selector assembly 374, to select a selected stay-in zone 314a having the one or more surfaces 12 to be surface treated, such as disinfected, and selecting the desired path 310, recorded and stored during the first learn mode 300a, corresponding to the selected stay-in zone 314a.

Further, prior to entering the operation mode 302, or after entering the operation mode 302, but prior to operating the wand applicator 18 in the operation mode 302, the operator

54, or user 52, preferably uses the portable wand system 10, such as the trained portable wand system 11a, to identify, with a registration feature 130 (see FIGS. 1A, 4A), a starting position 167 (see FIG. 4A) at one of the one or more surfaces 12 to be surface treated in the selected stay-in zone 314a, where the registration feature 130 registers the wand applicator 18 against a known location 132 (see FIGS. 1A, 4A) in the selected stay-in zone 314a. The portable wand system 10 preferably has the capability of identifying one or more registration features 130 (see FIGS. 1A, 4A) to register the wand applicator 18 against one or more known locations 132 (see FIGS. 1A, 4A) and/or known orientations 134 (see FIG. 1A) at the one or more surfaces 12.

In the operation mode 302, the user 52, or operator 54, manually moves the wand applicator 18 in an operation path 386 (see FIG. 1C), based on, and corresponding, or substantially corresponding, to the desired path 310, in the selected stay-in zone 314a, with the surface treatment application element 16, for example, the UV lamp element 26, activated. The portable wand system 10, such as the trained portable wand system 11a, is used in the operation mode 302 after the learn mode 300, to measure, in real-time, the user 52, or operator 54, manually moving, including manually positioning and orienting, the wand applicator 18 in one or more operation paths 386, based on, and corresponding, or substantially corresponding, to one or more of the plurality of desired paths 310, in one or more of the plurality of stay-in zones 314.

For the selected stay-in zone 314a, the computer program 32, such as the algorithm 32a, of the portable wand system 10, such as the trained portable wand system 11a, compares the operation path 386 to the desired path 310, and indicates to the user 52, or operator 54, when, and if, the operation path 386 deviates from the desired path 310, and indicates if there is a deviation 387 (see FIG. 1C), and indicates to the user 52, or operator 54, when the wand applicator 18 is in proximity to, and oriented towards, one or more of the plurality of stay-out zones 332, to allow for adjusting movement 388 (see FIG. 1C) of the wand applicator 18 and adjusting power 121 to the wand applicator 18. Motion or movement 388 (see FIG. 1C) of the wand applicator 18 of the portable wand system 10, such as the trained portable wand system 11a, in the operation path 386, by the user 52, or operator 54, in the operation mode 302, is compared to the desired path 310 that has been recorded and stored in the memory unit 66, to determine if some or all of the operation path 386 has not deviated too far from the desired path 310, and if so, where those deviations 387 have occurred, and indicating those surfaces 12, zones 308, or other areas, to the user 52, or operator 54, thus identifying the surfaces 12, or zones 308, or other areas, requiring re-application of the surface treatment application 14

When the wand applicator 18 is in proximity to, and oriented towards, one or more of the plurality of stay-out zones 332, the computer program 32, such as the algorithm 32a, provides a feedback signal 390 (see FIG. 1C) to the power supply 117 of the power assembly 108 to cause the power assembly 108 to reduce power 121, or to extinguish power 121, to the wand applicator 18, such as the surface treatment application element 16, for example, the UV lamp element 26, of the wand applicator 18. Further, when the wand applicator 18 is in proximity to, and oriented towards, one or more of the plurality of stay-out zones 332, the computer program 32, such as the algorithm 32a, triggers the indicator element 78 to notify the user 52, or operator 54, of an incorrect position 392 (see FIG. 1C) of the wand applicator 18. As shown in FIG. 1A, and discussed above, the indicator element 78 comprises the binary indicator 80 comprising one of, a light signal 82 coupled to the wand applicator 18, a surface treatment application element flashing light alert 84, an audio alert 86, a sound alert 88, a tactile alert 90, a vibration alert 92, a pulsing alert 94, and a pressure altering alert 96.

Figure 4A:
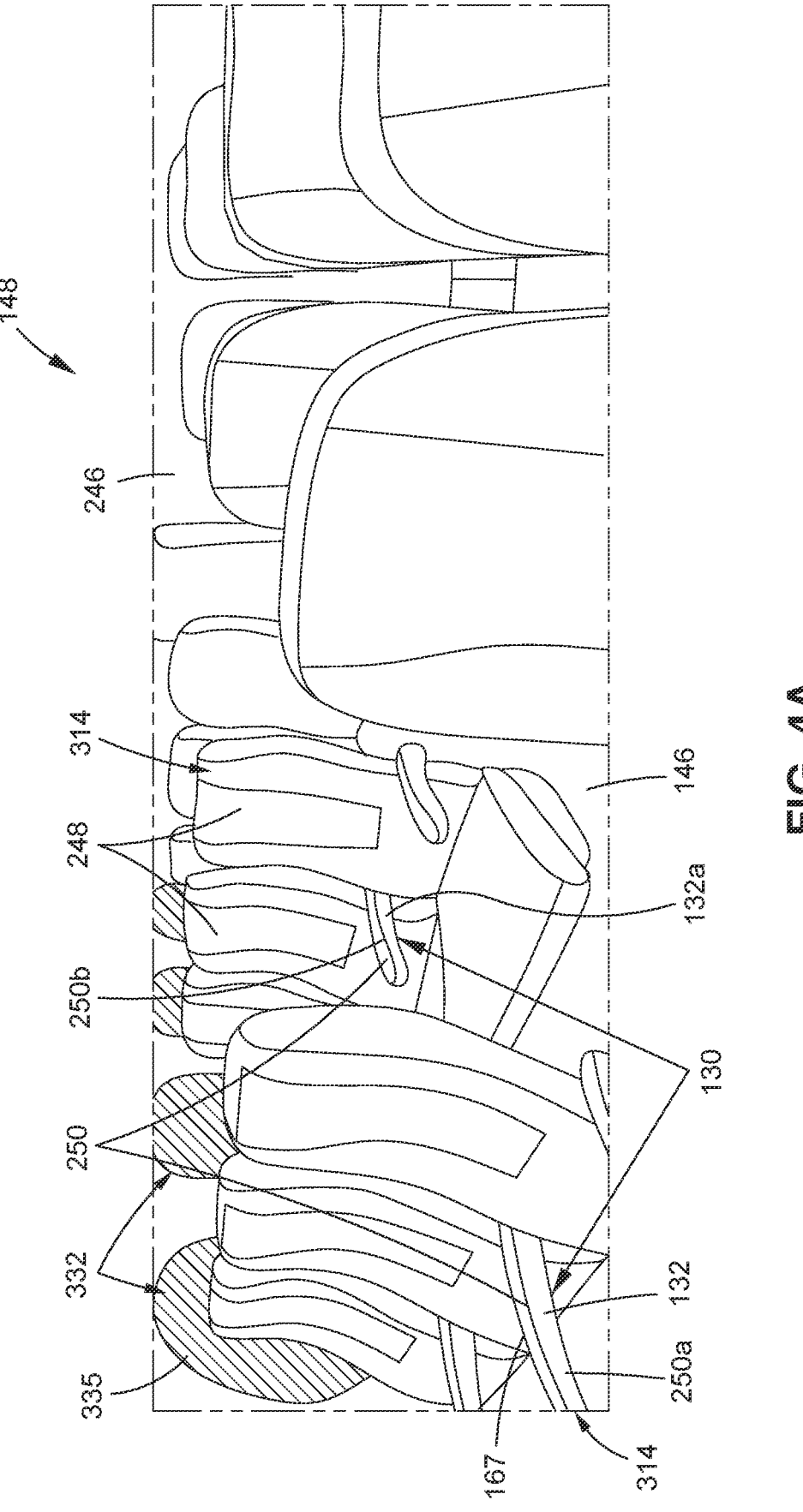
FIG. 4A is an illustration of a front perspective view of an interior of a cabin of an aircraft showing registration features.
Figure 4B:
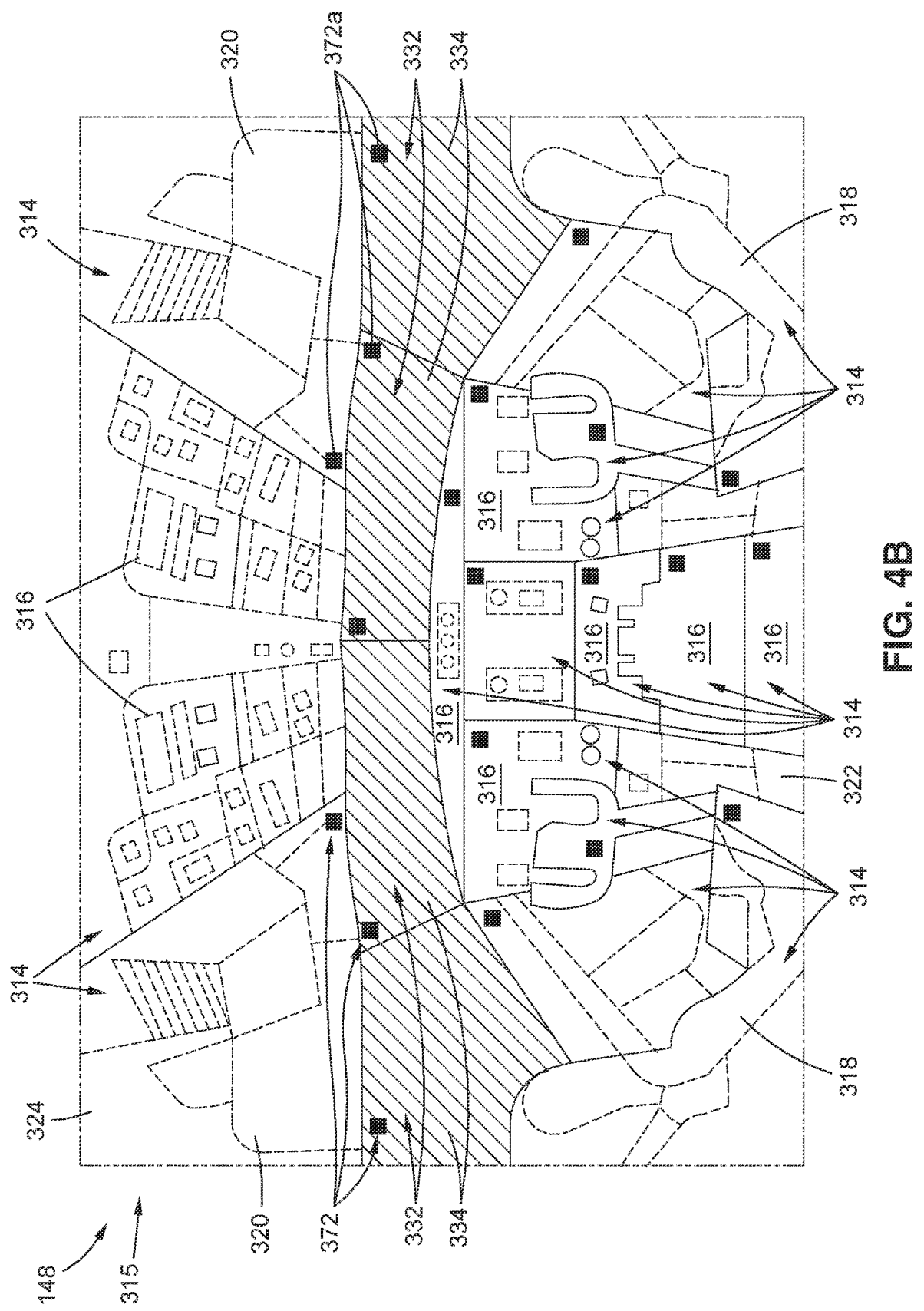
FIG. 4B is an illustration of a back perspective view of an interior of a flight deck of an aircraft showing stay-in zones and stay-out zones with RFID tags.

The portable wand system 10, such as the trained portable wand system 11a, uses the indicator element 78 to issue a warning or notification to the user 52, or operator 54, if the wand applicator 18 is in the incorrect position 392 and positioned or aimed toward the stay-out zones 332, for example, flight deck windows 334 (see FIGS. 1C, 4B). Further, all surfaces or areas that are not on the desired path 310 may be designated as stay-out zones 332.

The portable wand system 10 automatically adjusts its output 394 according to the conditions, or to be consistent with the conditions. For example, if the wand applicator 18 is on the surface 12 to be surface treated in the selected stay-in zone 314a, the wand applicator 18 has power 121 (see FIG. 1A) from the power supply 117 (see FIG. 1A) at a full capacity. However, if the wand applicator 18 veers or enters into, or near, one or more stay-out zones 332, the power 121 from the power supply 117 to the wand applicator 18, and in particular, to the surface treatment application element 16, for example, the UV lamp element 26, of the wand applicator 18, is automatically reduced or extinguished. Thus, the portable wand system 10 adjusts the output 394 of the wand applicator 18, and in particular, of the surface treatment application element 16, such as the UV lamp element 26, when the wand applicator 18 is in the incorrect position 392 and is pointed in the direction of the zone 308 designated as the stay-out zone 332 not to be surface treated. The portable wand system 10, such as the trained portable wand system 11a, verifies that the desired surface treatment application 14b is achieved for the one or more surfaces 12 in the one or more selected stay-in zones 314a.

The portable wand system may optionally further comprise a computer recording system 136 (see FIGS. 1A, 3A-3B) coupled to the wand controller subsystem 30. The computer recording system 136 is operable, or configured, to analyze the positional data 58 of the wand applicator 18, and is operable, or configured, to communicate to the indicator element 78 a status 15 (see FIG. 1B) of the surface treatment application 14, such as the predetermined surface treatment application 14a (see FIG. 1B), or the desired surface treatment application 14b (see FIG. 1B), on the one or more surfaces 12.

As shown in FIG. 1A, the computer recording system 136 comprises a computer 138 coupled to a router device 140 and a wireless access point 142, via an internet connection 144. The wireless network interface 70 of the wand controller subsystem 30 interfaces, or communicates, with the wireless access point 142 of the computer recording system 136. The CPU 60 converts streams of data 68 and may wirelessly transmit the positional data 58, including the desired paths 310 and stay-out zone paths 312 recorded in the learn mode 300 and stored in the memory unit 66, to the computer recording system 136. The computer recording system 136 verifies the location of the wand applicator 18, and calculates the position 50 of the wand applicator 18, and provides feedback as to what surfaces 12 still need to be surface treated with the surface treatment application element 16. The computer recording system 136 also provides a central recording function 242 (see FIGS. 3A-3B), as discussed below, to document and record complete coverage of the one or more surfaces 12 with the surface treatment application 14.

The portable wand system 10 measures positional data 58 of the wand applicator 18 in real-time, and the computer program 32, such as the algorithm 32a, compares the operation path 386 to the desired path 310, to indicate to the user 52, or operator 54, if there is a deviation 387 or not between the operation path 386 and the desired path 310, and to indicate when the desired surface treatment application 14b (see FIG. 1B) is achieved for the one or more surfaces 12, and to indicate a sufficiency of the desired surface treatment application 14b. The portable wand system 10 also verifies and validates that the desired surface treatment application 14b or the predetermined surface treatment application 14a, is sufficient, correct, and complete. As used herein, "desired" or "predetermined" means a target amount, or a correct amount, of surface treatment application to provide sufficient and effective coverage of one or more surfaces.

As shown in FIG. 1A, the portable wand system 10 may be transported, or carried, by the user 52, or operator 54, and/or stored in a system case 122, a system backpack 124, a system roller bag 126, a system shoulder case 128, or another suitable portable case, carrier, or bag.

Now referring to FIG. 1B, FIG. 1B shows exemplary versions of surfaces 12, surface treatment applications 14, and surface treatment application elements (STAE) 16 used with exemplary versions of the portable wand system 10 (see FIG. 1A), including the trainable portable wand system 11 (see FIG. 1C), and the trained portable wand system 11a (see FIG. 1C), of the disclosure.

As shown in FIG. 1B, the one or more surfaces 12 to be surface treated preferably comprise one or more interior surfaces 12a, in an interior 146 of one of, an aircraft 148, a spacecraft 150, an automotive vehicle 152, a watercraft 154, a train 156, a hospital 158, a factory building 160, an office building 162, a movie theater 164, a restaurant 166, or another suitable interior surface.

As further shown in FIG. 1B, the surface treatment application 14, such as the predetermined surface treatment application 14a, or the desired surface treatment application 14b, comprises one of, a disinfection operation 168, an ultraviolet (UV) light disinfection operation 170 for an ultraviolet (UV) light disinfection 172, a decontamination operation 174, a sanitization operation 176, a sterilization operation 178, a curing operation 180, a shot peening operation 182, a chemical contaminant detection operation 184, a biological contaminant detection operation 186, a non-destructive inspection process 188, an eddy current crack detection 190, a paint application 192, an abrasive media blasting operation 194, a sand blasting operation 194a, a surface pre-heating operation 196, a torch welding operation 198, or another suitable surface treatment application. Preferably the surface treatment application 14 (see FIG. 1B) is a predetermined surface treatment application 14 (see FIG. 1B) that is predetermined by amount and coverage.

Preferably, the UV light disinfection 172 is a predetermined ultraviolet (UV) light disinfection 172a (see FIG. 1B) or a desired ultraviolet (UV) light disinfection 172b (see FIG. 1B) that is predetermined or desired by amount and coverage. For a predetermined UV light disinfection 172a or a desired UV light disinfection 172b, the level of treatment is preferably in a range of 2 (two) millijoules per square centimeter to 100 (one hundred) millijoules per square centimeter irradiance of UV light 28. Preferably, the traversing speed of the wand applicator 18 across the surface 12 to be disinfected, or surface treated, for the predetermined UV light disinfection 172 is in a range of 1 (one) inch per second to 10 (ten) inches per second. Preferably, the distance the wand applicator 18 is held by the user 52 from the surface 12 to be disinfected or surface treated is in a range of 1 (one) inch to 6 (six) inches.

As further shown in FIG. 1B, the surface treatment application element 16 comprises one of, an ultraviolet (UV) lamp element 26, a gaseous dispersal element 200, an aerosolized element 202, a disinfectant fluid 204, a disinfectant gas 206, a sanitizing fluid 208, a sanitizing gas 210, a sterilizing fluid 212, a sterilizing gas 214, a cleaning solution 216, a curing element 218, a shot peening element 220, a contamination detection element 222, a paint 224, an abrasive media blasting element 226, a sand blasting element 226a, a surface pre-heating element 228, and a torch welding element 230.

Figure 2B:
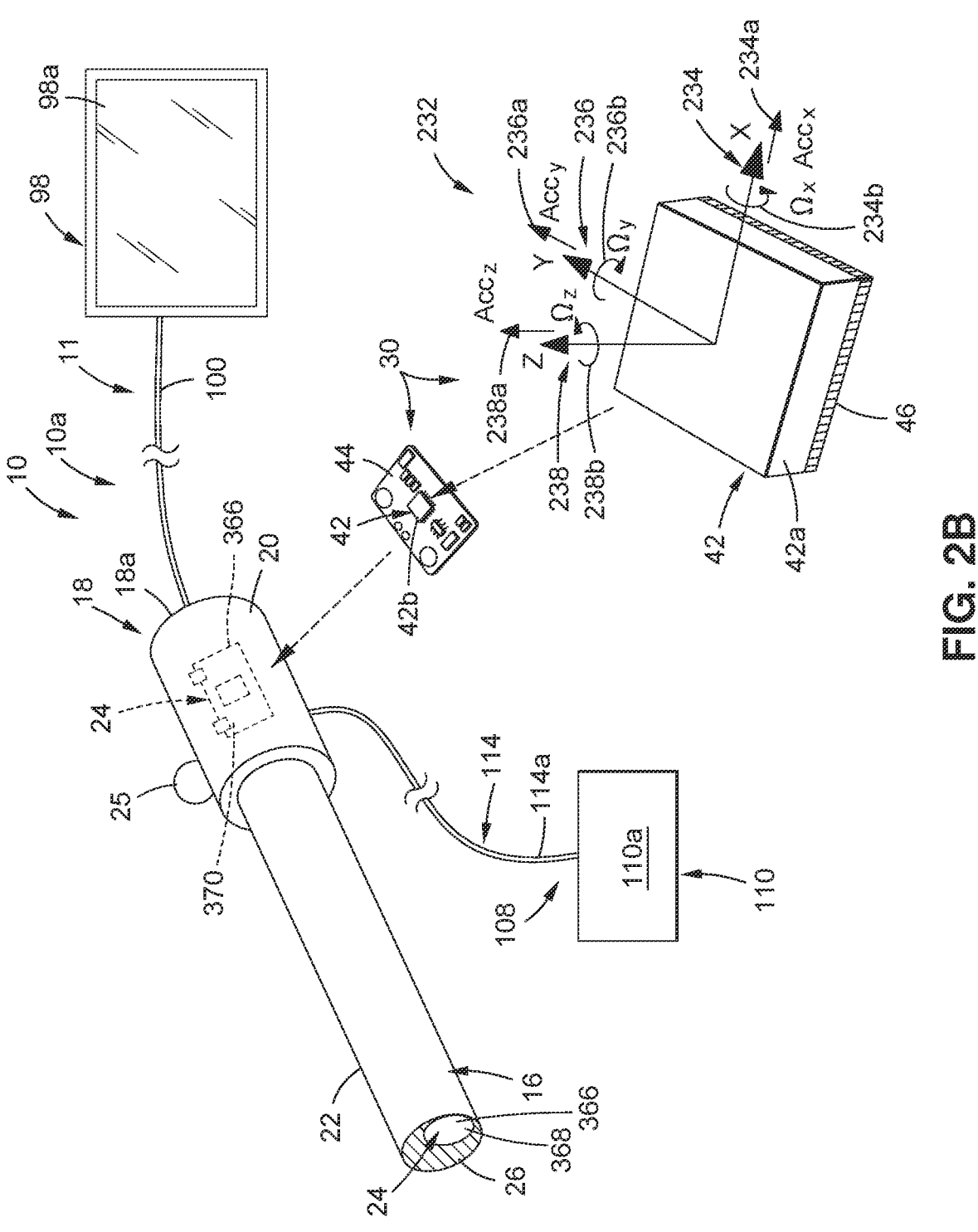
FIG. 2B is an illustration of a perspective view of the portable wand system of FIG. 2A with a video display and the RFID reader and the RFID electronics.

Now referring to FIGS. 2A-2B, FIG. 2A is an illustration of a perspective view of a version of a portable wand system 10, such as the portable wand system 10a, for example, the trainable portable wand system 11, of the disclosure, with an indicator element 78 in the form of a binary indicator 80, and with an RFID reader 368 and RFID electronics 370. FIG. 2B is an illustration of a perspective view of the portable wand system 10, such as portable wand system 10a, for example, the trainable portable wand system 11, of FIG. 2A, with an indicator element 78 in the form of a video display 98, and with the RFID reader 368 and RFID electronics 370.

As shown in FIGS. 2A-2B, the portable wand system 10, such as the portable wand system 10a, for example, the trainable portable wand system 11, comprises the wand applicator 18, such as the handheld wand applicator 18a, having the handle portion 20 and the head portion 22. The head portion 22 contains the surface treatment application element 16, in the form of the ultraviolet (UV) lamp element 26. The UV lamp element 26 is operable, or configured, to emit an ultraviolet (UV) light 28 (see FIG. 1A) preferably having a wavelength in a range between 200 nanometers to 280 nanometers, to disinfect the one or more surfaces 12. More preferably, the UV lamp element 26 comprises a 222 nm (nanometer) ultraviolet (UV) lamp element 26a (see FIG. 1A) operable, or configured, to emit the UV light 28 having a wavelength of 222 nanometers.

As further shown in FIGS. 2A-2B, the portable wand system 10, such as the portable wand system 10a, for example, the trainable portable wand system 11, comprises the manual selector button 25 on the handle portion 20. In FIG. 2A, the indicator element 78 is on the handle portion 20 and comprises the binary indicator 80, such as in the form of a light signal 82. However, the binary indicator 80 may comprise another type of binary indicator as shown in FIG. 1A, for example, one of, a surface treatment application element (STAE) flashing light alert 84, for example, an ultraviolet (UV) lamp element flashing light alert 84a, an audio alert 86, a sound alert 88, a tactile alert 90, a vibration alert 92, a pulsing alert 94, a pressure altering alert 96, or another suitable binary indicator to indicate a predetermined UV light disinfection 172a (see FIG. 1B) of one or more of the one or more surfaces 12 is complete, or to indicate an incorrect position 392 of the wand applicator 18.

In FIG. 2B, the indicator element 78 is connected to the handle portion 20, via a connector element 100, such as an interconnect cable or power cord, and comprises a video display 98, such as a video progress display 98a, to show the progress of the surface treatment application 14 (see FIG. 1B), such as UV light disinfection 172 (see FIG. 1B), on the one or more surfaces 12 (see FIG. 1B) to be surface treated, such as disinfected, sanitized, sterilized, or another type of surface treatment. The video display 98 is visible to the user 52 and shows one or more of, portions 102 (see FIG. 1A) of the one or more surfaces 12 to be disinfected, and a color coded signal 104 (see FIG. 1A), comprising a lighted progress bar 106 (see FIG. 1A), to indicate which portions have complete coverage, that is, to indicate complete coverage portions 102a (see FIG. 1A), or to indicate an incorrect position 392 of the wand applicator 18.

As further shown in FIGS. 2A-2B, the portable wand system 10, such as the portable wand system 10a, for example, the trainable portable wand system 11, comprises, in one version, the selector assembly 24 comprising the RFID assembly 366, including the RFID reader 368 located on the head portion 22 of the wand applicator 18, and the RFID electronics 370 located in the handle portion 20 of the wand applicator 18.

Alternatively, the portable wand system 10, such as the portable wand system 10a, for example, the trainable portable wand system 11, comprises, in another version, as discussed above, the selector assembly 24 comprising the barcode assembly 348 (see FIG. 1C), including the barcode camera 350 (see FIG. 1C) located on the head portion 22 of the wand application 18, and the decoder electronics 352 (see FIG. 1C) coupled to the barcode camera 350, or located in the handle portion 20 of the wand applicator 18. Alternatively, the portable wand system 10, such as the portable wand system 10a, for example, the trainable portable wand system 11, comprises, in yet another version, as discussed above, the selector assembly 24 comprising the manual selector assembly 374 (see FIG. 1C), including the manual selection device 376 (see FIG. 1C) located on the wand applicator 18, or in communication with the wand applicator 18 or portable wand system 10, where the manual selection device 376 is designed, or configured, to access the preprogrammed list 378 (see FIG. 1C) of identifiers 373 (see FIG. 1C), or other information.

As further shown in FIGS. 2A-2B, the portable wand system 10, such as the portable wand system 10a, for example, the trainable portable wand system 11, comprises the power assembly 108, such as coupled to the wand applicator 18. As shown in FIGS. 2A-2B, the power assembly 108 comprises the energy storage device 110, such as a battery 110a. As further shown in FIGS. 2A-2B, the energy storage device 110 is connected to the wand applicator 18, via a wired connector 114, such as a power interconnect cable 114a.

As further shown in FIGS. 2A-2B, the portable wand system 10, such as the portable wand system 10a, for example, the trainable portable wand system 11, comprises the wand controller subsystem 30. In this version, the wand controller subsystem 30 is incorporated in the handle portion 20 of the wand applicator 18. In other versions, the wand controller subsystem 30 may be separate, but wired or wirelessly connected, to the wand applicator 18. For example, the wand controller subsystem 30 may be located in the system case 122 (see FIG. 1A), the system backpack 124 (see FIG. 1A), the system roller bag 126 (see FIG. 1A), the system shoulder case 128 (see FIG. 1A), or another transport or carrier apparatus, used to transport and store the portable wand system 10.

The wand controller subsystem 30 comprises a computer program 32 (see FIG. 1A), such as an algorithm 32a (see FIG. 1A). In one version, as shown in FIGS. 2A-2B, the wand controller subsystem 30 comprises the inertial measurement unit (IMU) 42, such as the 6 degrees of freedom inertial measurement unit (IMU) 42*a*. Alternatively to the IMU 42, the wand controller subsystem 30 may comprise separately, or in combination, one or more of, a fixed position extensometer 72, a rotary position sensor 74, and/or an external photogrammetric sensor 76. The inertial measurement unit (IMU) 42 comprises an integrated circuit 42*b* (see FIGS. 2A-2B), such as a chip, mounted on a circuit board 44, and comprises an accelerometer 46 (see FIGS. 2A-2B). As discussed above, the wand controller subsystem 30 further comprises a central processing unit (CPU) 60 (see FIG. 1A) coupled to the IMU 42, an ultraviolet (UV) lamp element power feedback 64 to the CPU 60, and a memory unit 66 coupled to the CPU 60. The wand controller subsystem 30 may further comprise a wireless network interface 70 coupled to the CPU 60.

As further shown in FIGS. 2A-2B, the inertial measurement unit (IMU) 42 uses an xyz coordinate axis system 232 to measure acceleration 48 (see FIG. 1A) and positions 50 (see FIG. 1A) of the wand applicator 18. FIGS. 2A-2B show an x-axis 234 with an x-acceleration 234*a* and an x-rotation 234*b*. FIGS. 2A-2B show a y-axis 236 with a y-acceleration 236*a* and a y-rotation 236*b*. FIGS. 2A-2B show a z-axis 238 with a z-acceleration 238*a* and a z-rotation 238*b*.

Figure 3A:
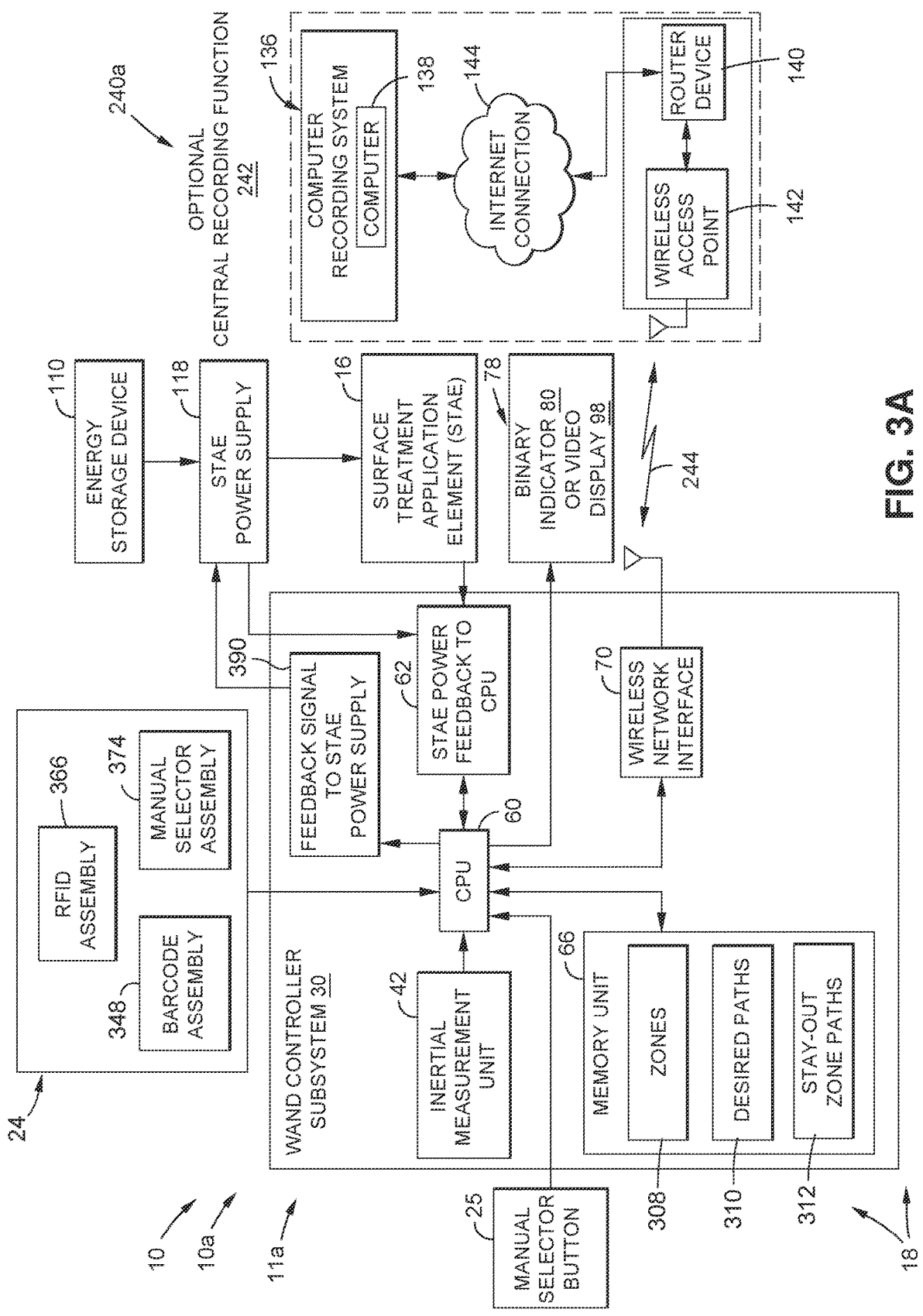
FIG. 3A is an illustration of a system flow diagram of a version of a portable wand system of the disclosure having a surface treatment application element and a computer recording system.
Figure 3B:
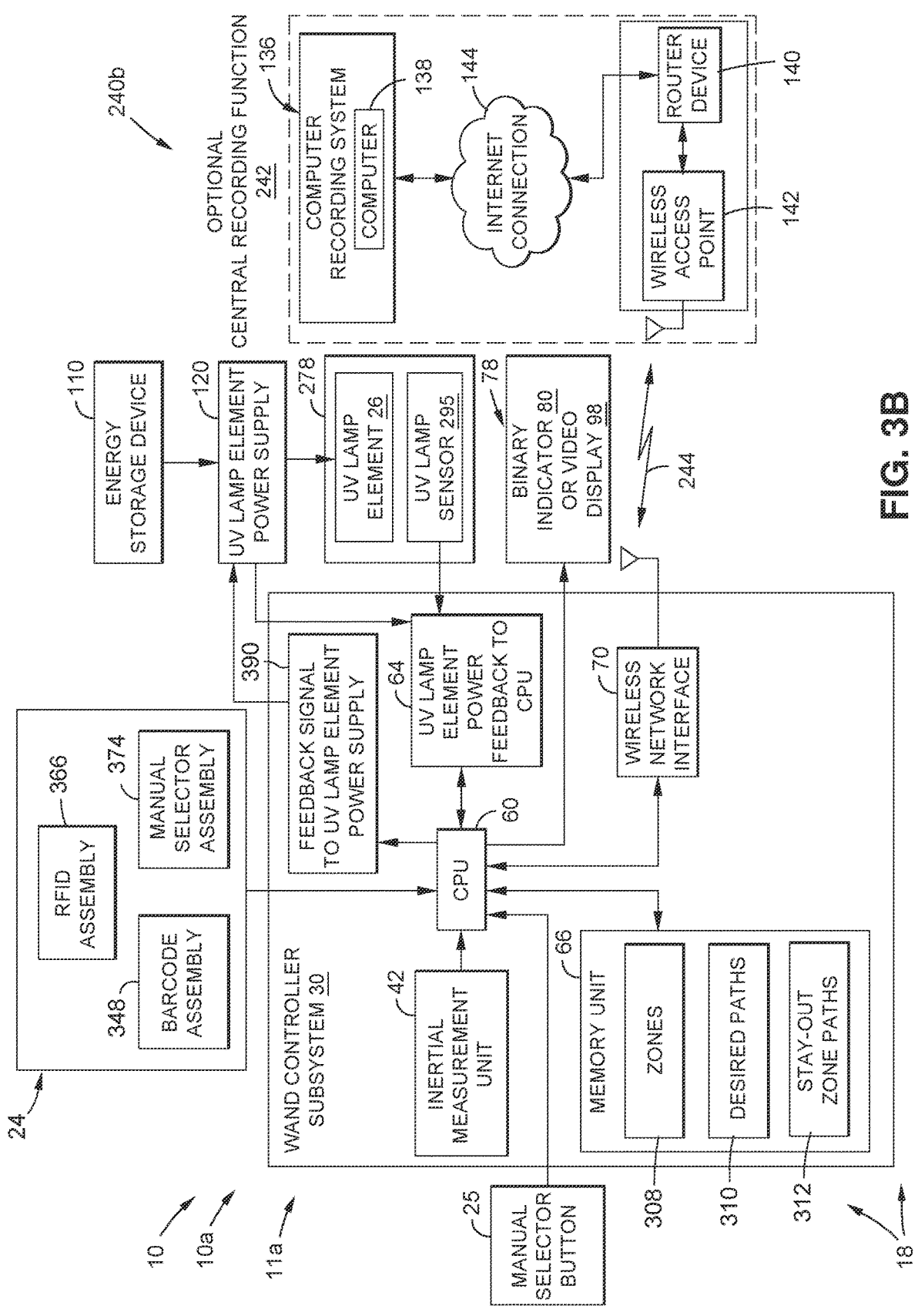
FIG. 3B is an illustration of a system flow diagram of a version of a portable wand system of the disclosure having an ultraviolet (UV) lamp element and a computer recording system.

Now referring to FIGS. 3A-3B, FIG. 3A is an illustration of a system flow diagram 240*a* of a version of a portable wand system 10, such as in the form of portable wand system 10*b*, for example, the trained portable wand system 11*a*, of the disclosure, having a surface treatment application element 16 and a computer recording system 136. FIG. 3B is an illustration of a system flow diagram 240*b* of a portable wand system 10, such as in the form of portable wand system 10*b*, for example, the trained portable wand system 11*a*, having an ultraviolet (UV) lamp element 26 and a computer recording system 136.

As shown in FIGS. 3A-3B, the portable wand system 10, such as in the form of portable wand system 10*b*, for example, the trained portable wand system 11*a*, comprises the wand applicator 18 having the manual selector button 25, the wand controller subsystem 30, the energy storage device 110, the indicator element 78, and the computer recording system 136, which is optional. As shown in FIGS. 3A-3B, the manual selector button 25 and the inertial measurement unit (IMU) 42 are connected in a one-way communication to the CPU 60 of the wand controller subsystem 30. The IMU 42 measures the acceleration 48 (see FIG. 1A) and position 50 (see FIG. 1A) of the wand applicator 18 and sends the data 68 (see FIG. 1A) to the CPU 60.

As further shown in FIGS. 3A-3B, the memory unit 66 and the wireless network interface 70 are connected to the CPU 60 in a two-way communication. The memory unit 66 stores data 68 (see FIG. 1A), including the zones 308, such as the stay-in zones 314 (see FIG. 1C) and the stay-out zones 332 (see FIG. 1C), including the desired paths 310 recorded during the learn mode 300 (see FIG. 1C), such as the first learn mode 300*a* (see FIG. 1C), and including the stay-out zone paths 312, recorded during the learn mode 300, such as the second learn mode 300*b* (see FIG. 1C). The CPU 60 can both store data 68 (see FIG. 1A) in the memory unit 66 and read data 68 from the memory unit 66. The CPU 60 can both send signals to the wireless network interface 70 and receive signals from the wireless network interface 70.

As further shown in FIGS. 3A-3B, the CPU 60 sends data 68 to the indicator element 78, such as the binary indicator 80, or the video display 98. As further shown in FIGS. 3A-3B, the portable wand system 10, such as in the form of portable wand system 10*b*, for example, the trained portable wand system 11*a*, comprises the selector assembly 24 in a one-way communication with the CPU 60. As shown in FIGS. 3A-3B, the selector assembly 24 comprises one of, the barcode assembly 348, the RFID assembly 366, and the manual selector assembly 374.

As shown in FIG. 3A, the energy storage device 110 provides energy to a surface treatment application element (STAE) power supply 118, and the energy storage device 110 provides energy to a surface treatment application element (STAE) power feedback 62 to the CPU 60. As further shown in FIG. 3A, the surface treatment application element (STAE) power supply 118 supplies power to the surface treatment application element (STAE) 16, and the STAE 16 provides feedback to the STAE power feedback 62 to the CPU 60. The STAE power feedback 62 determines the output 394 (see FIG. 1C) of the surface treatment application element (STAE) 16 and the duration and sends the data 68 to the CPU 60. FIG. 3A further shows a feedback signal 390 from the CPU 60 to the STAE power supply 118. When the wand applicator 18 is in proximity to, and oriented towards, one or more of the plurality of stay-out zones 332, the computer program 32, such as the algorithm 32*a*, of the CPU 60 provides the feedback signal 390 to the STAE power supply 118, to cause the power assembly 108 (see FIG. 1A) to reduce power 121 (see FIG. 1A), or to extinguish power 121, to the wand applicator 18, such as the surface treatment application element 16, of the wand applicator 18. Further, when the wand applicator 18 is in proximity to, and oriented towards, one or more of the plurality of stay-out zones 332, the computer program 32, such as the algorithm 32*a*, of the CPU 60 triggers the indicator element 78 to notify the operator 54, or the user 52, with an alert or notification of an incorrect position 392 (see FIG. 1C) of the wand applicator 18.

As shown in FIG. 3B, the energy storage device 110 provides energy to a UV lamp element power supply 120 and provides energy to a UV lamp element power feedback 64 to the CPU 60. As further shown in FIG. 3B, the UV lamp element power supply 120 supplies power to a housing 278 that houses the UV lamp element 26 and an ultraviolet (UV) lamp sensor 295. The UV lamp sensor 295 may comprise a photosensor, for example, an ultraviolet (UV) fluence sensor, which is a photodiode device that measures the ultraviolet (UV) light output in real-time, and reports that value back as feedback to the UV lamp element power feedback 64 to the CPU 60. The UV lamp element power feedback 64 determines the UV lamp element 26 UV light output and duration and sends the data 68 to the CPU 60.

FIG. 3B further shows a feedback signal 390 from the CPU 60 to the UV lamp element power supply 120. When the wand applicator 18 is in proximity to, and oriented towards, one or more of the plurality of stay-out zones 332, the computer program 32, such as the algorithm 32*a*, of the CPU 60 provides the feedback signal 390 to the UV lamp element power supply 120, to cause the power assembly 108 (see FIG. 1A) to reduce power 121 (see FIG. 1A), or to extinguish power 121, to the wand applicator 18, such as the UV lamp element 26, of the wand applicator 18. Further, when the wand applicator 18 is in proximity to, and oriented towards, one or more of the plurality of stay-out zones 332, the computer program 32, such as the algorithm 32*a*, triggers the indicator element 78 to notify the operator 54, or the user 52, with an alert or notification of an incorrect position 392 (see FIG. 1C) of the wand applicator 18. As shown in FIG. 1A, the indicator element 78 comprises the binary indicator 80 comprising one of, a light signal 82 coupled to the wand applicator 18, a surface treatment application element flashing light alert 84, an audio alert 86, a sound alert 88, a tactile alert 90, a vibration alert 92, a pulsing alert 94, and a pressure altering alert 96.

As further shown in FIGS. 3A-3B, the portable wand system 10, such as the portable wand system 10b, is wirelessly coupled to the computer recording system 136 to provide a central recording function 242, which is optional. The computer recording system 136 provides the central recording function 242 (see FIGS. 3A-3B) to document and record the complete coverage of the one or more surfaces 12 with the surface treatment application 14.

The computer recording system 136 comprises a computer 138 (see FIGS. 3A-3B). The CPU 60 converts the streams of data 68 (see FIG. 1A) and wirelessly transmits the position 50 (see FIG. 1A), to the computer recording system 136. The computer recording system 136 verifies location, and calculates position, and provides feedback, as to what surface 12, object, and/or area, still needs to be surface treated.

The computer 138 is wirelessly connected to a router device 140 (see FIGS. 3A-3B), via an internet connection 144 (see FIGS. 3A-3B). As shown in FIGS. 3A-3B, the router device 140 is connected to a wireless access point 142. As shown in FIGS. 3A-3B, the wireless network interface 70 is wirelessly connected, via a wireless connection 244, to the wireless access point 142 of the central recording function 242.

Now referring to FIG. 4A, FIG. 4A is an illustration of a front perspective view of an interior 146 of a cabin 246 of an aircraft 148 showing cabin seats 248 and registration features 130. In an exemplary version, the registration features 130 comprise arm rests 250 of the cabin seats 248. The registration features 130 are known locations 132 in the area or areas to be treated with the surface treatment application 14, such as the desired surface treatment application 14b.

To enable use of an inertial measurement unit (IMU) 42 with a low-cost accelerometer 46 having measurement drift characteristics that only permit short duration operation before location errors become large, the wand applicator 18 may be periodically "registered" against a known location 132 or datum (i.e. temporarily placed in a known orientation and location), such as the arm rest 250 on the next cabin seat 248 in sequence. For example, in FIG. 4A, a forward arm rest 250a may serve as a starting position 167 for the wand applicator 18 and a known location 132, and an aft arm rest 250b comprises a subsequent known location 132a. Once the wand applicator 18 is positioned on the aft arm rest 250b at the subsequent known location 132a in the sequence, the user 52, or the operator 54, then briefly presses the manual selector button 25 (see FIGS. 2A-2B) on the wand applicator 18 that provides the portable wand system 10 an indication to begin the next segment of surface treatment application 14, for example, UV light disinfection 172 (see FIG. 1B), starting in the subsequent known location 132a, and long enough to treat the one or more surfaces 12 in the sub-area until the next registration with the registration feature 130 occurs.

FIG. 4A further shows stay-in zones 314, such as the cabin seats 248, that have one or more surfaces 12 (see FIG. 1A) to be surface treated with the surface treatment application 14 (see FIG. 1A) of the surface treatment application element 16 (see FIG. 1A) applied by the portable wand system 10 (see FIGS. 1A, 1C). FIG. 4A further shows stay-out zones 332 (indicated with shading in FIG. 4A), such as the cabin windows 335, that are to be avoided and are not to be surface treated with the surface treatment application 14 applied by the portable wand system 10.

Now referring to FIG. 4B, FIG. 4B is an illustration of a back perspective view of an interior 146 of a flight deck 315 of an aircraft 148 showing exemplary stay-in zones 314 and exemplary stay-out zones 332 tagged with RFID tags 372, such as passive RFID tags 372a. FIG. 4B shows the stay-in zones 314 in the flight deck 315 to be surface treated, for example, disinfected, with the portable wand system 10 (see FIGS. 1A, 1C). FIG. 4B shows the stay-in zones 314 including flight deck control areas 316, flight deck seats 318, flight deck panel areas 320, a flight deck floor 322, and a flight deck ceiling 324. FIG. 4B further shows stay-out zones 332 (indicated with shading in FIG. 4B) in the flight deck 315 to be avoided, or not surface treated with the portable wand system 10. FIG. 4B shows the stay-out zones 332 including the flight deck windows 334. FIG. 4B shows both the stay-in zones 314 and the stay-out zones 332 tagged with RFID tags 372 configured, or designed, to be read with an RFID reader 368 (see FIG. 1C) and processed with RFID electronics 370 (see FIG. 1C). The RFID tags 372 may be embedded in, or under, the surfaces 12 (see FIG. 1A) of the stay-in zones 314 and the stay-out zones 332 and not visible, or the RFID tags 372 may be visible on the surface 12 of the stay-in zones 314 and the stay-out zones 332. Alternatively, instead of RFID tags 372, both the stay-in zones 314 and the stay-out zones 332 may have barcodes 354 (see FIG. 1C) applied to the surfaces 12 of the stay-in zones 314 and the stay-out zones 332, or embedded in, or under, the surfaces 12 of the stay-in zones 314 and the stay-out zones 332, and configured, or designed, to be read by the barcode camera 350 (see FIG. 1C) and decoded by the decoder electronics 352 (see FIG. 1C).

Figure 4C:
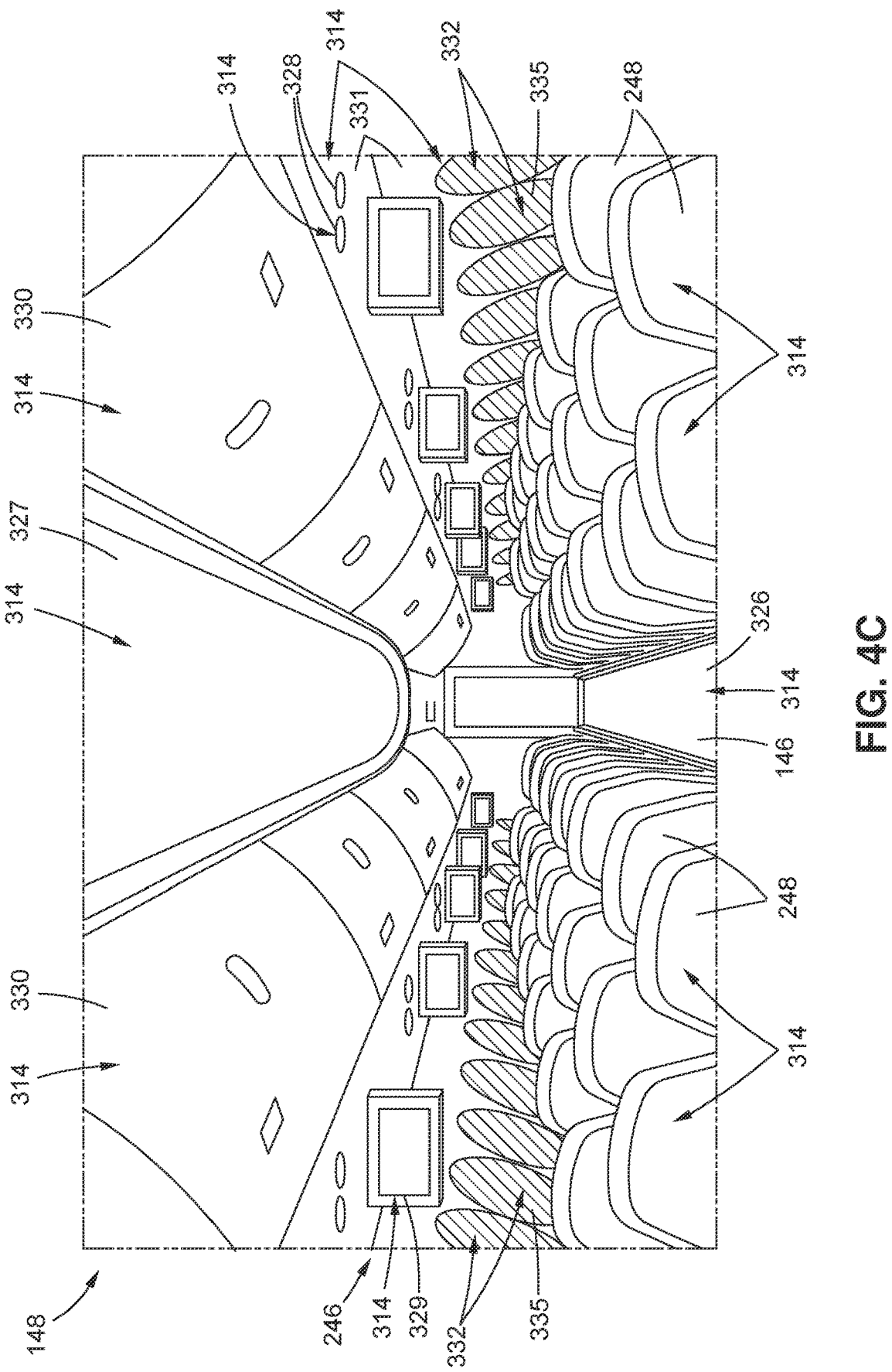
FIG. 4C is an illustration of a back perspective view of an interior of a cabin of an aircraft showing stay-in zones and stay-out zones.

Now referring to FIG. 4C, FIG. 4C is an illustration of a back perspective view of an interior 146 of a cabin 246 of an aircraft 148 showing stay-in zones 314 and stay-out zones 332. In one version, the stay-in zones 314 and the stay-out zones 332 are identified and selected using RFID tags 372 (see FIG. 4B) embedded in the stay-in zones 314 and stay-out zones 332, and the RFID tags 372 are read with an RFID reader 368. In another version, the stay-in zones 314 and the stay-out zones 332 are identified and selected using barcodes 354 (see FIG. 1C) embedded in the stay-in zones 314 and stay-out zones 332, and the barcodes 354 are read with a barcode camera 350. In yet another version, the stay-in zones 314 and the stay-out zones 332 are identified and selected with a manual selector assembly 374 (see FIG. 1C) using a manual selection device 376 (see FIG. 1C), as discussed above, accessing a preprogrammed list 378 (see FIG. 1C) or identifiers 373 (see FIG. 1C) or other information.

FIG. 4C shows the stay-in zones 314 in the cabin 246 to be surface treated with the surface treatment application 14, such as UV light disinfection 172 (see FIG. 1B), using the portable wand system 10. FIG. 4C shows the stay-in zones 314, including the cabin seats 248, the cabin floor 326, cabin ceiling 327, passenger service units 328, monitors 329, overhead stowage bins 330, and cabin panel areas 331. Passenger service units 328 are components positioned above the cabin seats 248 and may comprise one or more of, an attendant call interface, an overhead light, an air flow adjuster, warning signs to advise passengers during flight, or other suitable components. FIG. 4C further shows the stay-out zones 332 in the cabin 246 not to be surface treated, and to be avoided with the surface treatment application 14 of the portable wand system 10. FIG. 4C shows the stay-out zones 332 (indicated with shading in FIG. 4C), including the cabin windows 335.

Figure 5A:
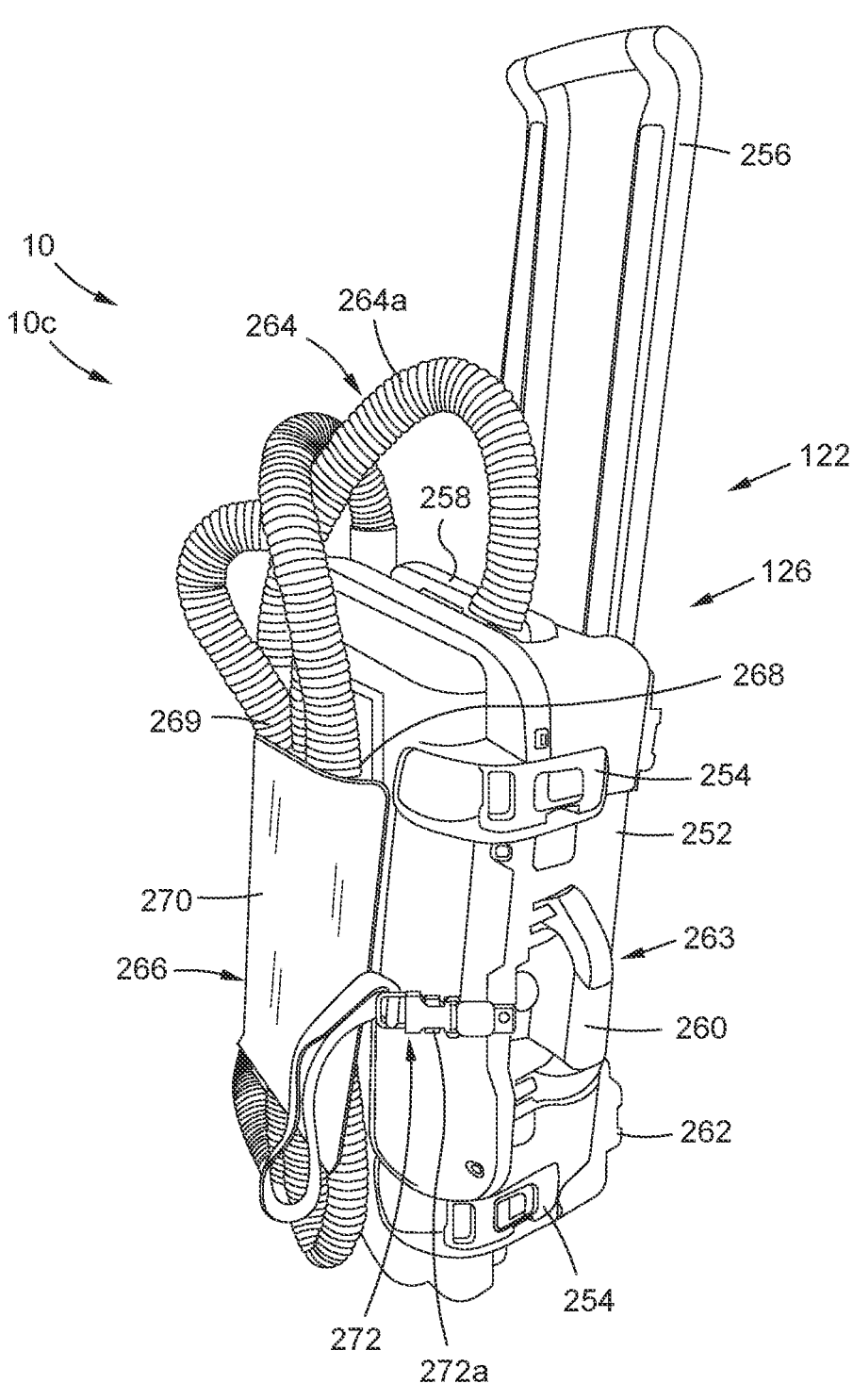
FIG. 5A is an illustration of a front perspective view of a portable wand system of the disclosure used with a system roller bag, where the system roller bag is in a closed position.

Now referring to FIGS. 5A-5E show various views of a version of a portable wand system 10, such as in the form of portable wand system 10c, of the disclosure, used with a system case 122, such as in the form of a system roller bag 126. FIG. 5A is an illustration of a front perspective view of the portable wand system 10, such as the portable wand system 10c, used with the system case 122, such as the system roller bag 126, storing the wand applicator 18 (see FIG. 5B). FIG. 5A shows the system case 122, such as the system roller bag 126, having a hard shell case 252 with latches 254, a telescopic handle 256, a top handle 258, a side handle 260, and roller wheels 262. As shown in FIG. 5A, the system case 122, such as the system roller bag 126, is in a closed position 263. In this version, the portable wand system 10, such as the portable wand system 10c, further comprises a hose 264, such as an air hose 264a, that is attached to the wand applicator 18 (see FIG. 5B). As shown in FIG. 5A, the portable wand system 10, such as the portable wand system 10c, may further comprise a hose securing assembly 266 to secure the hose 264 against an outer surface 268 of the hard shell case 252. As shown in FIG. 5A, the hose securing assembly 266 comprises a fabric cover 270 coupled to a securing element 272, such as a buckle 272a, or other suitable securing element.

Figure 5B:
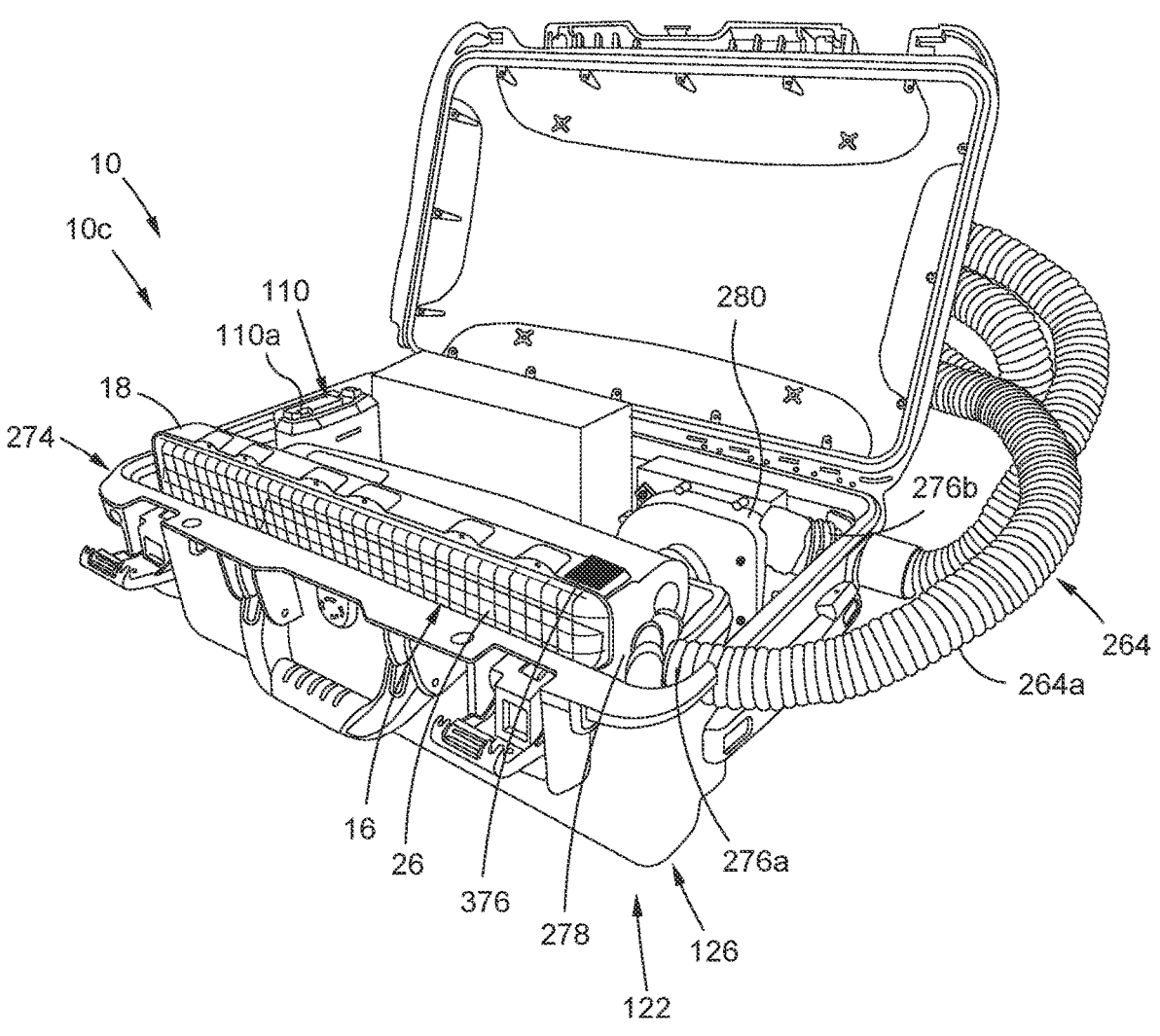
FIG. 5B is an illustration of a front side perspective view of the portable wand system of FIG. 5A, showing a wand applicator with a manual selection device, and used with the system roller bag, where the system roller bag is in an open position.

FIG. 5B is an illustration of a front side perspective view of the portable wand system 10, such as the portable wand system 10c, of FIG. 5A, showing the wand applicator 18 with a manual selection device 376, and used with the system case 122, such as the system roller bag 126, storing the wand applicator 18 and the energy storage device 110, such as a battery 110a. The system case 122, such as the system roller bag 126, is in an open position 274. The wand applicator 18 contains the surface treatment application element 16, such as in the form of the UV lamp element 26. As shown in FIG. 5B, a manual selection device 376 is coupled to, or integrated with, the wand applicator 18. The manual selection device 376 comprises a touchscreen 380b (see FIG. 1C) that may be used by the user 52, or operator 54. Alternatively, the manual selection device 376 may comprise a series of buttons 380a that may be pressed by the user 52, or operator 54. FIG. 5B shows the hose 264, such as the air hose 264a, having a first end 276a attached to a housing 278 of the wand applicator 18, and having a second end 276b attached to a fan 280, such as a cooling fan. The fan 280 cools the wand applicator 18 containing the UV lamp element 26. The fan 280 also cools the energy storage device 110. In this version, the wand controller subsystem 30 (see FIG. 1A) is not in the handle portion 20 of the wand applicator 18, and is in a separate location inside the hard shell case 252 of the system roller bag 126. The system case 122, such as the system roller bag 126, comprises a notch opening 282 (see FIG. 5B), to receive a portion 283 (see FIG. 5B) of the hose, and to allow the wand applicator 18 to be stowed in the system case 122, when the system case 122 is in a closed position 263 (see FIG. 5A).

Figure 5C:
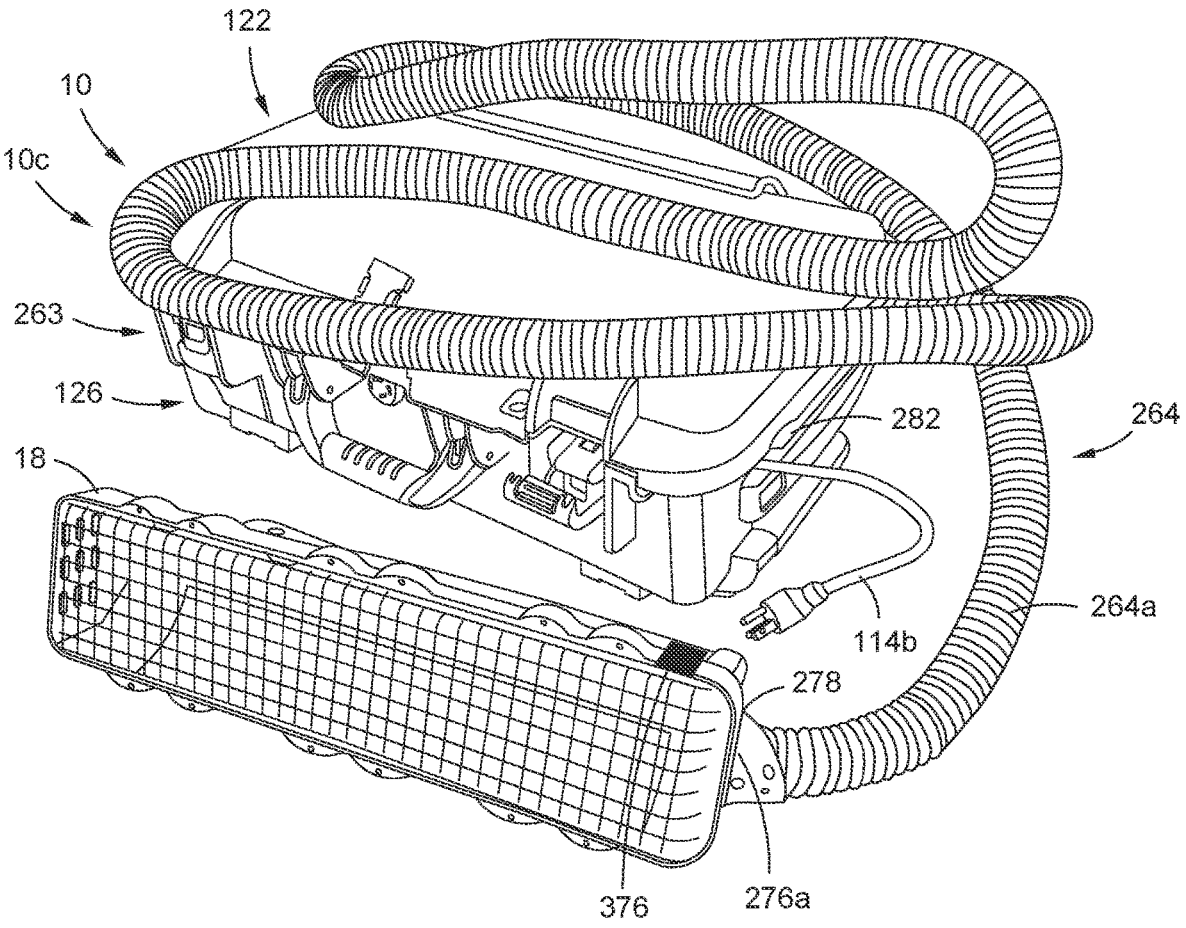
FIG. 5C is an illustration of a front side perspective view of the portable wand system of FIG. 5B, showing the wand applicator with the manual selection device, and showing the system roller bag in the closed position.

FIG. 5C is an illustration of a front side perspective view of the portable wand system 10, such as the portable wand system 10c, of FIG. 5B, with the system case 122, such as the system roller bag 126, in the closed position 263, and the wand applicator 18 with the manual selection device 376 removed out of the system roller bag 126, ready for use by a user 52 (see FIG. 1A), or an operator 54 (see FIG. 1A). FIG. 5C further shows the manual selection device 376 coupled to, or integrated with, the wand applicator 18. FIG. 5C further shows a power cord 114b (see FIG. 5C) operable to, or configured to, be plugged into an outlet in an interior 146 (see FIG. 1B) of an aircraft 148 (see FIG. 1B), or another suitable vehicle or structure, to undergo a surface treatment application 14 with the portable wand system 10. The power cord 114b is stowed inside the system roller bag 126 during transit. The power cord 114b extends out of a notch opening 282 formed when the system roller bag 126 is in the closed position 263.

Figure 5D:
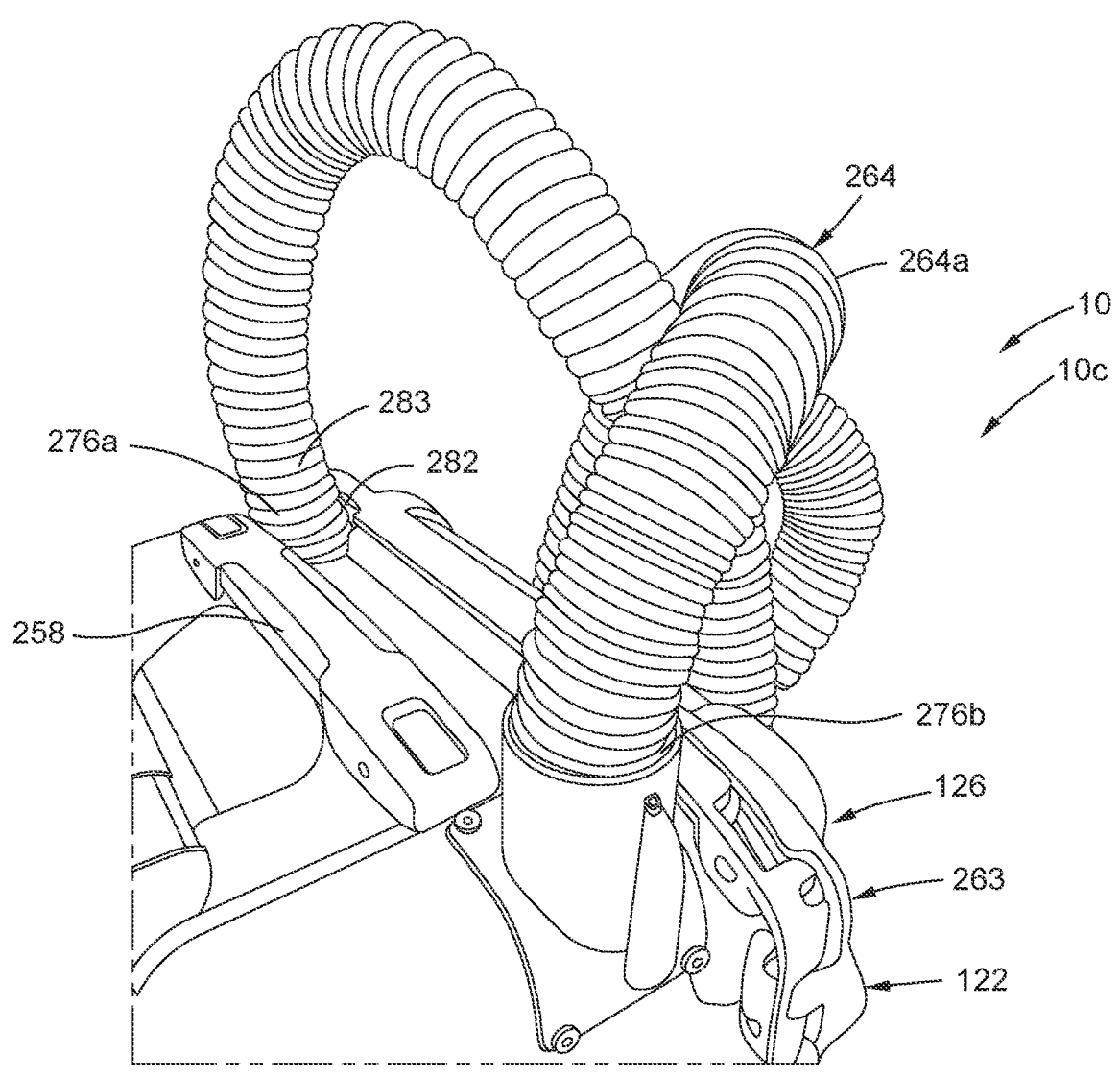
FIG. 5D is an illustration of an enlarged top end view of the system roller bag of FIG. 5A, and shows a hose of the portable wand system, and shows the system roller bag in the closed position.

FIG. 5D is an illustration of an enlarged top end view of the system case 122, such as the system roller bag 126, of FIG. 5A, and the hose 264, such as the air hose 264a, of the portable wand system 10, such as the portable wand system 10c. The system case 122, such as the system roller bag 126, is in the closed position 263. FIG. 5D shows the first end 276a of the hose 264 extending out of the notch opening 282. The hose 264 exits the system roller bag 126 during transit, when the system roller bag 126 is in the closed position 263. The notch opening 282 also allows intake air to be drawn into the fan 280 (see FIG. 5B) even when the system roller bag 126 is in the closed position 263 during operation.

Figure 5E:
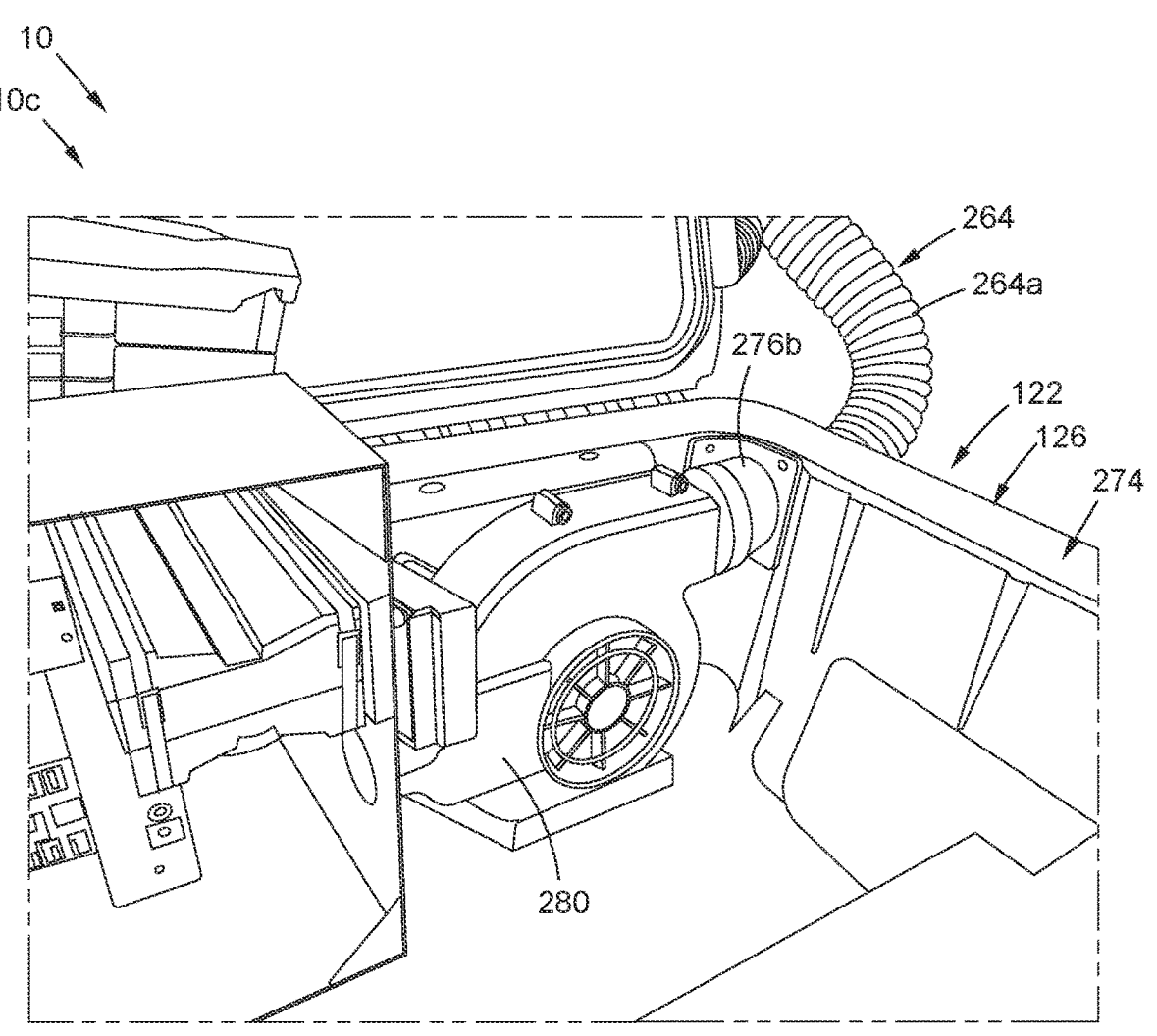
FIG. 5E is an illustration of an enlarged front perspective view of a fan of the portable wand system of FIG. 5B, and shows the system roller bag in the open position.

FIG. 5E is an illustration of an enlarged front perspective view of the fan 280 of the portable wand system 10, such as the portable wand system 10c, of FIG. 5B, with the system case 122, such as the system roller bag 126, in the open position 274. FIG. 5E further shows the second end 276b of the hose 264, such as the air hose 264a, attached to the fan 280.

Figure 6A:
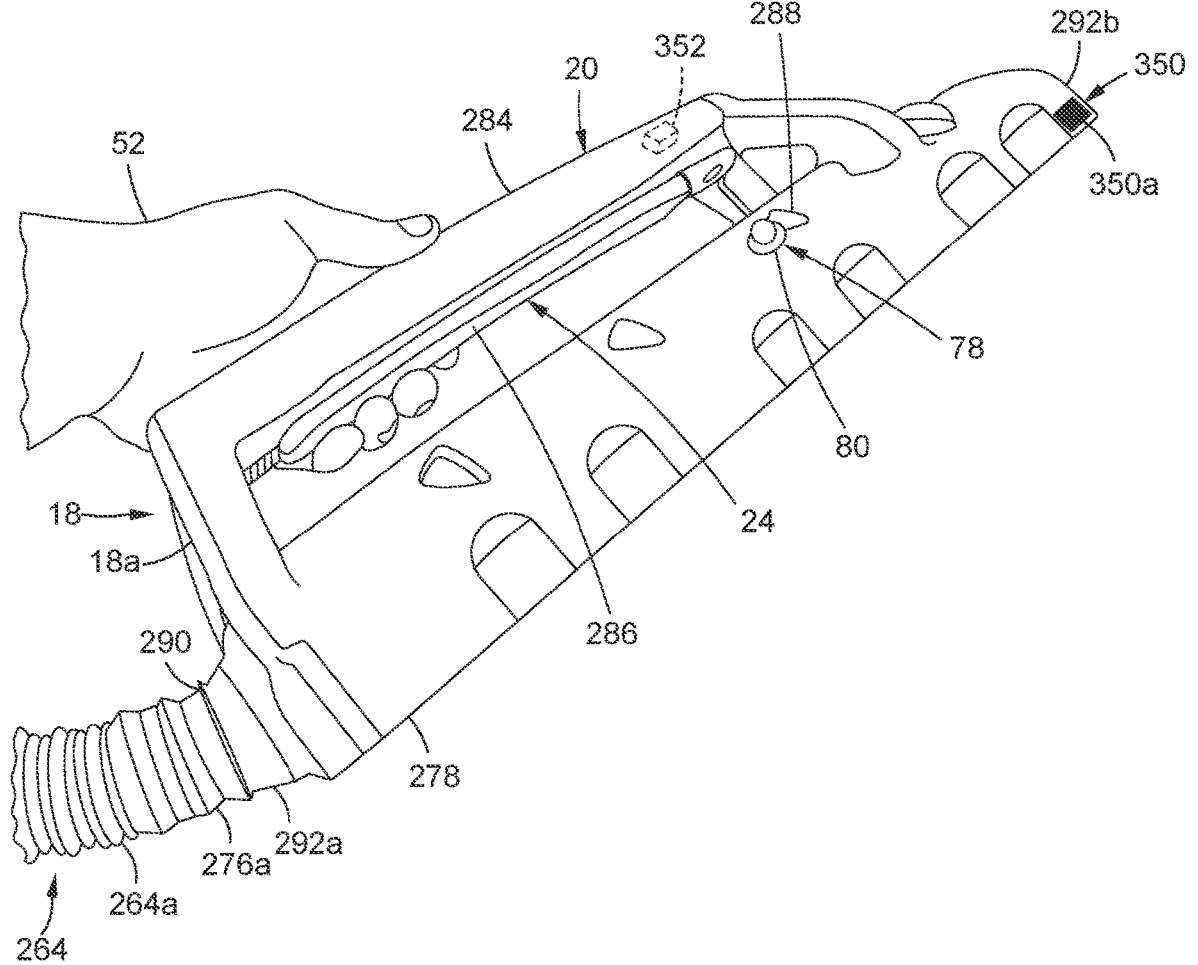
FIG. 6A is an illustration of a side perspective view of a version of a wand applicator with a barcode camera and decoder electronics, held by a user.
Figure 6B:
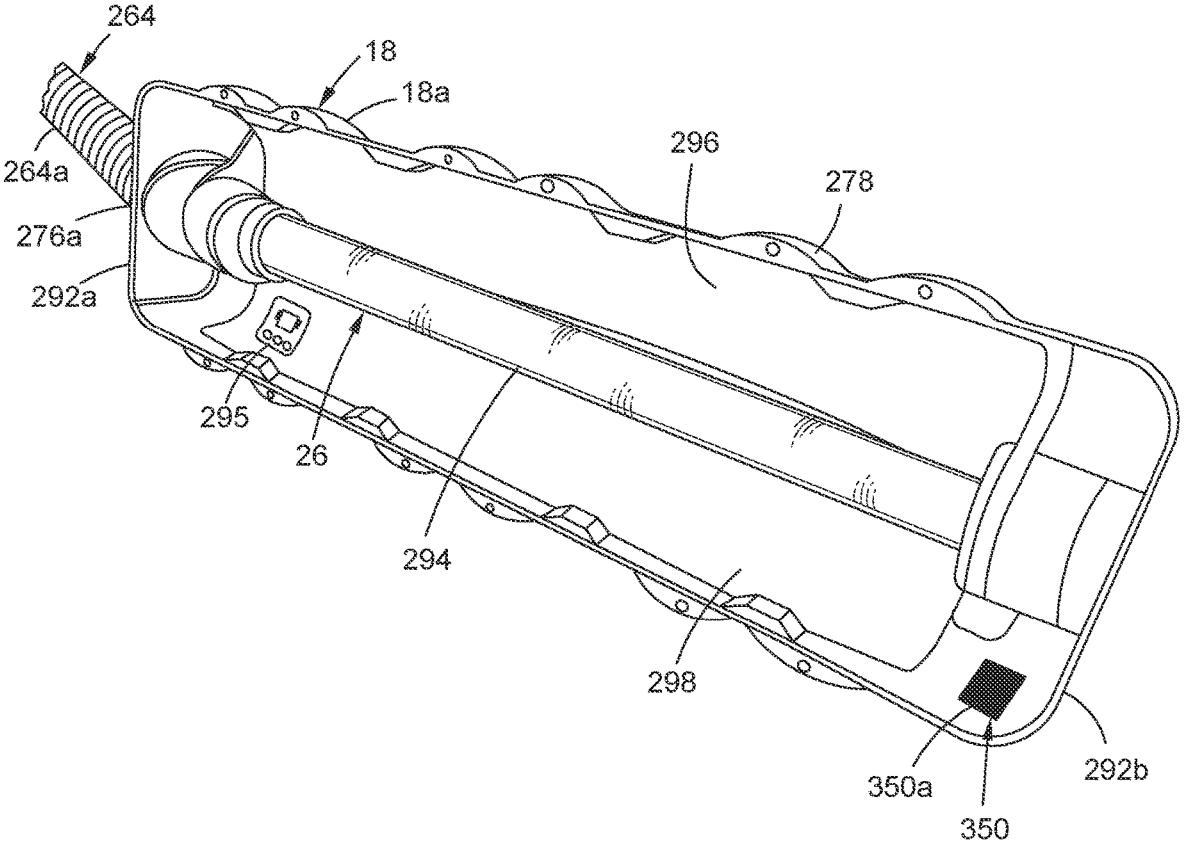
FIG. 6B is an illustration of a bottom perspective view of the wand applicator of FIG. 6A.

FIGS. 6A-6B show a version of a wand applicator 18, such as handheld wand applicator 18a, for one or more versions of a portable wand system 10 (see FIGS. 1A, 2A-2B, 3A-3B), of the disclosure. FIG. 6A is an illustration of a side perspective view of a version of the wand applicator 18, such as the handheld wand applicator 18a, with a barcode camera 350 and decoder electronics 352, held by a user 52. As shown in FIG. 6A, the user 52 holds the handle portion 20 comprising a trigger handle 284. In this version, the manual selector button 25 comprises a trigger portion 286 that may be triggered or actuated by the user anywhere along the length of the trigger portion 286.

FIG. 6A further shows the barcode camera 350, such as a two-dimensional imaging scanner 350a, or barcode reader, coupled to, or integrated with, the wand applicator 18, such as the handheld wand applicator 18a, and positioned near the second end 292b of the wand applicator 18. FIG. 6A further shows decoder electronics 352 located in the handle portion 20 of the wand applicator 18, such as the handheld wand applicator 18a. The barcode camera 350 is designed to read a barcode 354 (see FIG. 1C), and the decoder electronics 352 are designed to decode the data contained in the barcode 354, and send the data to a computing device, such as the CPU 60. The decoder electronics 352 comprise decoder circuitry that can analyze the barcode's image data provided by the barcode camera 350 that sends the barcode's content to the computing device, such as the CPU 60.

FIG. 6A further shows the indicator element 78, such as in the form of the binary indicator 80, coupled to an exterior portion 288 of the housing 278. FIG. 6A further shows the first end 276a of the hose 264, such as the air hose 264a, inserted through a port opening 290 at a first end 292a of the wand applicator 18. FIG. 6A further shows a second end 292b of the wand applicator 18. In this version, the wand controller subsystem 30 (see FIG. 1A) is not in the handle portion 20 of the wand applicator 18, and is in a separate location from the wand applicator 18.

FIG. 6B is an illustration of a bottom perspective view of the wand applicator 18, such as the handheld wand applicator 18a, of FIG. 6B. FIG. 6B shows the housing 278, the first end 292a, and the second end 292b of the wand applicator 18. FIG. 6B further shows the barcode camera 350, such as the two-dimensional imaging scanner 350*a*, coupled to, or integrated with, the wand applicator 18, such as the handheld wand applicator 18*a*, and positioned near the second end 292*b* of the wand applicator 18. FIG. 6B further shows the first end 276*a* of the hose 264, such as the air hose 264*a*, extending from the first end 292*a* of the wand applicator 18. FIG. 6B further shows a UV lamp element 26 comprising an ultraviolet (UV) lamp bulb 294. FIG. 6B further shows an ultraviolet (UV) lamp sensor 295 coupled to an interior 296 of the housing 278 and positioned in range of an emission path of the UV lamp bulb 294. The housing 278 houses the UV lamp bulb 294 and the UV lamp sensor 295. The UV lamp sensor 295 may comprise a photosensor, for example, an ultraviolet (UV) fluence sensor, which is a photodiode device that measures the ultraviolet (UV) light output in real-time. As shown in FIG. 6B, the UV lamp bulb 294 is attached between the first end 292*a* and the second end 292*b* in the interior 296 of the housing 278. FIG. 6B further shows a reflector lining element 298 lining the interior 296 of the housing 278, and positioned behind the UV lamp element 26 comprising the UV lamp bulb 294.

Now referring to FIG. 7, FIG. 7 is an illustration of a flow diagram of a version of a method 400 of the disclosure. In another version of the disclosure, there is provided the method 400 to indicate and verify to an operator 54 (see FIG. 1A), or a user 52 (see FIG. 1A), when a desired surface treatment application 14*b* (see FIG. 1C) is achieved for one or more surfaces 12 (see FIGS. 1A-1C) to be surface treated.

The blocks in FIG. 7 represent operations and/or portions thereof, or elements, and lines connecting the various blocks do not imply any particular order or dependency of the operations or portions thereof, or elements. FIG. 7 and the disclosure of the steps of the method 400 set forth herein should not be interpreted as necessarily determining a sequence in which the steps are to be performed. Rather, although one illustrative order is indicated, it is to be understood that the sequence of the steps may be modified when appropriate. Accordingly, certain operations may be performed in a different order or simultaneously.

As shown in FIG. 7, the method 400 comprises the step of providing 402 a version of a portable wand system 10 (see FIGS. 1A, 2A-2B, 3A-3B, 5B), for example, a trainable portable wand system 11 (see FIGS. 1A, 1C). As discussed in detail above, in one version, the portable wand system 10, for example, the trainable portable wand system 11, comprises a wand applicator 18 (see FIG. 1A) containing a surface treatment application element 16.

The step of providing 402 the portable wand system 10, for example, the trainable portable wand system 11, further comprises, providing the portable wand system 10 having the wand applicator 18 containing the surface treatment application element 16 comprising one of, as shown in FIG. 1B, an ultraviolet (UV) lamp element 26, a gaseous dispersal element 200, an aerosolized element 202, a disinfectant fluid 204, a disinfectant gas 206, a sanitizing fluid 208, a sanitizing gas 210, a sterilizing fluid 212, a sterilizing gas 214, a cleaning solution 216, a curing element 218, a shot peening element 220, a contamination detection element 222, a paint 224, an abrasive media blasting element 226, a sand blasting element 226*a*, a surface pre-heating element 228, and a torch welding element 230.

The portable wand system 10, for example, the trainable portable wand system 11, further comprises a wand controller subsystem 30 (see FIG. 1A) coupled to the wand applicator 18. The wand controller subsystem 30 comprises a computer program 32 (see FIG. 1A), such as an algorithm

32*a* (see FIG. 1A), a memory unit 66 (see FIG. 1A), and a central processing unit (CPU) 60 (see FIG. 1A) coupled to the memory unit 66. The wand controller subsystem 30 may further comprise in one version, an inertial measurement unit (IMU) 42 (see FIG. 1A) coupled to the CPU 60, or in another version, one or more of, a fixed position extensometer 72 (see FIG. 1A), a rotary position sensor 74 (see FIG. 1A), or an external photogrammetric sensor 76 (see FIG. 1A). The wand controller subsystem 30 may further comprise a surface treatment application element power feedback 62 (see FIG. 1A) coupled to the CPU 60.

The portable wand system 10, for example, the trainable portable wand system 11, further comprises a selector assembly 24 (see FIGS. 1A, 1C) operably coupled to, and activated by, a manual selector button 25 (see FIG. 1A). The step of providing 402 the portable wand system 10, for example, the trainable portable wand system 11, may further comprise, providing the portable wand system 10 having the selector assembly 24 comprising a barcode assembly 348 (see FIG. 1C). As discussed in detail above, the barcode assembly 348 comprises a barcode camera 350 (see FIG. 1C) coupled to the wand applicator 18, decoder electronics 352 (see FIG. 1C) coupled to the wand applicator 18 or to the barcode camera 350, and one or more barcodes 354 (see FIG. 1C) located in one or more of the plurality of stay-in zones 314 and located in one or more of the plurality of stay-out zones 332. The barcode camera 350 is designed to read, and reads, the one or more barcodes 354 located in one or more of the plurality of stay-in zones 314 and located in one or more of the plurality of stay-out zones 332.

In one version, the barcode camera 350 is designed to read, and reads, the two-dimensional barcode 345*a* (see FIG. 1C), e.g., QR (Quick Response) code or matrix barcode, printed on one of, a paper 356 (see FIG. 1C) comprising operator work instructions 358 (see FIG. 1C) for various surface treatment applications 14, and an adjacent surface 360 (see FIG. 1C) adjacent to the one or more surfaces 12 to be surface treated with the surface treatment application 14. The two-dimensional barcode 354*a* may be printed or applied directly or indirectly to the adjacent surface 360, for example, on a label, a decal, or a sticker applied to the adjacent surface 360. The barcode camera 350, or barcode reader, may comprise, in another version, an optical scanner 364 (see FIG. 1C).

The step of providing 402 the portable wand system 10 may further comprise, providing the portable wand system 10, for example, the trainable portable wand system 11, having the selector assembly 24 comprising the RFID assembly 366 (see FIG. 1C) operatively coupled to, and activated by, the manual selector button 25 coupled to the wand applicator 18. As discussed in detail above, the RFID assembly 366 comprises the RFID reader 368 (see FIG. 1C) coupled to the wand applicator 18, RFID electronics 370 (see FIG. 1C) coupled to the wand applicator 18, and RFID tags 372 (see FIG. 1C) located in one or more of the plurality of stay-in zones 314 and located in one or more of the plurality of stay-out zones 332. The RFID reader 368 is designed to read, and reads, one or more of the RFID tags 372 (see FIG. 1C) located in the one or more of the plurality of stay-in zones 314 and located in the one or more of the plurality of stay-out zones 332. The manual selector button 25 may activate the RFID reader 368 with a sequence of clicks or a pattern, for example, with a double click or another suitable sequence of clicks or patterns, for example, by the user 52, or operator 54, double clicking the manual selector button 25, or double clicking the manual selector button 25 in the form of a trigger handle 284 (see FIG. 6A).

The RFID reader 368 and the RFID electronics 370 are operatively coupled to the CPU 60 of the wand controller subsystem 30, and are used with the RFID tags 372, to identify and select one or more zones 308, such as one or more stay-in zones 314, to be surface treated, such as disinfected, and to identify and select one or more zones 308, such as one or more stay-out zones 332, not to be surface treated.

The step of providing 402 the portable wand system 10 may further comprise, providing the portable wand system 10, for example, the trainable portable wand system 11, having the selector assembly 24 comprising the manual selector assembly 374 (see FIG. 1C). The manual selector assembly 374 comprises a manual selection device 376 (see FIG. 1C) coupled to the wand applicator 18, and a prepro-grammed list 378 (see FIG. 1C), or reference list, of iden-tifiers 373 (see FIG. 1C), such as identifying numbers, corresponding to the plurality of stay-in zones 314 and corresponding to the plurality of stay-out zones 332. The manual selector button 25 may activate, or facilitate acti-vating, or using, the manual selection device 376.

In one version, as discussed above, the manual selection device 376 comprises a selection element 380 (see FIG. 1C), such as a series of buttons 380a (see FIG. 1C) on the wand applicator 18 that are manually pressed by the operator 54, or user 52, a touchscreen 380b on the wand applicator 18 that is touched by the operator 54, or user 52, to input identifiers 373 (see FIG. 1C), or another suitable selection element 380 on the wand applicator 18, such as on the handle portion 20 of the wand applicator 18. The selection element 380 is preferably used by the operator 54, or user 52, to identify and select an identifier 373 from the prepro-grammed list 378, that is associated with, or corresponds to, a desired zone 308a, for example, a selected stay-in zone 314a, or a selected stay-out zone 332a, and to recall from the memory unit 66 the selected desired path 310b (see FIG. 1C) associated with the selected stay-in zone 314a and/or the selected stay-out zone path 312b (see FIG. 1C) associated with the one or more selected stay-out zones 332a.

In another version, as discussed above, the manual selec-tion device 376 comprises the keypad device 382 (see FIG. 1C). The keypad device 382 may be coupled to the wand applicator 18, via a wired connection or a wireless connec-tion. The operator 54, or user 52, may type or input one or more identifiers 373, or other information, from the prepro-grammed list 378, into the keypad device 382 to identify and select an identifier 373 associated with, or corresponding to, a desired zone 308a, for example, a selected stay-in zone 314a, or a selected stay-out zone 332a, and to recall from the memory unit 66 the selected desired path 310b (see FIG. 1C) associated with the selected stay-in zone 314a and/or the selected stay-out zone path 312b (see FIG. 1C) associated with the one or more selected stay-out zones 332a.

In yet another version, as discussed above, the manual selection device 376 comprises the separate mobile device 362, such as a smartphone, a tablet computer, or another suitable separate mobile device, having an application 384 (see FIG. 1C) that is designed to communicate with, and communicates with, the portable wand system 10, such as the wand applicator 18, for example, over Wi-Fi, blue tooth, or another suitable wireless connection. The operator 54, or user 52, may type or input one or more identifiers 373, or other information, from the preprogrammed list 378, into the separate mobile device 362 to identify and select an iden-tifier 373 associated with, or corresponding to, a desired zone 308a, for example, a selected stay-in zone 314a, or a selected stay-out zone 332a, and to recall from the memory unit 66 the selected desired path 310b (see FIG. 1C) asso-ciated with the selected stay-in zone 314a and/or the selected stay-out zone path 312b (see FIG. 1C) associated with the one or more selected stay-out zones 332a.

The portable wand system 10, for example, the trainable portable wand system 11, further comprises an indicator element 78. The indicator element 78 comprises a binary indicator 80 (see FIG. 1A) comprising, as shown in FIG. 1A, one of, a light signal 82 coupled to the wand applicator 18, a surface treatment application element flashing light alert 84, an audio alert 86, a sound alert 88, a tactile alert 90, a vibration alert 92, a pulsing alert 94, a pressure altering alert 96, or another suitable alert or alarm. The indicator element 78 indicates to the operator 54, or user 52, that the surface treatment application 14, such as the desired surface treat-ment application 14b, or the predetermined surface treat-ment application 14a, of one or more of the one or more surfaces 12 is complete. In addition, as discussed below, the indicator element 78 indicates to the operator 54, or user 52, that the wand applicator 18 is in proximity to, and oriented towards, one or more of the plurality of stay-out zones 332, and that the wand applicator 18 is in an incorrect position 392.

The portable wand system 10, for example, the trainable portable wand system 11, further comprises a power assem-bly 108 coupled to the wand applicator 18 and the wand controller subsystem 30 in the wand applicator 18. The power assembly 108 may comprise an energy storage device 110 (see FIG. 1A), such as a battery 110a (see FIG. 1A), coupled to the wand applicator 18, via a wired connector 114 (see FIG. 1A).

The step of providing 402 the portable wand system 10 may further comprise, providing the portable wand system 10, for example, the trainable portable wand system 11, comprising a computer recording system 136 (see FIG. 1A) coupled to the wand controller subsystem 30. The computer recording system 136 analyzes the positional data 58 of the wand applicator 18, and communicates to the indicator element 78 a status 15 (see FIG. 1B) of the surface treatment application 14 (see FIG. 1B), such as the predetermined surface treatment application 14a (see FIG. 1B), or the desired surface treatment application 14b (see FIG. 1C) on the one or more surfaces 12. The computer recording system 136 comprises a computer 138 (see FIG. 1A) to record the surface treatment application 14, such as the predetermined surface treatment application 14a, or the desired surface treatment application 14b, of the one or more surfaces 12, to validate and verify that the surface treatment application 14, such as the predetermined surface treatment application 14a, or desired surface treatment application 14b, of the one or more surfaces 12 is correct.

As shown in FIG. 7, the method 400 further comprises the step of training 404 the portable wand system 10, for example, the trainable portable wand system 11, in a learn mode 300 (see FIG. 1C), to learn a plurality of paths 304 (see FIG. 1C), by the operator 54 (see FIG. 1A), or user 52 (see FIG. 1A), initially manually moving the wand applicator 18 in the plurality of paths 304 comprising a plurality of desired paths 310 (see FIG. 1C) in a plurality of stay-in zones 314 (see FIG. 1C) having one or more surfaces 12 to be surface treated with a surface treatment application 14, and by the operator 54, or user 52, then manually moving the wand applicator 18 in the plurality of paths 304 comprising a plurality of stay-out zone paths 312 (see FIG. 1C) in, or near, a plurality of stay-out zones 332 (see FIG. 1C) not to be surface treated. Once the trainable portable wand system 11 is trained with the learn mode 300, the trainable portable wand system 11 can be considered, or becomes, a trained portable wand system IIa (see FIG. 1C).

The step of training 404 the portable wand system 10, for example, the trainable portable wand system 11, in the learn mode 300, by manually moving the wand applicator 18 in the plurality of desired paths 310 (see FIG. 1C) in the plurality of stay-in zones 314 (see FIG. 1C) having one or more surfaces 12 to be surface treated, further comprises, manually moving the wand applicator 18 in the plurality of desired paths 310 in the plurality of stay-in zones 314 having one or more surfaces 12 comprising one or more surfaces 12 in an interior 146, as shown in FIG. 1B, of one of, an aircraft 148, a spacecraft 150, an automotive vehicle 152, a watercraft 154, a train 156, a hospital 158, a factory building 160, an office building 162, a movie theater 164, a restaurant 166, or another suitable vehicle or structure.

The method 400 may further comprise before the step of training 404 the portable wand system 10, for example, the trainable portable wand system 11, in the learn mode 300, the step of selecting, with the manual selector button 25, a learn mode selection 342 (see FIG. 1C), to activate the portable wand system 10, including the wand applicator 18, in the learn mode 300. In addition, before manually moving the wand applicator 18 in the plurality of desired paths 310 in the plurality of stay-in zones 314, a stay-in zone learn mode selection 342a (see FIG. 1C) may be selected with the manual selector button 25. In addition, before manually moving the wand applicator 18 in the plurality of stay-out zone paths 312 in, over, or near, the plurality of stay-out zones 332, a stay-out zone learn mode selection 342b (see FIG. 1C) may be selected with the manual selector button 25.

As shown in FIG. 7, the method 400 further comprises the step of recording and storing 406, with the portable wand system 10, the plurality of desired paths 310 corresponding, respectively, to the plurality of stay-in zones 314, and recording and storing, with the portable wand system 10, the plurality of stay-out zone paths 312 corresponding, respectively, to the plurality of stay-out zones 332. The CPU 60 records the plurality of paths 304, such as the plurality of desired paths 310 and the plurality of stay-out zone paths 312, learned during the learn mode 300. The memory unit 66 of the wand controller subsystem 30 stores the plurality of paths 304, such as the plurality of desired paths 310 and the plurality of stay-out zone paths 312, learned during the learn mode 300.

As shown in FIG. 7, the method 400 further comprises the step of selecting 408, with the portable wand system 10, for example, the trained portable wand system 11a, and in particular, with the selector assembly 24, a selected stay-in zone 314a having the one or more surfaces 12 to be surface treated, and selecting the desired path 310 corresponding to the selected stay-in zone 314a.

As shown in FIG. 7, the method 400 further comprises the step of operating 410 the portable wand system 10, for example, the trained portable wand system 11a, in an operation mode 302 (see FIG. 1C), by the operator 54, or user 52, manually moving the wand applicator 18 in an operation path 386 (see FIG. 1C), based on, and corresponding or substantially corresponding, to the desired path 310 (see FIG. 1C), in the selected stay-in zone 314a, with the surface treatment application element 16 activated. The operation path 386 is measured with positional data 58 (see FIG. 1A) of the wand applicator 18 in real-time.

The method 400 may further comprise, before the step of operating 410 the portable wand system 10, for example, the trained portable wand system 11a, in the operating mode 302, the step of selecting, with the manual selector button 25, an operation mode selection 344 (see FIG. 1C), to activate the portable wand system 10 in the operation mode 302.

The method 400 may further comprise, before the step of selecting 408 the selected stay-in zone 314a, or before the step of operating 410 the portable wand system 10 in the operation mode 302, the step of pressing the manual selector button 25, to identify, with a registration feature 130 (see FIG. 1A), a starting position 167 (see FIG. 4A) at one of the one or more surfaces 12 to be surface treated in the selected stay-in zone 314a. The registration feature 130 registers the wand applicator 18 against a known location 132 (see FIG. 1A) on one of the one or more surfaces 12 in the selected stay-in zone 314a.

As shown in FIG. 7, the method 400 further comprises the step of comparing 412, with the portable wand system 10, for example, the trained portable wand system 11a, and in particular, comparing using the computer program 32, or algorithm 32a, of the CPU 60 of the portable wand system 10, the operation path 386 to the desired path 310 to see if there is a deviation 387 (see FIG. 1C) of the operation path 386 from the desired path 310.

As shown in FIG. 7, the method 400 further comprises the step of indicating 414 to the operator 54, or user 52, with the portable wand system 10, for example, the trained portable wand system 11a, when the operation path 386 deviates from the desired path 310, and when the wand applicator 18 is in proximity to, and oriented towards, one or more of the plurality of stay-out zones 332, to allow for adjusting the movement 388 (see FIG. 1C) of the wand applicator 18 and adjusting the power 121 (see FIG. 1A) to the wand applicator 18, such as the power 121 to the surface treatment application element 16 of the wand applicator 18.

The step of indicating 414 when the wand applicator 18 is in proximity to, and oriented towards, one or more of the plurality of stay-out zones 332, further comprises, indicating when the wand applicator 18 is in proximity to, and oriented towards, one or more of the plurality of stay-out zones 332, to allow for adjusting the power 121 to the wand applicator 18, by the computer program 32 (see FIG. 1A), such as the algorithm 32a (see FIG. 1A), providing a feedback signal 390 (see FIG. 1C) to the power assembly 108, to cause the power assembly 108 to reduce the power 121, or to extinguish the power 121, to the surface treatment application element 16 of the wand applicator 18.

The step of indicating 414 when the wand applicator 18 is in proximity to, and oriented towards, one or more of the plurality of stay-out zones 332, further comprises, indicating when the wand applicator 18 is in proximity to, and oriented towards, one or more of the plurality of stay-out zones 332, to allow for adjusting the movement 388 (see FIG. 1C) of the wand applicator 18, by the computer program 32 triggering the indicator element 78 to notify the operator 54, or user 52, of an incorrect position 392 (see FIG. 1C) of the wand applicator 18. The indicator element 78 comprises the binary indicator 80, and examples of the binary indicator 80 are discussed above, and shown in FIG. 1A.

As shown in FIG. 7, the method 400 further comprises the step of verifying 416, with the portable wand system 10, for example, the trained portable wand system 11a, that the desired surface treatment application 14b is achieved for the one or more surfaces 12 in the selected stay-in zone 314a.

The step of verifying 416 that the desired surface treatment application 14b is achieved further comprises, verifying 416 that the desired surface treatment application 14b is achieved, where the desired surface treatment application 14*b* comprises a surface treatment application 14, such as one of, as shown in FIG. 1B, a disinfection operation 168, an ultraviolet (UV) light disinfection operation 170, a decontamination operation 174, a sanitization operation 176, a sterilization operation 178, a curing operation 180, a shot peening operation 182, a chemical contaminant detection operation 184, a biological contaminant detection operation 186, a non-destructive inspection process 188, an eddy current crack detection 190, a paint application 192, an abrasive media blasting operation 194, a sand blasting operation 194*a*, a surface pre-heating operation 196, a torch welding operation 198, or another suitable surface treatment application.

The step of verifying 416 that the desired surface treatment application 14*b* is achieved for the selected stay-in zone 314*a* may further comprise activating, with the portable wand system 10, the indicator element 78 (see FIG. 1A) to signal to the operator 54, or user 52, that the desired surface treatment application 14*b*, or a predetermined surface treatment application 14*a*, is achieved with the surface treatment application element 16 for the one or more surfaces 12 that are surface treated. As discussed above, the indicator element 78 comprises a binary indicator 80 comprising, as shown in FIG. 1A, one of, a light signal 82 coupled to the wand applicator 18, a surface treatment application element flashing light alert 84, an audio alert 86, a sound alert 88, a tactile alert 90, a vibration alert 92, a pulsing alert 94, a pressure altering alert 96, or another suitable alert or alarm, to indicate that the surface treatment application 14, such as the predetermined surface treatment application 14*a*, or the desired surface treatment application 14*b*, of one or more of the one or more surfaces 12 is complete.

The step of verifying 416 that the desired surface treatment application 14*b* is achieved for the selected stay-in zone 314*a* may further comprise activating the indicator element 78 to signal to the operator 54, or user 52, that the desired surface treatment application 14*b*, or predetermined surface treatment application 14*a*, is achieved, may further comprise activating the indicator element 78 comprising a video display 98 (see FIG. 1A) coupled to the wand applicator 18. The video display 98 is visible to the operator 54, or the user 52, and shows one or more of, portions 102 (see FIG. 1A) of the one or more surfaces 12 to be surface treated, and a color coded signal 104 (see FIG. 1A), comprising a lighted progress bar 106 (see FIG. 1A), to indicate which portions 102 have complete coverage, that is, complete coverage portions 102*a* (see FIG. 1A).

The method 400 may further comprise, after verifying 416 that the desired surface treatment application 14*b* for the selected stay-in zone 314*a* is achieved, the steps of, moving the portable wand system 10, such as the trained portable wand system 11*a*, to a subsequent known location 132*a* (see FIG. 1A), to register the portable wand system 10 at the subsequent known location 132*a*, and performing the step of selecting a subsequent selected stay-in zone 314*b* (see FIG. 1C) to be surface treated and selecting the desired path 310 corresponding to the subsequent selected stay-in zone 314*b*, and repeating the step of operating the portable wand system 10, such as the trained portable wand system 11*a*, in the operation mode 302, by the operator 54, or user 52, manually moving the wand applicator 18 in an operation path 386, based on, and corresponding, or substantially corresponding, to the desired path 310 in the subsequent selected stay-in zone 314*b*, repeating the step of comparing 412 the operation path 386 to the desired path 310, repeating the step of indicating 414 when the operation path 386 deviates from the desired path 310, and repeating the step of verifying 416 the desired surface treatment application 14*b* is achieved.

Now referring to FIG. 8, FIG. 8 is an illustration of a flow diagram of a version of a method 450 of the disclosure. In another version of the disclosure, there is provided the method 450 to indicate and verify to an operator 54, or a user 52, that a desired ultraviolet (UV) light disinfection 172*b* (see FIG. 1B) is achieved for one or more surfaces 12 in an interior 146 (see FIG. 1B) of an aircraft 148 (see FIG. 1B) to be disinfected.

The blocks in FIG. 8 represent operations and/or portions thereof, or elements, and lines connecting the various blocks do not imply any particular order or dependency of the operations or portions thereof, or elements. FIG. 8 and the disclosure of the steps of the method 450 set forth herein should not be interpreted as necessarily determining a sequence in which the steps are to be performed. Rather, although one illustrative order is indicated, it is to be understood that the sequence of the steps may be modified when appropriate. Accordingly, certain operations may be performed in a different order or simultaneously.

As shown in FIG. 8, the method 450 comprises the step of providing 452 a version of a portable wand system 10 (see FIGS. 1A, 2A-2B, 3A-3B, 5B), for example, a trainable portable wand system 11 (see FIGS. 1A, 1C). As discussed in detail above, in one version, the portable wand system 10, for example, the trainable portable wand system 11, comprises a wand applicator 18 (see FIG. 1A) containing an ultraviolet (UV) lamp element 26 (see FIG. 1A).

The portable wand system 10, for example, the trainable portable wand system 11, further comprises a wand controller subsystem 30 (see FIG. 1A) coupled to the wand applicator 18. The wand controller subsystem 30 comprises a computer program 32 (see FIG. 1A), such as an algorithm 32*a* (see FIG. 1A), a memory unit 66 (see FIG. 1A), and a central processing unit (CPU) 60 (see FIG. 1A) coupled to the memory unit 66. The wand controller subsystem 30 may further comprise in one version, an inertial measurement unit (IMU) 42 (see FIG. 1A) coupled to the CPU 60, or in another version, one or more of, a fixed position extensometer 72 (see FIG. 1A), a rotary position sensor 74 (see FIG. 1A), or an external photogrammetric sensor 76 (see FIG. 1A). The wand controller subsystem 30 may further comprise a surface treatment application element power feedback 62 (see FIG. 1A) coupled to the CPU 60.

The portable wand system 10, for example, the trainable portable wand system 11, further comprises a selector assembly 24 operably coupled to, and activated by, the manual selector button 25. The step of providing 452 the portable wand system 10, for example, the trainable portable wand system 11, may further comprise, providing the portable wand system 10 having the selector assembly 24 comprising a barcode assembly 348 (see FIG. 1C). As discussed in detail above, the barcode assembly 348 comprises a barcode camera 350 (see FIG. 1C) coupled to the wand applicator 18, decoder electronics 352 (see FIG. 1C) coupled to the wand applicator 18 or to the barcode camera 350, and one or more barcodes 354 (see FIG. 1C) located in one or more of the plurality of stay-in zones 314 and located in one or more of the plurality of stay-out zones 332. The barcode camera 350 is designed to read, and reads, the one or more barcodes 354 located in one or more of the plurality of stay-in zones 314 and located in one or more of the plurality of stay-out zones 332.

In one version, the barcode camera 350 is designed to read, and reads, a two-dimensional barcode 345*a* (see FIG. 1C), e.g., QR (Quick Response) code or matrix barcode, printed on one of, a paper 356 (see FIG. 1C) comprising operator work instructions 358 (see FIG. 1C) for various surface treatment applications 14, and an adjacent surface 360 (see FIG. 1C) adjacent to the one or more surfaces 12 to be surface treated with the surface treatment application 14. The two-dimensional barcode 354a may be printed or applied directly or indirectly to the adjacent surface 360, for example, on a label, a decal, or a sticker applied to the adjacent surface 360. The barcode camera 350, or barcode reader, may comprise, in another version, an optical scanner 364 (see FIG. 1C).

The step of providing 452 the portable wand system 10 may further comprise, providing the portable wand system 10, for example, the trainable portable wand system 11, having the selector assembly 24 comprising the radio frequency identification (RFID) assembly 366 (see FIG. 1C) operatively coupled to, and activated by, the manual selector button 25 coupled to the wand applicator 18. As discussed in detail above, the RFID assembly 366 comprises the radio frequency identification (RFID) reader 368 (see FIG. 1C) coupled to the wand applicator 18, radio frequency identification (RFID) electronics 370 (see FIG. 1C) coupled to the wand applicator 18, and (RFID) tags 372 (see FIG. 1C) located in one or more of the plurality of stay-in zones 314 and located in one or more of the plurality of stay-out zones 332. The RFID reader 368 is designed to read, and reads, one or more of the radio frequency identification (RFID) tags 372 (see FIG. 1C) located in the one or more of the plurality of stay-in zones 314 and located in the one or more of the plurality of stay-out zones 332. The manual selector button 25 may activate the RFID reader 368 with a sequence of clicks or a pattern, for example, with a double click or another suitable sequence of clicks or patterns, for example, by the user 52, or operator 54, double clicking the manual selector button 25, or double clicking the manual selector button 25 in the form of a trigger handle 284 (see FIG. 6A). The RFID reader 368 and the RFID electronics 370 are operatively coupled to the CPU 60 of the wand controller subsystem 30, and are used with the RFID tags 372, to identify and select one or more zones 308, such as one or more stay-in zones 314, to be surface treated, such as disinfected, and to identify and select one or more zones 308, such as one or more stay-out zones 332, not to be surface treated.

The step of providing 452 the portable wand system 10 may further comprise, providing the portable wand system 10, for example, the trainable portable wand system 11, having the selector assembly 24 comprising the manual selector assembly 374 (see FIG. 1C). The manual selector assembly 374 comprises a manual selection device 376 (see FIG. 1C) coupled to the wand applicator 18, and a preprogrammed list 378 (see FIG. 1C), or reference list, of identifiers 373 (see FIG. 1C), such as identifying numbers, corresponding to the plurality of stay-in zones 314 and corresponding to the plurality of stay-out zones 332. The manual selector button 25 may activate, or facilitate activating, or using, the manual selection device 376.

In one version, as discussed above, the manual selection device 376 comprises a selection element 380 (see FIG. 1C), such as a series of buttons 380a (see FIG. 1C) on the wand applicator 18 that are manually pressed by the operator 54, or user 52, a touchscreen 380b on the wand applicator 18 that is touched by the operator 54, or user 52, to input identifiers 373 (see FIG. 1C), such as numeric or alphanumeric, or another suitable selection element 380 on the wand applicator 18, such as on the handle portion 20 of the wand applicator 18. The selection element 380 is preferably used by the operator 54, or user 52, to identify and select an identifier 373 from the preprogrammed list 378, that is associated with, or corresponds to, a desired zone 308a, for example, a selected stay-in zone 314a, or a selected stay-out zone 332a, and to recall from the memory unit 66 the selected desired path 310b (see FIG. 1C) associated with the selected stay-in zone 314a and/or the selected stay-out zone path 312b (see FIG. 1C) associated with the one or more selected stay-out zones 332a.

In another version, as discussed above, the manual selection device 376 comprises the keypad device 382 (see FIG. 1C). The keypad device 382 may be coupled to the wand applicator 18, via a wired connection or a wireless connection. The operator 54, or user 52, may type or input one or more identifiers 373, or other information, from the preprogrammed list 378, into the keypad device 382 to identify and select an identifier 373 associated with, or corresponding to, a desired zone 308a, for example, a selected stay-in zone 314a, or a selected stay-out zone 332a, and to recall from the memory unit 66 the selected desired path 310b (see FIG. 1C) associated with the selected stay-in zone 314a and/or the selected stay-out zone path 312b (see FIG. 1C) associated with the one or more selected stay-out zones 332a.

In yet another version, as discussed above, the manual selection device 376 comprises the separate mobile device 362, such as a smartphone, a tablet computer, or another suitable separate mobile device, having an application 384 (see FIG. 1C) that is designed to communicate with, and communicates with, the portable wand system 10, such as the wand applicator 18, for example, over Wi-Fi, blue tooth, or another suitable wireless connection. The operator 54, or user 52, may type or input one or more identifiers 373, or other information, from the preprogrammed list 378, into the separate mobile device 362 to identify and select an identifier 373 associated with, or corresponding to, a desired zone 308a, for example, a selected stay-in zone 314a, or a selected stay-out zone 332a, and to recall from the memory unit 66 the selected desired path 310b (see FIG. 1C) associated with the selected stay-in zone 314a and/or the selected stay-out zone path 312b (see FIG. 1C) associated with the one or more selected stay-out zones 332a.

The portable wand system 10, for example, the trainable portable wand system 11, further comprises the indicator element 78. The indicator element 78 comprises the binary indicator 80 (see FIG. 1A) comprising, as shown in FIG. 1A, one of, a light signal 82 coupled to the wand applicator 18, a surface treatment application element flashing light alert 84, an audio alert 86, a sound alert 88, a tactile alert 90, a vibration alert 92, a pulsing alert 94, a pressure altering alert 96, or another suitable alert or alarm. The indicator element 78 indicates to the operator 54, or user 52, that the desired ultraviolet (UV) light disinfection 172b, such as the predetermined UV light disinfection 172a, of one or more of the one or more surfaces 12 is complete. In addition, as discussed below, the indicator element 78 indicates to the operator 54, or user 52, that the wand applicator 18 is in proximity to, and oriented towards, one or more of the plurality of stay-out zones 332 to be avoided, and that the wand applicator 18 is in an incorrect position 392.

The portable wand system 10, for example, the trainable portable wand system 11, further comprises the power assembly 108 coupled to the wand applicator 18, and in particular, to the wand controller subsystem 30 in the wand applicator 18. The power assembly 108 may comprise an energy storage device 110 (see FIG. 1A), such as a battery 110a (see FIG. 1A), coupled to the wand applicator 18, via a wired connector 114 (see FIG. 1A).

The step of providing 452 the portable wand system 10 may further comprise, providing the portable wand system 10, for example, the trainable portable wand system 11, comprising the computer recording system 136 (see FIG. 1A) coupled to the wand controller subsystem 30. The computer recording system 136 analyzes the positional data 58 of the wand applicator 18, and communicates to the indicator element 78 a status 15 (see FIG. 1B) of the surface treatment application 14 (see FIG. 1B), such as the predetermined surface treatment application 14a (see FIG. 1B), or the desired surface treatment application 14b (see FIG. 1C) on the one or more surfaces 12. The computer recording system 136 comprises the computer 138 (see FIG. 1A) to record the UV light disinfection 172, such as the desired UV light disinfection 172b, or the predetermined UV light disinfection 172a, of the one or more surfaces 12, to validate and verify that the UV light disinfection 172, such as the desired UV light disinfection 172b, or the predetermined UV light disinfection 172a is correct.

As shown in FIG. 8, the method 450 further comprises the step of selecting 454, with the manual selector button 25 a learn mode selection 342 (see FIG. 1C), to activate the portable wand system 10 in a learn mode 300. The step of selecting 454 may further comprise selecting, using the selector assembly 24, a selected stay-in zone 314a from a plurality of stay-in zones 314 having one or more surfaces 12 to be disinfected with a disinfection operation 168 (see FIG. 1B) of the UV lamp element 26, such as a UV light disinfection 172 (see FIG. 1B).

As shown in FIG. 8, the method 450 further comprises the step of training 456 the portable wand system 10, for example, the trainable portable wand system 11, in a first learn mode 300a (see FIG. 1C) of the learn mode 300, by an operator 54, or user 52, initially manually moving the wand applicator 18 in a plurality of desired paths 310 in a plurality of stay-in zones 314 having one or more surfaces 12 to be disinfected with the UV lamp element 26, to obtain the UV light disinfection 172, such as the desired UV light disinfection 172b. In addition, before manually moving the wand applicator 18 in the plurality of desired paths 310 in the plurality of stay-in zones 314, a stay-in zone learn mode selection 342a (see FIG. 1C) may be selected with the manual selector button 25.

As shown in FIG. 8, the method 450 further comprises the step of recording and storing 458, with the portable wand system 10, for example, the trainable portable wand system 11, the plurality of desired paths 310 corresponding, respectively, to the plurality of stay-in zones 314. The CPU 60 records, in real-time, the plurality of desired paths 310, learned during the first learn mode 300a. The memory unit 66 of the wand controller subsystem 30 stores, preferably in real-time, the plurality of desired paths 310, learned during the first learn mode 300a.

As shown in FIG. 8, the method 450 further comprises the step of training 460 the portable wand system 10, for example, the trainable portable wand system 11, in a second learn mode 300b (see FIG. 1C), by the operator 54, or the user 52, manually moving the wand applicator 18 in one or more stay-out zone paths 312 (see FIG. 1C) in, over, or near, a plurality of stay-out zones 332 (see FIG. 1C) not to be disinfected. Before the step of training 460 the portable wand system 10, the step of selecting 454 may further comprise selecting, using the selector assembly 24, and in particular, using the manual selector button 25, a selected stay-out zone 332a from the plurality of stay-out zones 332 to be avoided with the disinfection operation 168, such as the UV light disinfection 172. In addition, before manually moving the wand applicator 18 in the plurality of stay-out zone paths 312 in, over, or near, the plurality of stay-out zones 332, a stay-out zone learn mode selection 342b (see FIG. 1C) may be selected with the manual selector button 25.

As shown in FIG. 8, the method 450 further comprises the step of recording and storing 462, with the portable wand system 10, for example, the trainable portable wand system 11, the plurality of stay-out zone paths 312 corresponding, respectively, to the plurality of stay-out zones 332. The CPU 60 records, in real-time, the plurality of stay-out zone paths 312, learned during the second learn mode 300b. The memory unit 66 of the wand controller subsystem 30 stores, preferably in real-time, the plurality of stay-out zone paths 312, learned during the second learn mode 300b.

After training the portable wand system 10 to learn a desired path 310 in a selected stay-in zone 314a, or after the step of training 460 the portable wand system 10 to learn a stay-out zone path 312 in a selected stay-out zone 332a, additional desired paths 310 may be learned in subsequent selected stay-in zones 314b (see FIG. 1C), and the additional desired paths 310 may be recorded by the CPU 60 and stored in the memory unit 66. After training the portable wand system 10 to learn a stay-out zone path 312 in a selected stay-out zone 332a, or after the step of learning an additional desired path 310 in a subsequent selected stay-in zone 314b, additional stay-out zone paths 312 may be learned in subsequent selected stay-out zones 332b (see FIG. 1C), and the additional stay-out zone paths 312 may be recorded by the CPU 60 and stored in the memory unit 66. Once the trainable portable wand system 11 is trained with the learn mode 300 comprising the first learn mode 300a and the second learn mode 300b, the trainable portable wand system 11 may be considered, or comprises, a trained portable wand system 11a (see FIG. 1C).

As shown in FIG. 8, the method 450 further comprises the step of selecting 464, with the manual selector button 25, an operation mode selection 344 (see FIG. 1C), to activate the portable wand system 10 to enter into an operation mode 302 (see FIG. 1C). As shown in FIG. 8, the method 450 further comprises the step of selecting 466, with the selector assembly 24, a selected stay-in zone 314a having the one or more surfaces 12 to be disinfected, and selecting the desired path 310, recorded and stored in the first learn mode 300a, corresponding to the selected stay-in zone 314a.

As shown in FIG. 8, the method 450 further comprises the step of operating 468 the portable wand system 10, for example, the trained portable wand system 11a, in the operation mode 302 (see FIG. 1C), by the operator 54, or user 52, manually moving the wand applicator 18, in real-time, in an operation path 386 (see FIG. 1C), based on, and corresponding, or substantially corresponding, to the desired path 310, in the selected stay-in zone 314a, with the UV lamp element 26 activated. Each operation path 386 is measured with positional data 58 (see FIG. 1A) of the wand applicator 18 in real-time.

The method 450 may further comprise, before the step of selecting 466 the selected stay-in zone 314a, or before the step of operating 468 the portable wand system 10 in the operation mode 302, the step of pressing the manual selector button 25, to identify, with a registration feature 130 (see FIG. 1A), a starting position 167 (see FIG. 4A) at one of the one or more surfaces 12 to be disinfected in the selected stay-in zone 314a. The registration feature 130 registers the wand applicator 18 against a known location 132 (see FIG. 1A) on one of the one or more surfaces 12 in the selected stay-in zone 314a.

As shown in FIG. 8, the method 450 further comprises the step of comparing 470, with the portable wand system 10, for example, the trained portable wand system 11*a*, and in particular, comparing using the CPU 60 of the portable wand system 10, the operation path 386 to the desired path 310 to see if there is a deviation 387 of the operation path 386 from the desired path 310.

As shown in FIG. 8, the method 450 further comprises the step of indicating 472 to the operator 54, or user 52, with the portable wand system 10, for example, the trained portable wand system 11*a*, when the operation path 386 deviates from the desired path 310, and when the wand applicator 18 is in proximity to, and oriented towards, one or more of the plurality of stay-out zones 332, to allow for adjusting the movement 388 (see FIG. 1C) of the wand applicator 18 and adjusting the power 121 (see FIG. 1A) to the wand applicator 18, such as the power 121 to the UV lamp element 26 of the wand applicator 18.

The step of indicating 472 when the wand applicator 18 is in proximity to, and oriented towards, one or more of the plurality of stay-out zones 332, further comprises, indicating when the wand applicator 18 is in proximity to, and oriented towards, one or more of the plurality of stay-out zones 332, to allow for adjusting the power 121 to the wand applicator 18, by the computer program 32 (see FIG. 1A), such as the algorithm 32*a* (see FIG. 1A), providing a feedback signal 390 (see FIG. 1C) to the power assembly 108, to cause the power assembly 108 to reduce the power 121, or to extinguish the power 121, to the UV lamp element 26 of the wand applicator 18.

The step of indicating 472 when the wand applicator 18 is in proximity to, and oriented towards, one or more of the plurality of stay-out zones 332, further comprises, indicating when the wand applicator 18 is in proximity to, and oriented towards, one or more of the plurality of stay-out zones 332, to allow for adjusting the movement 388 of the wand applicator 18, by the computer program 32 triggering the indicator element 78 to notify the operator 54, or user 52, of an incorrect position 392 of the wand applicator 18. The indicator element 78 comprises the binary indicator 80, and examples of the binary indicator 80 are shown in FIG. 1A.

As shown in FIG. 8, the method 450 further comprises the step of verifying 474, with the portable wand system 10, for example, the trained portable wand system 11*a*, that the desired UV light disinfection 172*b* is achieved for the one or more surfaces 12 in the selected stay-in zone 314*a*. The step of verifying 474 that the desired UV light disinfection 172*b* is achieved for the selected stay-in zone 314*a* may further comprise activating, with the portable wand system 10, the indicator element 78 (see FIG. 1A) to signal to the operator 54, or user 52, that the desired UV light disinfection 172*b*, or the predetermined UV light disinfection 172*a*, is achieved with the UV lamp element 26 for the one or more surfaces 12 that are disinfected. As discussed above, the indicator element 78 comprises the binary indicator 80 comprising, as shown in FIG. 1A, one of, a light signal 82 coupled to the wand applicator 18, a surface treatment application element flashing light alert 84, an audio alert 86, a sound alert 88, a tactile alert 90, a vibration alert 92, a pulsing alert 94, a pressure altering alert 96, or another suitable alert or alarm, to indicate that the surface treatment application 14, such as the predetermined surface treatment application 14*a*, of one or more of the one or more surfaces 12 is complete.

The step of verifying 474 that the desired UV light disinfection 172*b* is achieved for the selected stay-in zone 314*a* may further comprise activating the indicator element 78 to signal to the operator 54, or user 52, that the desired UV light disinfection 172*b*, or predetermined UV light disinfection 172*a*, is achieved, may further comprise activating the indicator element 78 comprising a video display 98 (see FIG. 1A) coupled to the wand applicator 18. The video display 98 is visible to the operator 54, or the user 52, and shows one or more of, portions 102 (see FIG. 1A) of the one or more surfaces 12 to be surface treated, and a color coded signal 104 (see FIG. 1A), comprising a lighted progress bar 106 (see FIG. 1A), to indicate which portions 102 have complete coverage, that is, complete coverage portions 102*a* (see FIG. 1A).

The method 450 may further comprise, after verifying 474 that the desired surface treatment application 14*b* for the selected stay-in zone 314*a* is achieved, the steps of, moving the portable wand system 10, such as the trained portable wand system 11*a*, to a subsequent known location 132*a* (see FIG. 1A), to register the portable wand system 10 at the subsequent known location 132*a*, and performing the step of selecting a subsequent selected stay-in zone 314*b* (see FIG. 1C) to be disinfected and selecting the desired path 310 corresponding to the subsequent selected stay-in zone 314*b*, and repeating the step of operating the portable wand system 10, such as the trained portable wand system 11*a*, in the operation mode 302, by the operator 54, or user 52, manually moving the wand applicator 18 in an operation path 386, based on, and corresponding, or substantially corresponding, to the desired path 310 in the subsequent selected stay-in zone 314*b*, repeating the step of comparing 470 the operation path 386 to the desired path 310, repeating the step of indicating 472 when the operation path 386 deviates from the desired path 310, and repeating the step of verifying 474 the desired surface treatment application 14*b* is achieved.

Figure 9:
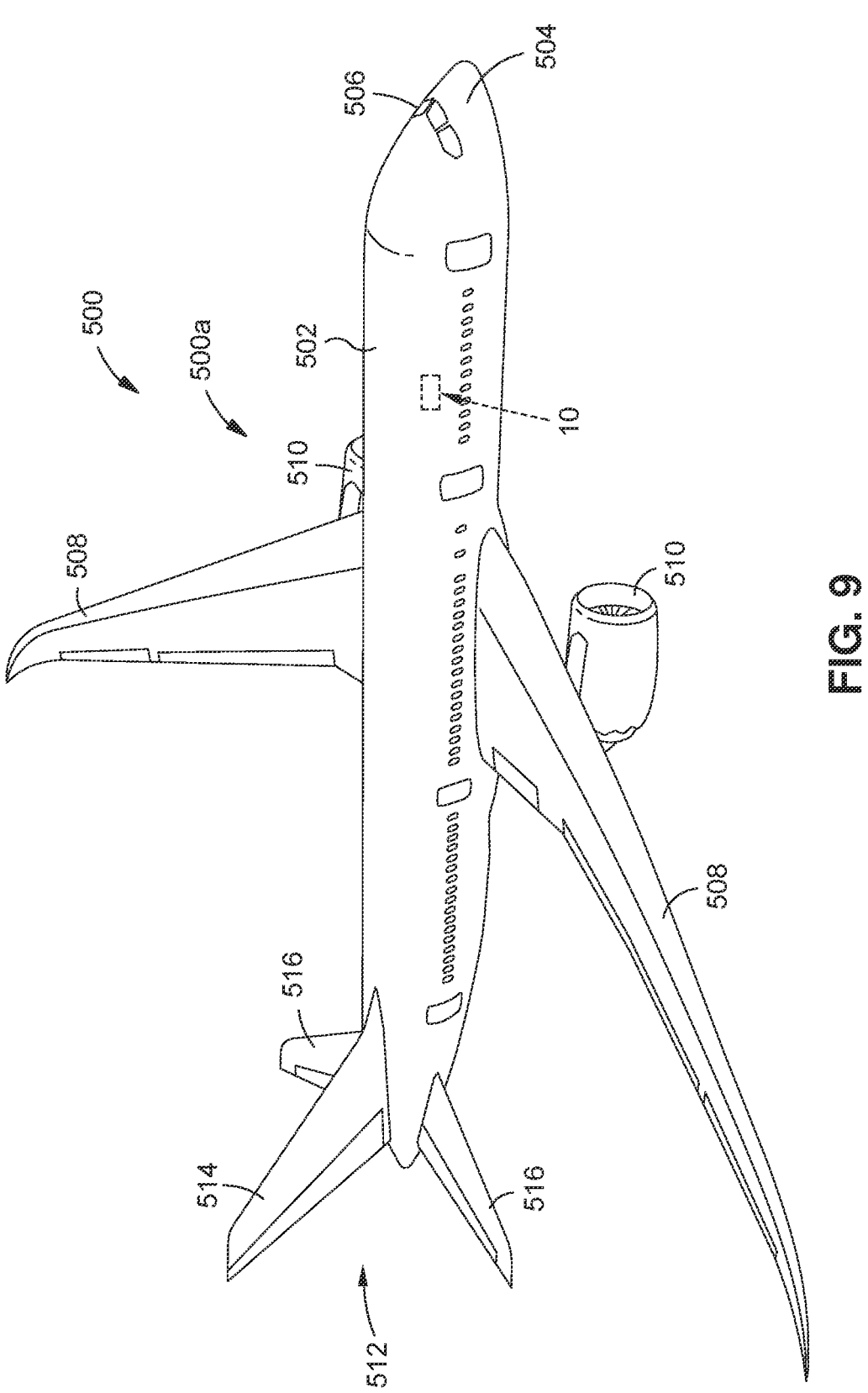
FIG. 9 is an illustration of a perspective view of an aircraft that may use a portable wand system of the disclosure.

Now referring to FIG. 9, FIG. 9 is an illustration of a perspective view of an air vehicle 500, such as an aircraft 500*a*, that may use a version of a portable wand system 10 (see FIG. 1A), for example, the trainable portable wand system 11 (see FIG. 1C), and the trained portable wand system 11*a* (see FIG. 1C), of the disclosure. As shown in FIG. 9, the air vehicle 500, such as the aircraft 500*a*, includes a fuselage 502, a nose 504, a flight deck 506 or cockpit, wings 508, engines 510, and a tail 512. As shown in FIG. 9, the tail 512 comprises a vertical stabilizer portion 514, and horizontal stabilizer portions 516. The portable wand system 10, for example, the trained portable wand system 11*a*, may be used to disinfect, sanitize, sterilize, or perform another surface treatment application 14 on various surfaces, structures, objects, and components within the aircraft 500*a*, including inside the flight deck 506, or cockpit, inside the cabin 246 (see FIGS. 4A, 4C), inside a galley area, inside a bathroom, inside a closet, and inside and outside of overhead stowage bins 330 (see FIG. 4C).

Figures 10, 11:
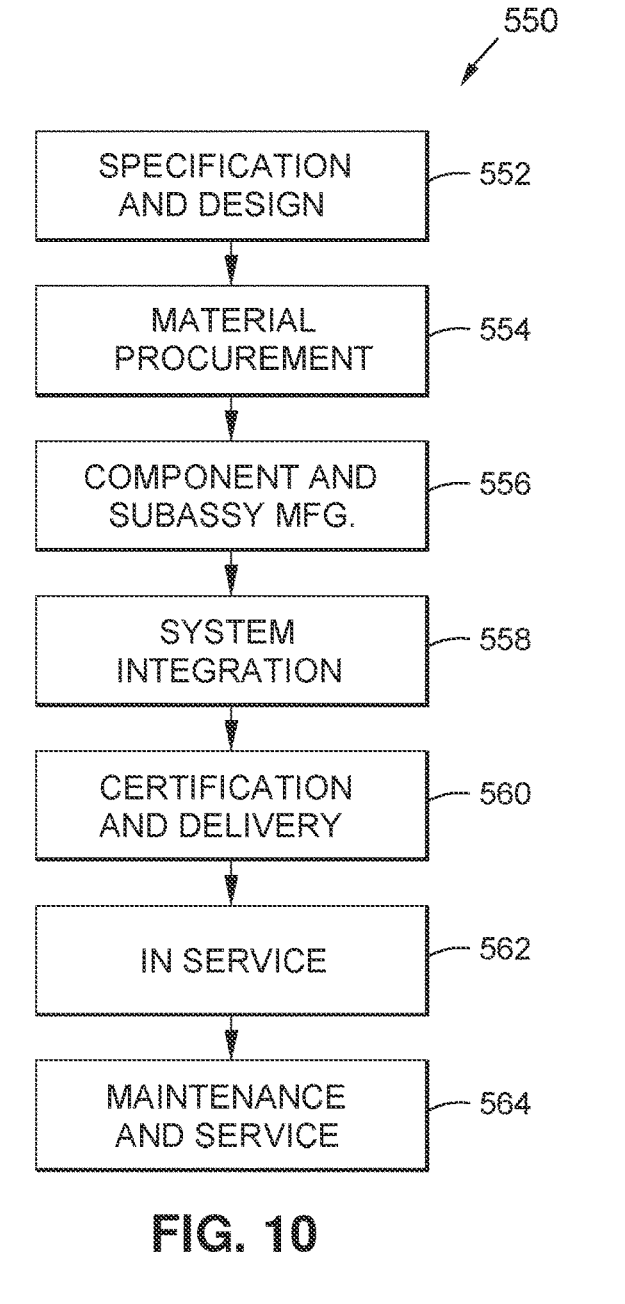
FIG. 10 is an illustration of a flow diagram of an exemplary aircraft manufacturing and service method.
FIG. 11 is an illustration of an exemplary block diagram of an aircraft.

Now referring to FIGS. 10 and 11, FIG. 10 is an illustration of a flow diagram of an exemplary aircraft manufacturing and service method 550, and FIG. 11 is an illustration of an exemplary block diagram of an aircraft 566. Referring to FIGS. 10 and 11, versions of the disclosure may be described in the context of the aircraft manufacturing and service method 550 as shown in FIG. 10, and the aircraft 566 as shown in FIG. 11.

During pre-production, exemplary aircraft manufacturing and service method 550 may include specification and design 552 of the aircraft 566 and material procurement 554. During manufacturing, component and subassembly manufacturing 556 and system integration 558 of the aircraft 566 takes place. Thereafter, the aircraft 566 may go through certification and delivery 560 in order to be placed in service 562. While in service 562 by a customer, the aircraft 566 may be scheduled for routine maintenance and service 564 (which may also include modification, reconfiguration, refurbishment, and other suitable services).

Each of the processes of the aircraft manufacturing and service method 550 may be performed or carried out by a system integrator, a third party, and/or an operator (e.g., a customer). For the purposes of this description, a system integrator may include, without limitation, any number of aircraft manufacturers and major-system subcontractors. A third party may include, without limitation, any number of vendors, subcontractors, and suppliers. An operator may include an airline, leasing company, military entity, service organization, and other suitable operators.

As shown in FIG. 11, the aircraft 566 produced by the exemplary aircraft manufacturing and service method 550 may include an airframe 568 with a plurality of systems 570 and an interior 572. Examples of the plurality of systems 570 may include one or more of a propulsion system 574, an electrical system 576, a hydraulic system 578, and an environmental system 580. Any number of other systems may be included. Although an aerospace example is shown, the principles of the disclosure may be applied to other industries, such as the automotive industry.

Methods and systems embodied herein may be employed during any one or more of the stages of the aircraft manufacturing and service method 550. For example, components or subassemblies corresponding to component and subassembly manufacturing 556 may be fabricated or manufactured in a manner similar to components or subassemblies produced while the aircraft 566 is in service 562. Also, one or more apparatus embodiments, method embodiments, or a combination thereof, may be utilized during component and subassembly manufacturing 556 and system integration 558, for example, by substantially expediting assembly of or reducing the cost of the aircraft 566. Similarly, one or more of apparatus embodiments, method embodiments, or a combination thereof, may be utilized while the aircraft 566 is in service 562, for example and without limitation, to maintenance and service 564.

Disclosed versions of the portable wand system 10 (see FIGS. 1A, 2A-2B, 3A-3B, 5A), including the trainable portable wand system 11 (see FIGS. 1C, 2A-2B) and the trained portable wand system 11a (see FIGS. 1C, 3A-3B), and the method 400 (see FIG. 7), and the method 450 (see FIG. 8) allow a user 52, or operator 54, such as a designated trainer, to preferably first train or program the portable wand system 10, such as the trainable portable wand system 11, in a learn mode 300 (see FIG. 1C), by moving the mobile, manual wand applicator 18 in first learn mode 300a in a desired path 310 (see FIG. 1C) or pattern 306 (see FIG. 1C), in one or more stay-in zones 314 (see FIG. 1C) with one or more surfaces 12 to be surface treated with a surface treatment application 14. Each desired path 310 is preferably recorded using a computing device, such as a CPU 60, that tracks the output 394 of an inertial system disposed within the wand applicator 18, and each desired path 310 is stored within the memory unit 66 of the wand controller subsystem 30.

The user 52, or operator 54, such as the designated trainer, then preferably trains or programs the portable wand system 10, such as the trainable portable wand system 11, in a second learn mode 300b (see FIG. 1C), by moving the mobile, manual wand applicator 18 in one or more stay-out zone paths 312 (see FIG. 1C) in, over, or near one or more stay-out zones 332 (see FIG. 1C) not to be surface treated. Each stay-out zone path 312 is preferably recorded using the computing device, such as the CPU 60, that tracks the output

394 of an inertial system disposed within the wand applicator 18, and each stay-out zone path 312 is stored within the memory unit 66 of the wand controller subsystem 30. The stay-out zone paths 312 or regions that are to be avoided, are trained as stay-out zones 332, may be selected using the manual selector button 25 on the wand applicator 18 during the learn mode 300. In this case, the user 52, or operator 54, such as the designated trainer, positions and orients the wand applicator 18 near the stay-out zones 332 that are to be avoided, while the stay-out zone learn mode selection 342b (see FIG. 1C) is selected or toggled. Further, all areas that are not on the one or more desired paths 310 may be designated as stay-out zones 332. The desired paths 310 and the stay-out zone paths 312 learned and recorded in the learn mode 300 may also be transferred from a portable wand system 10 that has been trained to a portable wand system 10 that has not been trained, via a data connection, and the data transferred may include a home reference location that the wand applicator 18 to be trained may use to orient to the same zone 308 layout.

In addition, disclosed versions of the portable wand system 10 (see FIGS. 1A, 2A-2B, 3A-3B, 5A), the method 400 (see FIG. 7), and the method 450 (see FIG. 8) allow for multiple paths 304, such as desired paths 310 and stay-out zone paths 312, to be stored and selected from the memory unit 66 in the wand controller subsystem 30, using the selector assembly 24, comprising one of, the barcode assembly 348, the RFID assembly 366, or the manual selector assembly 375, as discussed in detail above. For example, the portable wand system 10 can store multiple paths 304 that may be chosen using a barcode 354 (see FIG. 1C), such as a two-dimensional barcode 354a (see FIG. 1C), or a QR code 354b (see FIG. 1C), in the selected stay-in zone 314a to be surface treated or disinfected, or that may be chosen or selected from operator work instructions 358 (see FIG. 1C) that may be scanned with the wand applicator 18. Further, the user 52, or operator 54, may scan a zone 308 (see FIG. 1C), such as a desired zone 308a (see FIG. 1C), with the wand applicator 18 itself, or with a separate mobile device 362 (see FIG. 1C) that communicates with the portable wand system 10, allowing the portable wand system 10 to recall the desired path 310, or preferred path, for the desired zone 308a, such as the stay-in zone 314, for example, the selected stay-in zone 314a. The user 52, or operator 54, may also select from a preprogrammed list 378 on the separate mobile device 362, or on the wand applicator 18 itself, the selected desired path 310b (see FIG. 1C), or preferred path, for the selected stay-in zone 314a (see FIG. 1C) to be surface treated. The separate mobile device 362 can communicate with the portable wand system 10, allowing the portable wand system 10 to recall the desired path 310, such as the selected desired path 310b, for the selected stay-in zone 314a from the preprogrammed list 378. The zones 308 are identified in the geometric model 36 (see FIG. 1A) as the desired paths 310 to be surface treated, and additionally as the stay-out zones 332, which are surfaces 12 not to be treated. Thus, the portable wand system 10 identifies, selects, and controls the zones 308 to be surface treated, for example, disinfected.

Movement 388 (see FIG. 1C) or subsequent movement 388a (see FIG. 1C), or motion of the wand applicator 18 in the operator path 386, by the user 52, or operator 54, is then compared to the desired path 310 (see FIG. 1C) that has been recorded and stored in the memory unit 66 to determine if some, or all, of the operation path 386 has not deviated too far from the desired path 310, and if so, where those deviations 387 (see FIG. 1C) have occurred, and indicating those surfaces 12, zones 308, or other areas, to the user 52, or operator 54, thus identifying the surfaces 12, or zones 308, or other areas, requiring re-application of the surface treatment application 14.

In addition, disclosed versions of the portable wand system 10 (see FIGS. 1A, 2A-2B, 3A-3B, 5A), including the trained portable wand system 11*a* (see FIG. 1C), and the method 400 (see FIG. 7), and the method 450 (see FIG. 8) indicate to the user 52, or operator 54 when the operation path 386 deviates from the desired path 310, and when the wand applicator 18 is in proximity to, and oriented towards, one or more of the plurality of stay-out zones 332, to allow the user 52, or operator 54, to control the output 394 (see FIG. 1C) of the wand applicator 18, for example, adjusting movement 388 (see FIG. 1C) of the wand applicator 18 and adjusting power 121 (see FIG. 1A) to the wand applicator 18. Adjusting the power 121 to the wand applicator 18, is triggered by the computer program 32, such as the algorithm 32*a*, of the CPU 60, providing a feedback signal 390 (see FIG. 1C) to the power assembly 108 to cause the power assembly 108 to reduce the power 121, or to extinguish the power 121, to the surface treatment application element 16, for example, the UV lamp element 26, of the wand applicator 18, if the wand applicator 18 is inappropriately aimed or positioned in, over, or near one or more stay-out zones 332. The zones 308 are preprogrammed such that the power 121 is reduced to curtail the output 394 of the wand applicator 18, such as the UV light 28 (see FIG. 1A), if the position 50 of the wand applicator 18 does not align well with those areas designated as the stay-out zones 332.

Further, when the wand applicator 18 is in proximity to, and oriented towards, one or more of the plurality of stay-out zones 332, the portable wand system 10 issues a warning or alert, such as with sound, e.g. beep, tone, vibration, or visual alert, to the user 52, or operator 54, by the computer program 32, such as the algorithm 32*a*, of the CPU 60, triggering the indicator element 78 (see FIG. 1A) to notify the user 52, or operator 54, of an incorrect position 392 (see FIG. 1C) of the wand applicator 18, such as if the wand applicator 18 is aimed in the stay-out zone 332 or an undesirable area, for example, flight deck windows 334 (see FIG. 4B).

Disclosed versions of the portable wand system 10 (see FIGS. 1A, 2A-2B, 3A-3B, 5A), the method 400 (see FIG. 7), and the method 450 (see FIG. 8) validate that the surface treatment application 14, such as a desired surface treatment application 14*b* (see FIG. 1B), has been adequately administered. In particular, the portable wand system 10 indicates and verifies that the desired surface treatment application 14*b* (see FIG. 1B) is achieved for the one or more surfaces 12 to be surface treated with the surface treatment application 14 in the selected stay-in zones 314*a*. Moreover, disclosed versions of the portable wand system 10 (see FIGS. 1A, 2A-2B, 3A-3B, 5A), the method 400 (see FIG. 7), and the method 450 (see FIG. 8) allow for verification and validation to users 52, or operators 54, in real-time and to inspectors 56 (see FIG. 1A), such as independent inspectors, after the surface treatment applications 14, such as desired surface treatment applications 14*b*, are complete, that disinfection, sanitization, decontamination, or another surface treatment application 14, or process, requiring a minimum surface exposure has been achieved for one or more surfaces 12 of an area or object. The portable wand system 10 also allows the user 52, or operator 54, to self-verify that the surface treatment application 14 has been sufficiently performed and completed. Additionally, the portable wand system 10 indicates the sufficiency of other processes, such as curing operations 180 (see FIG. 1B), such as a curing operation of a surface coating 180*a* (see FIG. 1B), or UV curing of surface coatings, a shot peening operation 182 (see FIG. 1B), such as a shot peening operation of a metallic surface 182*a* (see FIG. 1B), a chemical contaminant detection operation 184 (see FIG. 1B), a biological contaminant detection operation 186 (see FIG. 1B), a non-destructive inspection processes 188 (see FIG. 1B), such as an eddy current crack detection 190 (see FIG. 1B), or another suitable surface treatment application.

Disclosed versions of the portable wand system 10 (see FIGS. 1A, 2A-2B, 3A-3B, 5A), the method 400 (see FIG. 7), and the method 450 (see FIG. 8) provide a high degree of repeatability, a high degree of quality control, a high degree of efficiency, and an improved consistency to produce a high quality surface treatment application 14, while keeping the dexterity of users 52, or operators 54, performing the surface treatment application 14, as opposed to automated methods requiring highly complex equipment that are less dexterous than a human operator, when a complex surface is to be treated. The portable wand system 10 utilizes the high dexterity of a user 52, or operator 54, such as a human operator, while achieving the traceability and repeatability of an automated process. The portable wand system 10 enables the adaptability of a human operator, with the traceability of automated processes, but without the complexity. The portable wand system 10 provides a surface treatment application 14, such as a disinfection operation 168, that validates and verifies that the surface treatment application 14, such as the disinfection operation 168, has been achieved for a surface 12 using the wand applicator 18, such as a handheld wand applicator 18*a* (see FIG. 1A). The portable wand system 10 performs surface treatment applications, such as disinfection, sanitization, and other surface treatment processes, and indicates and verifies to a user 52, or operator 54, when a surface 12 has been sufficiently treated with a surface treatment application 14, such as a manual surface treatment application, using learned paths 304*a* (see FIG. 1C) and mode selections 340 (see FIG. 1C), that indicate to a user 52, or operator 54 that a stay-out zone 332 has been entered, and that maintain a high degree of quality control and efficiency.

Many modifications and other versions of the disclosure will come to mind to one skilled in the art to which this disclosure pertains having the benefit of the teachings presented in the foregoing descriptions and the associated drawings. The versions described herein are meant to be illustrative and are not intended to be limiting or exhaustive. Although specific terms are employed herein, they are used in a generic and descriptive sense only and not for purposes of limitation.

What is claimed is:

1. A portable wand system comprising:
a wand applicator containing a surface treatment application element;
a wand controller subsystem coupled to the wand applicator, the wand controller subsystem comprising:
a computer program;
a 6 degrees of freedom inertial measurement unit (IMU);
a central processing unit (CPU) coupled to the IMU;
a surface treatment application element power feedback to the CPU;
a memory unit coupled to the CPU; and
a CAD (computer-aided design) model of a plurality of paths learned, and recorded by the CPU, during a learn mode, by an operator manually moving the wand applicator, and the plurality of paths stored in the memory unit, the plurality of paths comprising:

a plurality of desired paths in a plurality of stay-in zones having one or more surfaces to be surface treated with a surface treatment application of the surface treatment application element; and a plurality of stay-out zone paths in, or near, a plurality of stay-out zones to be avoided with the surface treatment application;

a selector assembly operatively coupled to a manual selector button;

an indicator element to indicate that the surface treatment application of one or more of the one or more surfaces is complete, and to indicate when the wand applicator is in an incorrect position; and a power assembly coupled to the wand applicator, wherein the portable wand system is used in an operation mode after the learn mode, to measure, in real-time, the operator manually moving the wand applicator in one or more operation paths, based on the CAD model of the one or more of the plurality of desired paths, in one or more of the plurality of stay-in zones, with the surface treatment application element activated, and further wherein, for a selected stay-in zone, the portable wand system compares the operation path to the CAD model of the desired path, and indicates to the operator when the operation path deviates from the CAD model of the desired path, and when the wand applicator is in proximity to, and oriented towards, one or more of the plurality of stay-out zones, and the portable wand system verifies that a desired surface treatment application is achieved.

2. The portable wand system of claim 1, wherein the selector assembly comprises a barcode assembly comprising a barcode camera coupled to the wand applicator, decoder electronics coupled to the wand applicator or to the barcode camera, and one or more barcodes located in one or more of the plurality of stay-in zones and located in one or more of the plurality of stay-out zones, wherein the barcode camera is designed to read the one or more barcodes.

3. The portable wand system of claim 1, wherein the selector assembly comprises a radio frequency identification (RFID) assembly comprising a radio frequency identification (RFID) reader coupled to the wand applicator, radio frequency identification (RFID) electronics coupled to the wand applicator, and one or more radio frequency identification (RFID) tags located in one or more of the plurality of stay-in zones and located in one or more of the plurality of stay-out zones, wherein the RFID reader is designed to read the one or more RFID tags.

4. The portable wand system of claim 1, wherein the selector assembly comprises a manual selector assembly comprising a manual selection device coupled to the wand applicator, and a preprogrammed list of identifiers corresponding to the plurality of stay-in zones and corresponding to the plurality of stay-out zones, wherein the preprogrammed list is accessible with the manual selection device comprising one of, a selection element on the wand applicator, a keypad device coupled to the wand applicator, and a separate mobile device having an application designed to communicate with the portable wand system.

5. The portable wand system of claim 1, wherein the manual selector button allows the operator to select from a plurality of mode selections and from a plurality of zone selections, the plurality of mode selections comprising a learn mode selection and an operation mode selection, and the plurality of zone selections comprising a plurality of stay-in zone selections and a plurality of stay-out zone selections.

6. The portable wand system of claim 1, wherein, when the wand applicator is in proximity to, and oriented towards, one or more of the plurality of stay-out zones, the computer program provides a feedback signal to the power assembly to cause the power assembly to reduce power or to extinguish power to the surface treatment application element of the wand applicator.

7. The portable wand system of claim 1, wherein, when the wand applicator is in proximity to, and oriented towards, one or more of the plurality of stay-out zones, the computer program triggers the indicator element to notify the operator of the incorrect position of the wand applicator, wherein the indicator element comprises a binary indicator comprising one of, a light signal coupled to the wand applicator, a surface treatment application element flashing light alert, an audio alert, a sound alert, a tactile alert, a vibration alert, a pulsing alert, and a pressure altering alert.

8. The portable wand system of claim 1, wherein the 6 degrees of freedom inertial measurement unit (IMU) further comprises an integrated circuit and an accelerometer.

9. The portable wand system of claim 1, wherein the surface treatment application element comprises one of, an ultraviolet (UV) lamp element, a gaseous dispersal element, an aerosolized element, a disinfectant fluid, a disinfectant gas, a sanitizing fluid, a sanitizing gas, a sterilizing fluid, a sterilizing gas, a cleaning solution, a curing element, a shot peening element, a contamination detection element, a paint, an abrasive media blasting element, a sand blasting element, a surface pre-heating element, and a torch welding element.

10. A method to indicate and verify that a desired surface treatment application is achieved for one or more surfaces, the method comprising the steps of:

providing a portable wand system comprising:

a wand applicator containing a surface treatment application element;

a wand controller subsystem coupled to the wand applicator, the wand controller subsystem comprising:

a computer program;

a 6 degrees of freedom inertial measurement unit (IMU);

a central processing unit (CPU) coupled to the IMU;

a surface treatment application element power feedback to the CPU;

a memory unit coupled to the CPU; and a CAD (computer-aided design) model of a plurality of paths learned and recorded by the CPU, during a learn mode, by an operator manually moving the wand applicator, and the plurality of paths stored in the memory unit, the plurality of paths comprising:

a plurality of desired paths in a plurality of stay-in zones having the one or more surfaces to be surface treated with the desired surface treatment application of the surface treatment application element; and a plurality of stay-out zone paths in, or near, a plurality of stay-out zones to be avoided with the desired surface treatment application;

a selector assembly operatively coupled to a manual selector button;

an indicator element to indicate that the surface treatment application of one or more of the one or more surfaces is complete, and to indicate when the wand applicator is in an incorrect position; and a power assembly coupled to the wand applicator;

training the portable wand system in the learn mode, by the operator manually moving the wand applicator in the plurality of desired paths in the plurality of stay-in zones to be surface treated, and manually moving the wand applicator in the plurality of stay-out zone paths in, or near, the plurality of stay-out zones not to be surface treated;

recording and storing, with the portable wand system, the plurality of desired paths corresponding to the plurality of stay-in zones, and the plurality of stay-out zone paths corresponding to the plurality of stay-out zones;

selecting, with the portable wand system, a selected stay-in zone having the one or more surfaces to be surface treated, and selecting the desired path corresponding to the selected stay-in zone;

operating the portable wand system in an operation mode, by the operator manually moving the wand applicator in an operation path, based on the CAD model of the desired path, in the selected stay-in zone, with the surface treatment application element activated;

comparing, with the portable wand system, the operation path to the CAD model of the desired path;

indicating to the operator, with the portable wand system, when the operation path deviates from the CAD model of the desired path, and when the wand applicator is in proximity to, and oriented towards, one or more of the plurality of stay-out zones, to allow for adjusting movement of the wand applicator and adjusting power to the wand applicator; and verifying, with the portable wand system, that the desired surface treatment application is achieved for the one or more surfaces in the selected stay-in zone.

11. The method of claim 10, further comprising before operating the portable wand system in the operation mode, the step of pressing the manual selector button, to identify, with a registration feature, a starting position at one of the one or more surfaces to be surface treated in the selected stay-in zone, wherein the registration feature registers the wand applicator against a known location in the selected stay-in zone.

12. The method of claim 10, further comprising before training the portable wand system in the learn mode, the step of selecting, with the manual selector button, a learn mode selection, to activate the portable wand system in the learn mode.

13. The method of claim 10, wherein indicating when the wand applicator is in proximity to, and oriented towards, one or more of the plurality of stay-out zones, further comprises, indicating when the wand applicator is in proximity to, and oriented towards, one or more of the plurality of stay-out zones, to allow for adjusting the power to the wand applicator, by the computer program providing a feedback signal to the power assembly to cause the power assembly to reduce the power, or to extinguish the power, to the surface treatment application element of the wand applicator.

14. The method of claim 10, wherein indicating when the wand applicator is in proximity to, and oriented towards, one or more of the plurality of stay-out zones, further comprises, indicating when the wand applicator is in proximity to, and oriented towards, one or more of the plurality of stay-out zones, to allow for adjusting the movement of the wand applicator, by the computer program triggering the indicator element to notify the operator of the incorrect position of the wand applicator, wherein the indicator element comprises a binary indicator comprising one of, a light signal coupled to the wand applicator, a surface treatment application element flashing light alert, an audio alert, a sound alert, a tactile alert, a vibration alert, a pulsing alert, and a pressure altering alert.

15. The method of claim 10, wherein providing the portable wand system further comprises, providing the portable wand system having the selector assembly comprising a radio frequency identification (RFID) assembly comprising a radio frequency identification (RFID) reader coupled to the wand applicator, radio frequency identification (RFID) electronics coupled to the wand applicator, and one or more radio frequency identification (RFID) tags located in one or more of the plurality of stay-in zones and located in one or more of the plurality of stay-out zones, wherein the RFID reader is designed to read the one or more RFID tags.

16. The method of claim 10, wherein verifying that the desired surface treatment application is achieved further comprises, verifying that the desired surface treatment application is achieved, where the desired surface treatment application comprises one of, a disinfection operation, an ultraviolet (UV) light disinfection operation, a decontamination operation, a sanitization operation, a sterilization operation, a curing operation, a shot peening operation, a chemical contaminant detection operation, a biological contaminant detection operation, a non-destructive inspection process, an eddy current crack detection, a paint application, an abrasive media blasting operation, a sand blasting operation, a surface pre-heating operation, and a torch welding operation.

17. A method to indicate and verify that a desired ultraviolet (UV) light disinfection is achieved for one or more surfaces in an interior of an aircraft, the method comprising the steps of:

providing a portable wand system comprising:

a wand applicator containing a surface treatment application element comprising an ultraviolet (UV) lamp element;

a wand controller subsystem coupled to the wand applicator, the wand controller subsystem comprising:

a computer program;

a 6 degrees of freedom inertial measurement unit (IMU);

a central processing unit (CPU) coupled to the IMU;

a surface treatment application element power feedback to the CPU;

a memory unit coupled to the CPU; and a CAD (computer-aided design) model of a plurality of paths learned and recorded by the CPU, during a learn mode, by an operator manually moving the wand applicator, and the plurality of paths stored in the memory unit, the plurality of paths comprising:

a plurality of desired paths in a plurality of stay-in zones having the one or more surfaces to be surface treated comprising disinfected with a desired surface treatment application comprising the desired UV light disinfection of the surface treatment application element comprising the UV lamp element; and a plurality of stay-out zone paths in, or near, a plurality of stay-out zones to be avoided with the desired UV light disinfection;

a selector assembly operatively coupled to a manual selector button;

an indicator element to indicate that the surface treatment application of one or more of the one or more surfaces is complete, and to indicate when the wand applicator is in an incorrect position; and a power assembly coupled to the wand applicator;

selecting, with the manual selector button, a learn mode selection, to activate the portable wand system in the learn mode;

training the portable wand system in a first learn mode of the learn mode, by the operator manually moving the wand applicator in the plurality of desired paths in the plurality of stay-in zones having the one or more surfaces to be disinfected with the UV lamp element;

recording and storing, with the portable wand system, the plurality of desired paths corresponding to the plurality of stay-in zones;

training the portable wand system in a second learn mode of the learn mode, by the operator manually moving the wand applicator in one or more of the plurality of stay-out zone paths in, or near, the plurality of stay-out zones not to be disinfected;

recording and storing, with the portable wand system, the one or more stay-out zone paths corresponding to the plurality of stay-out zones;

selecting, with the manual selector button, an operation mode selection, to activate the portable wand system in an operation mode;

selecting, with the selector assembly, a selected stay-in zone having the one or more surfaces to be disinfected, and selecting the desired path, recorded and stored in the first learn mode, corresponding to the selected stay-in zone;

operating the portable wand system in the operation mode, by the operator manually moving the wand applicator, in real-time, in an operation path, based on the CAD model of the desired path, in the selected stay-in zone, with the UV lamp element activated;

comparing, with the portable wand system, the operation path to the CAD model of the desired path;

indicating to the operator, with the portable wand system, when the operation path deviates from the CAD model of the desired path, and when the wand applicator is in proximity to, and oriented towards, one or more of the plurality of stay-out zones, to allow for adjusting movement of the wand applicator and adjusting power to the UV lamp element; and verifying, with the portable wand system, that the desired UV light disinfection is achieved for the one or more surfaces in the selected stay-in zone.

18. The method of claim 17, further comprising before operating the portable wand system in the operation mode, the step of pressing the manual selector button, to identify, with a registration feature, a starting position at one of the one or more surfaces to be disinfected in the selected stay-in zone, wherein the registration feature registers the wand applicator against a known location in the selected stay-in zone.

19. The method of claim 17, wherein indicating when the wand applicator is in proximity to, and oriented towards, one or more of the plurality of stay-out zones, further comprises, indicating when the wand applicator is in proximity to, and oriented towards, one or more of the plurality of stay-out zones, to allow for adjusting the power to the wand applicator, by the computer program providing a feedback signal to the power assembly to cause the power assembly to reduce the power, or to extinguish the power, to the UV lamp element of the wand applicator.

20. The method of claim 17, wherein indicating when the wand applicator is in proximity to, and oriented towards, one or more of the plurality of stay-out zones, further comprises, indicating when the wand applicator is in proximity to, and oriented towards, one or more of the plurality of stay-out zones, to allow for adjusting the movement of the wand applicator, by the computer program triggering the indicator element to notify the operator of the incorrect position of the wand applicator, wherein the indicator element comprises a binary indicator comprising one of, a light signal coupled to the wand applicator, a surface treatment application element flashing light alert, an audio alert, a sound alert, a tactile alert, a vibration alert, a pulsing alert, and a pressure altering alert.

* * * * *